(12) United States Patent
Mack et al.

(10) Patent No.: US 9,822,176 B2
(45) Date of Patent: *Nov. 21, 2017

(54) IL-3 ANTIBODIES AND THEIR USE IN DIAGNOSIS AND TREATMENT OF DISEASES OR MALFUNCTIONS ASSOCIATED WITH ELEVATED LEVELS OF IL-3

(71) Applicant: UNIVERSITATSKLINIKUM REGENSBURG, Regensburg (DE)

(72) Inventors: Matthias Mack, Regensburg (DE); Hilke Brühl, Regensburg (DE); Kerstin Renner, Tegernheim (DE)

(73) Assignee: UNIVERSITÄTSKLINIKUM REGENSBURG, Regensburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,954

(22) PCT Filed: May 29, 2013

(86) PCT No.: PCT/EP2013/061121
§ 371 (c)(1),
(2) Date: Nov. 13, 2014

(87) PCT Pub. No.: WO2013/178706
PCT Pub. Date: Dec. 5, 2013

(65) Prior Publication Data
US 2015/0175693 A1    Jun. 25, 2015

(30) Foreign Application Priority Data
May 29, 2012 (EP) .................... 12169799

(51) Int. Cl.
*C07K 16/24* (2006.01)
*G01N 33/68* (2006.01)

(52) U.S. Cl.
CPC ....... *C07K 16/244* (2013.01); *G01N 33/6869* (2013.01); *C07K 2317/21* (2013.01); *C07K 2317/24* (2013.01); *C07K 2317/33* (2013.01); *C07K 2317/73* (2013.01); *C07K 2317/76* (2013.01); *G01N 2800/00* (2013.01)

(58) Field of Classification Search
None
See application file for complete search history.

(56) References Cited

FOREIGN PATENT DOCUMENTS

| EP | 2193790 A1 | 6/2010 |
|---|---|---|
| WO | 2005/051999 A2 | 6/2005 |
| WO | 2010/063488 A1 | 6/2010 |
| WO | 2010/094068 A1 | 8/2010 |

OTHER PUBLICATIONS

Vajdos et al. (J Mol Biol. Jul. 5, 2002;320(2):415-28 at 416).*
Brown et al. (J Immunol. May 1996;156(9):3285-91).*
Beerli, et al., Isolation of human monoclonal antibodies by mammalian cell display, PNAS, 105(38):14336-14341 (2008).
Hemminki, et al., Familial Associations of Rheumatoid Arthritis With Autoimmune Diseases and Related Conditions, Arthritis & Rheumatism, 60(3):661-668 (2009).
Jakobovits, et al., From XenoMouse technology to panitumumab, the first fully human antibody product from transgenic mice, Nature Biotechnology, 25(10):1134-1143 (2007).
Jones, et al., Replacing the complementarity-determining regions in a human antibody with those from a mouse, Nature, 321:522-525 (1986).
Lantz, et al., Role for interleukin-3 in mast-cell and basophil development and in immunity to parasites, Nature, 392:90-93 (1998).
Li, et al., A comparative study of different vector designs for the mammalian expression of recombinant IgG antibodies, Journal of Immunological Methods, 318:113-124 (2007).
Padyukov, et al., A Gene-Environment Interaction Between Smoking and Shared Epitope Genes in HLA-DR Provides a High Risk of Seropositive Rheumatoid Arthritis, Arthritis & Rheumatism, 50(10):3085-3092 (2004).
Presta, Molecular engineering and design of therapeutic antibodies, Current Opinion in Immunology, 20:460-470 (2008).
Abrams J., "Immunoenzymetric assay of Mouse and Human Cytokines Using NIP-Labeled Anti-Cytokine Antibodies", Current Protocols in Immunology, Suppl. 13:6.20.1-6.20.15 (1995).
Almagro, Juan C., et al., "Humanization of antibodies", Frontiers in Bioscience, 13:1619-1633 (2008).
Anonymous ED—Anonymous: "Human IL-3 Antibody", Jan. 1, 2011, Retrieved from the Internet: URL:http://www.mdsystems.com/pdf/mab603.pdf [retrieved on Jul. 4, 2012].
Anonymous ED—Anonymous: "Human IL-3 ELISA Kit—User Manual", Mar. 1, 2012, Retrieved from the Internet: URL:http://www.ravbiotech.com/manual/ELISA/ELH-IL3-001.pdf [retrieved on Jul. 4, 2012].
Anonymous: "Technical Data Sheet Biotin Rat Anti-human-IL-3", BD Biosciences, 2007, Retrieved from the Internet: URL:http://www.bdbiosciences.com/external_files/pm/doc/tds/brm/live/web_enabled/20572D_554674.pdf [retrieved on Jul. 4, 2012].
Brühl, et al., "Important Role of Interleukin-3 in the Early Phase of Collagen-Induced Arthritis", Arthritis & Rheumatism, 60(5):1352-1361 (2009).
Duronio V. et al., "Antibodies to interleukin 3 as probes for the interaction of interleukin 3 with its receptor", Cytokine, Academic Press Ltd., 3(5):414-420 (1991).
International Search Report for PCT/EP2013/061121, dated Aug. 13, 2013 (4 pages).
International Search Report for PCT/EP2013/061122, dated Jul. 11, 2013 (4 pages).
Jeong, Ki Jun, et al., "Recombinant antibodies: Engineering and production in yeast and bacterial hosts", Biotechnology Journal, 6:16-27 (2011).
Kaushansky Kenny et al., "Structure-function relationships of interleukin-3: An analysis based on the function and binding characteristics of a series of interspecies chimera a gibbon and murine interleukin-3", Journal of Clinical Investigation, 90(5):1879-1888 (1992).
Knopf H-P et al., "A Time-Resolved Fluoroimmunoassay for Recombinant Human Interleukin-3", Annals of Clinical Biochemistry, 30(1):69-71 (1993).

(Continued)

*Primary Examiner* — Brian J Gangle
*Assistant Examiner* — Andrea McCollum
(74) *Attorney, Agent, or Firm* — Kilpatrick Townsend & Stockton, LLP

(57) ABSTRACT

Novel anti-interleukin 3 (IL-3) antibodies or fragments or constructs thereof according to the present invention specifically bind to an epitope contained within the N-terminal 20 amino acids of the amino acid sequence of human IL-3 according to SEQ ID No. 1, and preferably to a sequence motif SWVN (SEQ ID NO: 2). The antibodies can be used in diagnostic methods for the determination of IL-3 levels in body fluids, preferably in corresponding ELISA assays, but also in pharmaceutical compositions for the treatment or prevention of diseases which are associated with elevated levels of IL-3 in a patient, especially rheumatoid arthritis.

12 Claims, 45 Drawing Sheets

(56) References Cited

OTHER PUBLICATIONS

Kontermann, Roland, et al., Antibody Engineering, Laboratory manuals, Springer lab manual, Chapter I, "Recombinant Antibodies", pp. 3-16 (2001).

Lokker, N. et al., "Structure-Activity Relationship Study of Human Interleukin-3 Role of the Carboxyl-Terminal Region for Biological Activity", EMBO (European Molecular Biology Organization) Journal, 10(8):2125-2132 (1991).

Papoian, R. et al., "A sensitive ELISA for measuring recombinant human interleukin-3 in human plasma or serum", Journal of Immunological Methods, 145(1-2):161-165 (1991).

R&D Systems: "Human IL-3 polyclonal goat IgG AF-203-NA", 2011, Retrieved from the Internet: URL:http://www.mdsystems.com/pfd/af203na.pdf [retrieved on Oct. 24, 2012].

Santos, Ameurfina D., et al., "Development of More Efficacious Antibodies for Medical Therapy and Diagnosis", Progress in Nucleic Acid Research and Molecular Biology, 60:169-194.

Office Action in related U.S. Appl. No. 14/400,958 dated Sep. 8, 2016.

Knopf, et al., "A Time Resolved Fluoroimmunoassay for Recombinant Human Interleukin-3," Ann Clin Biochem, 1993 30, pp. 69-71.

Papoian, et al., "A Sensitive ELISA for measuring recombinant human interleukin-3 in human plasma or serum," Journal of Immunological Methods, 145(1991), pp. 161-165.

* cited by examiner

Aminoacid identity of IL-3 between various species

- Human – Mouse: 29%
- Human – Rat: 30%
- Mouse – Rat: 60%
- Human – Marmoset: 72%
- Human – Rhesus: 84%
- Human – Chimpanzee: 99%

Human IL-3 is partially active in Rhesus but not in Marmoset
Rhesus IL-3 is active in humans

Fig. 1

Westernblot with mAbs against IL-3

Each lane : 1 μg/ml recombinant hIL-3
Reducing (β-ME) and denaturing conditions (SDS)

Fig. 20 Binding of biotinylated IL-3 to Monocytes

Fig. 22
Blocking Effect on the stimulation of Basophils
1. Pre-test – FACS-analysis for the stimulation marker CD203c
Stimulation of purified basophils – 5h
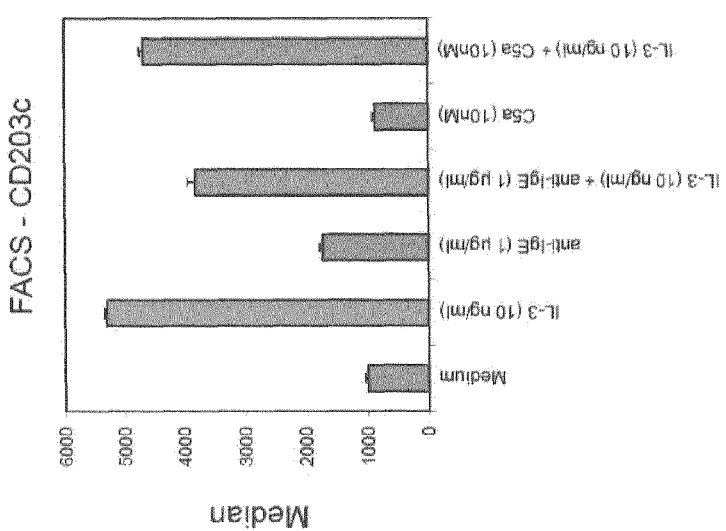
Stimulation of purified basophils – 24h
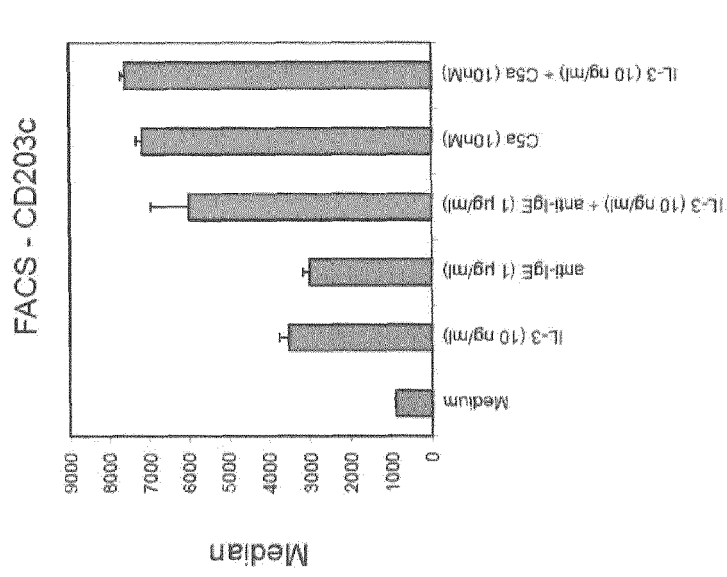

Fig. 23 Blocking Effect on the Stimulation of Basophils
1. Pre-test – Release of IL-13 by activated basophils
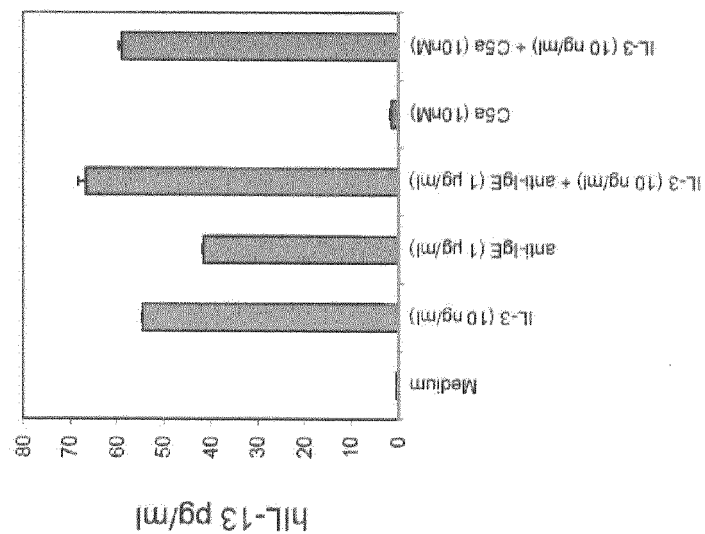
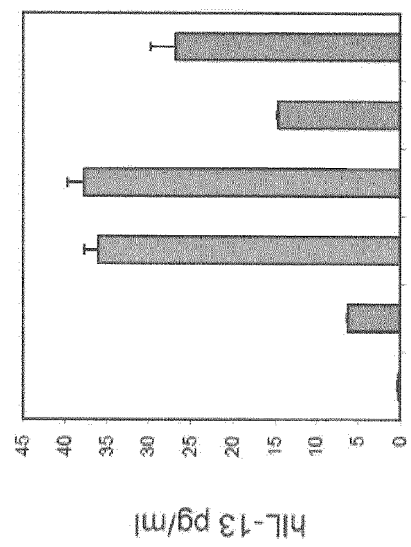

Blocking Effect on the Stimulation of Basophils

1. Pre-test – Release of IL-4 by activated basophils

Epitope-Mapping

Segmentation of human IL-3 into 6 overlapping peptides with 27-28 amino acids

IL3-1 (27 aminoacids): APMTQTTPLKTSWVNCSNMIDEIITHL (SEQ ID NO:3)
IL3-2 (27 aminoacids): EIITHLKQPPLPLLDFNNLNGEDQDIL (SEQ ID NO:4)
IL3-3 (27 aminoacids): EDQDILMENNLRRPNLEAFNRAVKSLQ (SEQ ID NO:5)
IL3-4 (27 aminoacids): AVKSLQNASAIESILKNLLPCLPLATA (SEQ ID NO:6)
IL3-5 (27 aminoacids): LPLATAAPTRHPIHIKDGDWNEFRRKL (SEQ ID NO:7)
IL3-6 (28 aminoacids): EFRRKLTFYLKTLENAQAQQTTLSLAIF (SEQ ID NO:8)

Epitope-Mapping

| | | |
|---|---|---|
| IL3-1 Human | : APMTQTTPLKTSWVNCSNMIDEII | (SEQ ID NO:9) |
| IL3-Rhesus | : APMTQTTSLKTSWAKCSNMIDEII | (SEQ ID NO:10) |
| IL3-1A (24 aminoacids): | APMTQTTPLKTSWAKCSNMIDEII | (SEQ ID NO:11) |
| IL3-1B (24 aminoacids): | APMTQTTSLKTSWVNCSNMIDEII | (SEQ ID NO:12) |
| IL3-Ma (26 aminoacids): | AAPTQTMPLKTTQVNCSNLREEIVTL | (SEQ ID NO:13) |

Fig. 37 ELISA Development - Stability

IL-3 ANTIBODIES AND THEIR USE IN DIAGNOSIS AND TREATMENT OF DISEASES OR MALFUNCTIONS ASSOCIATED WITH ELEVATED LEVELS OF IL-3

CROSS REFERENCE TO RELATED APPLICATIONS

The present application claims priority to EP Application No. 12169799.9, filed May 29, 2012, which is hereby incorporated herein by reference in its entirety.

REFERENCE TO A SEQUENCE LISTING SUBMITTED AS A TEXT FILE VIA EFS-WEB

The sequence listing was submitted via EFS-Web as an ASCII formatted sequence listing with a file named sequencelisting.TXT, created on Apr. 25, 2017, and having a size of 4.98 KB. The sequence listing contained in this ASCII formatted document is part of the specification and is herein incorporated by reference in its entirety.

The present invention relates to novel anti-interleukin 3 (IL-3) antibodies, nucleic acid sequences encoding such antibodies and hybridoma cell lines producing the antibodies according to the present invention. The invention further relates to pharmaceutical compositions containing the novel IL-3 antibodies, which are useful for the prevention or treatment of diseases or malfunctions which are associated with elevated levels of IL-3 in a human patient as well as to diagnostic kits and methods for reliably determining the IL-3 level in the blood, plasma, serum or other body fluid (e.g. urine, synovial fluid) of a patient.

Interleukins belong to the large family of proteins called cytokines. Cytokines are polypeptides that influence the function of certain cells upon binding to specific cellular receptors and are divided in subclasses, i.e., interleukins, interferons, colony-stimulating factors (CSFs), lymphokines, growth factors and monokines. It is well known that cytokines play a major role in cell proliferation and, e.g., also inflammatory diseases.

Cell proliferation is a complex process wherein growth factors bind to specific receptors on the cell surface, whereupon endocytosis occurs and the complexes of cytokine and receptor are internalized causing a cellular response. Such cellular responses include specific gene transcription activities as DNA synthesis and cell replication. When tested in relatively high concentrations, most of the cytokines have several differing biological effects. Because of these effects of cytokines, there is a high interest in investigations for possible therapeutic uses of these proteins.

Interleukins are mediators of the immune system which are produced in low concentration mostly in leukocytes. They influence the growth, differentiation and activity of cells of the immune system and thus belong to the immune modulators. They also take effect by binding to receptors on the surface of target cells and thus change the transcription rate of certain genes. They play an important role in the triggering of a multiplicity of cellular responses.

Interleukins are, e.g., involved in the immunological cell activation cascade and subsequent inflammatory changes. Irregular and/or abnormal inflammation is a major component and factor of a wide range of human diseases, one of which is the immunological disorder rheumatoid arthritis (RA). But also other immunological diseases are influenced by interleukins.

IL-3, also designated as Multi-CSF, is a well-known member of the interleukin family. It has a growth stimulating and differentiating effect on various hematopoietic precursor cells and acts as a growth factor for mast cells. Together with IL-5 and GM-CSF, IL-3 belongs to the family of hematopoietic cytokines with four short alpha-helical bundles. GM-CSF and IL-3 stimulate the formation of neutrophilic and eosinophilic granulocyte colonies as well as macrophages. It further stimulates the formation of mast, megakaryocyte and pure and mixed erythroid colonies (D. Metcalf, "The hematopoietic colony-stimulating factors", 1984, Elsevier, Amsterdam).

IL-3 consists of 133 amino acids and is known for its stimulation of colony formation by human hematopoietic progenitor cells and the stimulation of DNA synthesis by human acute myelogenous leukemia (AML) blasts. IL-3 binds to a unique receptor also known as CD123 antigen. The receptor belongs to the type I cytokine receptor family and is a heterodimer with a unique α-chain paired with a common β-subunit (βC or CDW 131). IL-3 binds to the unique α-receptor subunit. Signal transduction is mediated, however, by the common β-receptor subunit (βC) by the JAK2-STAT5 pathway.

IL-3 is mainly produced by activated CD4+ T-cells and contributes especially to growth, differentiation and survival of CD34+ hematopoietic progenitor cells. In vitro, IL-3 has been observed to promote the differentiation of basophiles and mast cells from bone marrow cells. It has further been observed to induce IL-6 release by murine basophils and to up-regulate MHC-II expression and IL-1 secretion in monocyte/macrophages. Further, IL-3 supports the differentiation of monocytes into dendritic cells and osteoclasts.

Since the first detection of IL-3 in a human genomic library, it has been a focus of investigations to determine its role in healthy humans as well as its possible role in the occurrence of diseases. The ability of cytokines to initiate or regulate hematopoiesis is of interest, especially as far as malfunctions or diseases of the immune system are concerned. Such disorders seem to be connected to disturbances of the hematopoietic system and it was assumed that such diseases could be treated by providing viable progenitor cells to the hematopoietic system. Triggering such progenitor cells to differentiate was considered as a means to treat the respective diseases.

Until several years ago, little was known about the role of IL-3 in auto-immune diseases and especially rheumatoid arthritis (RA). RA is the most prevalent inflammatory disease of the joints. The initial disease stages often develop gradually but can also manifest themselves with an instantaneous outburst. While pain occurs predominantly in joints of the fingers or toes, also other joints can be affected. The affected joints show swelling and usually are hyperthermic.

Mostly, the disease proceeds in episodes, an episode usually lasting between several weeks to months. In between episodes, generally, there is an improvement of symptoms.

The etiology of RA is not yet known. An autoimmune cause is strongly suspected with viral and bacterial causes being also discussed. A genetic influence has been reported by several authors (Hemminki K. et al., Arthritis Rheum. 2009; 60(3): 661-8, Padyukov L. et al., Arthritis Rheum. 2004; 50(10) 3085-92). It is assumed that misdirected immune cells invade the affected joints and cause the production of pro-inflammatory cytokines. According to one theory, the balance between cytokines is disturbed in RA. It has been reported that IL-1, IL-6 and TNFα are present in excess in RA and are assumed to be responsible for the deleterious inflammatory processes in cartilage tissue and for the activation of osteoclasts.

The treatment of rheumatoid arthritis is still considered difficult and burden-some to the patients since medications with a high risk of adverse side effects have to be used. One way of treating the disease is to perform a symptomatic treatment, mostly using non-steroidal anti-inflammatory drugs (NSAIDs). These drugs act as anti-inflammatory and analgetic agents and often only achieve an alleviation of pain. The drugs further interfere with a certain step in the inflammatory cascade, where prostaglandine is generated by cyclooxygenases. NSAIDs, however, do not influence the underlying inflammatory process and are thus not able to retard the joint destruction, which is the most deleterious effect of RA.

To prevent joint destruction and disease activity, a further current approach for treating RA is the use of disease-modifying anti-rheumatic drugs (DMARDs). These pharmaceuticals actually modify the disease process. Examples of DMARDs are methotrexate, the most commonly used anti-rheumatic, the effect of which is based on a reversible inhibition of the enzyme dihydrofolate reductase. Another commonly used substance for treating RA is leflunomide, which provides an effect by intervening with the pyrimidine metabolism. Both pharmaceuticals are long-acting and thus have to be administered over a longer period of time (usually 12-16 weeks) to show the desired effects. To bridge the time until DMARDs improve the disease, most patients are administered steroids.

A further approach for treating RA are "biologicals" that block cytokines like TNF, IL-6, IL-1 or costimulatory molecules like B7 or that deplete leukocyte subsets (e.g. B cells). Biologicals (e.g. the TNF antibody Infliximab) are mostly used for severe disease processes and after DMARDs have failed to sufficiently control disease activity. Biologicals influence a plurality of signal systems in the immune system and have a variety of serious side effects including bacterial and viral infections and a higher risk for development of neoplasia.

All known treatments have severe disadvantages and side effects and, therefore, it was an object to develop new drugs for the treatment of RA which are effective, are more selectively expressed than other cytokines in patients with autoimmune disease especially RA and have less side effects than the currently used treatment regimes.

More recently, an involvement of IL-3 in autoimmune diseases and especially in RA has been described. WO 2010/063488 describes that IL-3 inhibitors can be used in treatment of early stages of rheumatoid arthritis. Although the patent application mentions that no IL-3 mRNA was detected in the synovium of patients with RA and no effect of IL-3 was observed on cultured fibroblasts, a genetic analysis found an association between a single nucleotide polymorphism in the IL-3 promoter gene and RA. Based on this finding and also further studies which show the presence of considerably elevated levels of IL-3 in RA patients, WO 2010/063488 proposes such use of inhibitors, mainly antibodies or antibody fragments, antibody variants or antibody multimers in prophylactic RA treatment, therapeutic treatment in early stages of the disease or in maintenance treatment.

However, there is still a need for effective antibodies with high specificity towards IL-3 which also show a high affinity and avidity. Such antibodies are desirable for an envisioned therapeutic use but also for a meaningful and reliable diagnosis. Test results that have been produced within the research framework that led to the present invention indicate that not in all RA patients symptoms and systemic inflammation correlate with an elevated IL-3 level. Obviously there are different groups of RA patients as far as involvement of IL-3 in the propagation of the disease is concerned. Accordingly, patients that do not show elevated levels of IL-3 in acute phases of the disease, most probably would not benefit from a treatment with anti-IL-3 antibodies. Unprofitable expenses to the health system can be avoided by a reliable diagnostic test with regard to the presence of IL-3 in the blood or serum of patients. Currently available commercial diagnostic test kits for IL-3 determination have not proven reliable when conducted directly on blood, plasma or serum. Therefore, it was a further object of the present invention to provide antibodies that do not substantially cross-react with other human interleukins or cytokines like IL-5 or GM-CSF and thus are able to reliably detect elevated IL-3 levels in a diagnostic assay.

Such anti-IL-3 antibodies preferably should also exhibit none or very low cross reactivity with IL-3 from other species. Within this object of the present invention, it is desirable to provide antibodies which are able to inhibit the activity of IL-3 efficiently and specifically, thus making them useful agents for treating the disease in patients having been diagnosed for elevated levels of IL-3.

These objects of the present invention are solved by novel anti-IL-3 antibodies or fragments or constructs thereof according to the present invention as specified in the appended claims and the following description. The characteristic feature of the antibodies of the present invention is that they specifically bind to an epitope contained within the N-terminal 20 amino acids of the amino acid sequence of human IL-3 according to SEQ ID No: 1.

It has been determined that within this N-terminal region of IL-3, at least one epitope is located which is a very specific binding site for anti-human-IL-3 antibodies. Antibodies which are directed against an epitope which is located in this very N-terminal region show surprisingly little cross-reactivity to other cytokines present in the blood of a patient, especially GM-CSF and IL-5 and thus are very well adapted to therapeutic and diagnostic methods envisaged according to this invention.

Preferred antibodies bind specifically to an epitope which is contained within amino acids 8 and 18 of SEQ ID No: 1 and in an especially preferred embodiment, the anti-IL-3 antibody of the present invention specifically binds to an epitope which contains the sequence motif according to SEQ ID NO: 2, namely, the amino acids SWVN.

Apart from a very high specificity for only IL-3 but not other cytokines, the antibodies of the present invention show also surprisingly low levels of cross-reactivity with IL-3 molecules of other mammalian origin. Amino acid identities of a human protein and the mouse protein is 29% which seems quite low. However for marmoset, rhesus or a chimpanzee proteins there are amino acid identities between 72 and 99% (FIG. 1). Antibodies according to the present invention which bind to an epitope within the first 20 amino acids of human IL-3 and especially the antibodies binding specifically to the amino acid sequence motif SWVN (SEQ ID NO: 2) show surprisingly little cross-reactivity to such highly similar proteins from other species (e.g. rhesus, rat, mouse, marmoset).

As regards the further cytokines, which may also be present at an elevated level in autoimmune diseases, IL-5 and GM-CSF are particularly important. A high cross-reactivity of an anti-IL-3 antibody with such cytokines in an immunoassay can lead to incorrect results regarding the fact whether an IL-3 overexpression has an important influence in the manifestation and progression of the autoimmune disease. Such results, however, have an important impact on the decision whether the application of an anti-IL-3 antibody can be considered a promising therapeutic approach.

It is thus preferred for inventive antibodies to show the lowest possible cross-reactivity with human IL-5 and GM-CSF. Particularly preferred, it is a characterizing feature of an inventive antibody that it binds to IL-5 or GM-CSF to an extent of below 5%, more preferred below 2% and particularly preferred below 1% as compared to the amount of IL-3 bound by the antibody.

The examples enclosed with this specification show the superior characteristics with regard to specificity and lack of cross-reactivity with IL-3 of other species and with other human cytokines for antibodies according to the present invention.

The antibodies according to the present invention can be of different nature and the following more detailed illustrations of possible antibodies or antibody constructs are only meant to be exemplary. That means that within the context of the present invention the term antibody is to be understood in its broadest sense. Any antibody, part thereof or construct containing antibody characteristics and retains the specificity of the antibodies shown in the examples of the present invention, is considered as encompassed within the term antibody in the context of the present invention.

In principle, monoclonal antibodies as well as polyclonal antibodies can be used. Monoclonal antibodies generally have the advantage of a higher specificity as compared to polyclonal antibodies and are thus preferred in view of the present invention. In terms of the present invention, the term "antibody" shall also comprise fragments, bi-, tri- or multimeric or bi-, tri- or multifunctional antibodies having several antigen binding sites which preferably are IL-3-specific binding sites. At least one of such IL-3-specific binding sites is directed to an epitope present on the 20 N-terminal amino acids and preferably present between amino acids 8 and 18 of SEQ ID NO: 1 and especially preferred directed to the motif SWVN (SEQ ID NO: 2). Regarding the present invention, the term "antibody" further comprises fusion proteins containing as a part of the fusion protein an antibody or antibody fragment or complement determining region (CDRs) of an antibody of the present invention, which show a corresponding specificity and which have furthermore retained their binding ability to IL-3. Further comprised are single chain antibodies. Moreover, the inventive antibodies can belong to any appropriate antibody class, it is however essential that their use in therapy and diagnostics is possible. Preferably, the anti-IL-3 antibody or the fragment thereof according to the present invention is of the class IgG, IgA, IgE oder IgM.

In the present description of antibodies according to the invention, the term "antibody" is meant to also encompass immunologically effective fragments of antibodies. As far as fragments of the inventive antibody are concerned, it is preferred that the fragments retain an antigen-binding domain and an Fc-domain. As an alternative, Fab or F(ab)$_2$ fragments can be used as long as they intervene with the binding of IL-3 to its receptor on the cell surface or with the ability of IL-3 to activate its receptor.

In summary, for the purpose of the present invention, the actual form of a molecule considered to be encompassed by the term "antibody" is irrelevant as long as it specifically binds to IL-3 in diagnostic assays and, as far as a therapeutic use is considered, in a manner sufficient to inhibit the binding of IL-3 to its natural receptor and thus to prevent the cellular reaction triggered thereby.

Antibodies according to the present invention which specifically bind to the first 20 amino acids and preferably amino acids 8 to 18 of IL-3 or most preferably specifically recognize the epitope SWVN (SEQ ID NO: 2) can be produced by any method known to the skilled person. For example, antibodies can be generated using the complete hIL-3 protein as an immunogen and lateron selecting for antibodies and antibody clones which are specific for the mentioned sequences. As an alternative, a peptide containing within its sequence the desired parts or epitopes of IL-3 can be used for immunization. A further possibility is the use of artifical epitopes which contain only the very epitope (conformationally discriminating epitope, CDE) integrated into an environment which allows for the generation of antibodies. Such methods are known to the skilled person and described e.g. in WO2005/051999. In summary, any method for producing antibodies is useful within the context of the present invention as long as it produced antibodies with the required specificity and if necessary allows for the selection of the inventive antibodies from a plurality of antibodies which are produced upon immunization with IL-3 or parts thereof.

The antibody of the invention can also be of any origin, e.g. human, mouse, goat, rabbit. Human or humanized antibodies are particularly preferred. As a commonly used method, the production of antibodies is carried out by immunizing appropriate mammals, e.g., mice, rat, hamster or rabbits.

Especially for a therapeutic use, however, it is less desirable to use non-human proteins since they can cause quite severe adverse reactions of the immune system. This is for example one cause of severe side effects of the presently used mouse antibody infliximab mentioned above.

For the subject matter of the present invention, wherein the antibodies are intended for therapeutic use, it is thus particularly preferred for the antibodies to be human antibodies or that a humanization of antibodies produced in other species is performed. Methods for the humanization of antibodies are known to a person skilled in the art and are described in, e.g., Jones P. T. et al., Nature 1986; 321:522-525, Santos A. D. and Padlan E. A., Frog Nucleic Acid Res Mol Biol. 1998; 60:169-94, Presta L. G., Curr Opin Immunol. 2008 August; 20(4):460-70, Almagro J. C. and Fransson J., Front Biosci. 2008 Jan. 1; 13:1619-33.

The term humanized antibody is generally used for antibodies with more than 95% of human origin. Antibodies with less human character, e.g., with 70% human antibody parts, are often designated as chimeric antibodies. Humanized or chimeric antibodies are produced by means of bio-technological methods using recombinant DNA-technology, whereby a part of the animal/mammalian protein, which contains at least the antigen-binding parts, is combined with further parts of a human antibody such that a functional antibody or fragment or construct thereof is produced.

A possibility to produce a humanized antibody is, for instance, to replace at least one of the CDRs of a receptor antibody, which is a human antibody, by the ones of an IL-3 specific antibody which was produced in a non-human mammal. Furthermore, it is possible to use further parts than the at least one CDR of the mammalian antibodies such that the entire CDR-region, the entire variable region or Fab- or Fab-parts are combined with corresponding further parts of the human antibody.

In addition to humanized and chimeric antibodies, also human antibodies can be used within the context of the present invention. Human antibodies can be prepared using techniques for human monoclonal antibody production as described in the art. One commonly used method is the so-called phage display technique where human antibodies are produced using phage displayed libraries. In this technique, DNA sequences coding for human antibodies are inserted into phage DNA to provide a phage DNA library. Each phage in the library carries a different antibody on its surface. Such libraries can be screened for antibodies that bind the desired antigen. According to the present invention, screening needs to be performed with regard to the epitope contained within the first 20 N-terminal amino acids and preferably within amino acids 8-18 and especially preferred with regard to the epitope containing the amino acid motif according to SEQ ID NO: 2, SWVN. Upon mixing of such library with the antigen/epitope-carrying protein or peptide, only phages with antigen-specific antibodies are selected. Such phages carrying specific antibodies can be propagated and the antibody obtained therefrom in high amounts. Similar to hybridoma cells, also mammalian cells which are transformed with a genetic information from such phages can produce antibodies consecutively (see, e.g., Beerli et al., PNAS Sep. 23, 2008 vol. 105 no. 38 14336-14341).

As a further possibility, human antibodies can also be obtained from transgenic animals. Also by this method, complete human antibodies can be obtained. For this technique, genetically engineered transgenic mice are prepared to carry the human antibody genes. While the expression of mouse-specific antibody genes is suppressed, the expression of human antibody genes is promoted in such mice. Technologies using transgenic mutant mice that are capable of producing human antibodies in response to immunization have been described in the art and are available to the skilled person, e.g. XENOMOUSE® mouse technology (see, e.g., Jakobovits A., Nature Biotechnology 25, 1134-1143 (2007)), or ULTIMAB® mouse technology from Medarex.

By means of an enzyme-linked immunosorbent assay (ELISA), the specifity and cross-reactivity of the produced antibodies according to the invention can be easily determined. In this context, recombinantly produced cytokines (e.g. human IL-3, IL-5 and GM-CSF, or IL-3 from other species, respectively) are coated onto a suitable surface in the test arrangement, the produced anti-human-IL-3-antibodies are added and their binding is detected on the coated surface by means of a corresponding detection reagent, such as a labelled anti-IgG-antibody. In such a test regimen, antibodies according to the present invention bind nearly exclusively to IL-3 while binding to IL-5 and GM-CSF occurs only to a very minor extent, if at all. The same is true for antibodies according to the invention as far as IL-3 from other species is concerned. Especially the preferred antibodies binding specifically to the epitope SWVN (SEQ ID NO: 2) do not cross-react with protein from other species to a detectable extent (see Example 4).

For the selection of particularly suitable antibodies, the affinity of same is examined by further ELISA assaying. In this context, ELISA plates are coated with any anti-human-IL-3 antibody which can also be a commercially available antibody (e.g., a goat IgG anti-human-IL-3 antibody). In this respect, for instance, 1 ug/ml of the antibody is incubated with the ELISA plates over night in a refrigerator whereupon a washing step and a blocking with human IL-3 (250 ng/ml in PBS buffer) is performed, thus fixing human IL-3 on the solid phase. During such a test, candidate antibodies are then added in different concentrations and detected by means of a secondary HRP-(horseradish peroxidase) labelled polyclonal antibody.

A particularly preferred antibody according to the present invention was designated clone 11. Clone 11 is a mouse anti-human-IL-3 antibody and shows a very high specificity and affinity to IL-3. Clone 11 specifically binds to the epitope with the amino acids SWVN according to SEQ ID NO: 2. This particularly preferred antibody was deposited on Mar. 14, 2012 at Leibniz Institute DSMZ-German Collection of Microorganisms and Cell Cultures, Inhoffenstr 7B, D-38124 Braunschweig, Germany under number DSM ACC3163.

In many experiments and also in the examples enclosed to the present specification, clone 11 has proven very superior characteristics with regard to specificity, lack of cross-reactivity but also with regard to affinity and avidity. This preferred antibody therefore is considered especially suitable for use in diagnostics as well as therapeutic measures.

To make this remarkable antibody even more useful for therapeutic uses, a particularly preferred inventive anti-IL-3 antibody is a humanized version of clone 11. For this purpose, clone 11 is humanized in any manner known in the art. In this context, at least one of the CDRs of clone 11 is identically maintained/preserved, other parts of the mouse-antibody clone 11 can entirely or partially be replaced by sequences of human antibody origin. In this context, it is essential that the obtained humanized antibody still shows the same specificity which can easily be determined using known methods. Preferably, such a humanized antibody clone 11 also shows just as little cross-reactivity with IL-3 of species other than the human and with other human cytokines as the deposited mouse clone 11.

A further especially preferred antibody according to the present invention is designated clone 44 and has also been deposited at DSMZ under the accession number DSM ACC3166. Also clone 44 binds specifically to the epitopes which are unique binding sites for the inventive antibodies.

A further subject-matter of the present invention is a nucleic acid which encodes an antibody, an antibody fragment, an antibody construct or sequences for CDRs conveying specificity of antibodies according to the present invention. Besides the production of antibodies via the immunization of animals/mammals route and/or via the hybridoma technique for the production of monoclonal antibodies, it has for some time now also been established to produce antibodies by means of recombinant methods.

Hence, it is also a possible and preferred method to use respective nucleic acids to produce e.g. antibody fragments in bacteria or eukaryotic cells. Corresponding methods for producing recombinant antibodies or antibody fragments are known to a person skilled in the art (see e.g., Jeong K J, Jang S H, Velmurugan N, Biotechnol J. 2011 January; 6(1):16-27. Recombinant antibodies: engineering and production in yeast and bacterial hosts; Li J, Menzel C, Meier D, Zhang C, Dübel S, Jostock T., J Immunol Methods. 2007 Jan. 10; 318(1-2):113-24. A comparative study of different vector designs for the mammalian expression of recombinant IgG antibodies).

The advantages of recombinantly obtained antibodies are that they can be produced entirely outside the animal/mammal organism. In this respect, it is also possible to obtain antibodies which could not be produced in animals/mammals, for instance, because the antigens are substances which are harmful to the organism or because certain biochemical conditions are relevant for the desired antibodies which can only be controlled in an exact manner in an in-vitro system.

Especially for the production of human or humanized antibodies, in particular for therapy, the use of the recombinant antibody technology can be advantageous, since, as already mentioned above, an immune response of the patient against antibodies produced in other organisms can be prevented. Such an immune response to the non-human part of an antibody could neutralize the therapeutic agent or can even jeopardize any positive effect to the patient by entailing severe side effects.

By means of recombinant methods, antibodies and/or their fragments can also readily be coupled with other proteins and also multi-functional and multispecific antibod-ies can be produced (Dübel and Kontermann 2001, Recombinant Antibodies. In: R. Kontermann and S. Dübel (EDS), Antibody Engineering, Springer Verlag, Heidelberg/New York, pages 3-16.)

According to the present invention, a nucleic acid sequence which codes for an inventive antibody comprises nucleotides which encode at least those parts of the antibody which confer the specific binding properties of the antibody to the specific epitope within the 20 N-terminal amino acids of the human IL-3-sequence according to SEQ ID NO: 1. In preferred embodiments, the nucleic acid of the present invention contains at least nucleic acids which encode the amino acids which in the inventive antibodies entail the binding to the epitope between amino acids 8 and 18 of SEQ ID NO: 1 and in particular to the epitope comprising the sequence motive SWVN according to SEQ ID NO: 2.

In a preferred embodiment, the nucleic acid codes for the antibody clone 11 or fragments thereof. A further, especially preferred nucleic acid codes for a humanized clone 11, whereby it comprises at least those nucleotides coding for the regions in antibody clone 11, which entail the binding to the specific human IL-3-epitope according to the present invention.

A further subject-matter of the present invention is a hybridoma cell line which produces a monoclonal anti-IL-3 antibody according to the present invention. Production of hybridoma cell lines obtaining monoclonal antibodies therefrom is well known in the art. Starting out and based on the first publications of the method by Köhler and Milstein, this method has been widely used and further improved. Generally, for the production of monoclonal antibodies, Balb/c mice are immunized with an antigen, in the present case human IL-3 and preferably the parts of IL-3 which contain the first 20 N-terminal amino acids or amino acids 8 to 18 of SEQ ID NO: 1 or, especially preferred the amino acid sequence SWVN (SEQ ID NO: 2). Methods for using desired epitopes for the generation of a specific antibody are well-known in the art. Splenocytes of the immunized mice are fused with myeloma cells and the obtained hybridomas tested for the production of antibodies using, e.g., an ELISA assay. Clones which have tested positive for the production of specific antibodies are further propagated to form a stable hybridoma cell line that can be maintained and used for the consecutive production of the desired antibody.

An especially preferred hybridoma cell line according to the present invention is cell line 11.14.6 (DSM ACC 3163) producing antibody clone 11.

Having described in the above section the first subject matter of the present invention, i.e. the new and advantageous antibodies or antibody fragments or constructs of the present invention as well as their production, e.g. by using nucleic acids encoding such antibodies or using hybridoma cell lines, a further subject matter of the invention is a diagnostic method for determining the IL-3 level in body fluids of a patient, especially in blood, plasma or serum. The method comprises adding an anti-IL3 antibody, fragment or construct thereof according to the present invention to a sample comprising a body fluid sample under conditions which allow for the binding of the antibody or fragment thereof to IL-3 and detecting the amount of antibody-bound IL-3 in the sample.

As already mentioned above, it has been noted that presently available antibodies and test kits for detecting and measuring IL-3 in a sample do not deliver accurate enough results to base a therapeutic approach thereon. Especially for whole blood, plasma and serum, results of commercially available test kits have proven to be unreliable because of high background levels and unspecific cross-reaction being indistinguishable from actual IL-3 binding. Also the binding affinity of known antibodies to IL-3 present in samples of patient blood, plasma or serum has proven insufficient for a correct analysis of a possible influence of IL-3 in an autoimmune disease, especially in RA.

By using the antibodies according to the present invention in diagnostic methods and corresponding test kits, the accurate determination of the presence of IL-3 in body fluids can be improved to a major extent and such methods and test kits, therefore, are a further subject matter of the present invention. It has surprisingly been found that using the antibodies and methods of the present invention, IL-3 could be specifically detected even if present in only picogram/ml concentrations in a sample. The relative affinity of the antibodies of the present invention towards IL-3 is thus about at least a factor 100 higher than the affinity of known antibodies.

In a preferred embodiment of the present invention, the diagnostic method is conducted as an ELISA assay. The general test regime used for ELISA assays is well known to the skilled person. At least two antibodies which bind to the target molecule are used. One of these antibodies is bound to a solid phase allowing for the separation of the antigen to be determined from the test sample. Upon removal of the test sample from the solid phase and washing steps as considered appropriate, a second antigen-specific and labeled antibody is added and after further removal of excess labeled antibody and optionally further washing steps the amount of label bound via the antibody-antigen-antibody complex is determined and correlated to the amount of antigen present.

Although it is necessary that both antibodies used in such an ELISA assay are specific to the antigen to a high extent, an especially high degree of specificity is needed mainly in one of the two antibodies involved. E.g., as a first solid phase-bound antibody a very specific antibody can be used to be able to separate only the desired antigen from the liquid sample without any cross-reacting background. If only the desired antigen is coupled via the antibody to the solid surface, the specificity of the second antibody is not so decisive anymore since unspecific binding to other antigens is not an issue in such a case. Accordingly, it is possible to use a less specific antibody as the second antibody in such a context.

Alternatively, it is possible to use a high affinity and high avidity antibody as the first solid phase-bound antibody and to use a highly specific antibody as the second and labeled antibody. In such an embodiment, unspecific binding of other antigens like IL-5 or GM-CSF might take place to some extent due to a certain cross-reactivity of the first antibody, however, the actual detection by the labeled antibody is then restricted to IL-3 by using a highly specific second antibody.

In a preferred embodiment according to the present invention, an ELISA assay method and kit are used wherein as the highly specific antibody in the test an antibody according to the present invention is used. In a particularly preferred embodiment, the highly specific antibody used in the ELISA assay is antibody clone 11.

To avoid possible steric hindrance issues for the ELISA performance, it is preferable to use a second antibody that binds to an epitope of IL-3 at another part of the protein. Thus the second antibody will normally not bind to an epitope contained within the first 20 amino acids of IL-3 according to SEQ ID No. 1, if the first antibody against IL-3 binds to an epitope contained within the first 20 amino acids of IL-3 (SEQ ID No. 1) and vice versa. It is well within the ambit of the present invention to use a known and commercially available antibody as the second antibody. However, according to the present invention preferred combinations of antibodies (first antibody/second antibody) are clone 13/11 (most preferred), clone 11/13 (preferred). clone 13/44, and clone 44/13 as well as combinations of clones 11 or 44 with clone 47. Clone 13 and clone 47 are considered to bind to a 3-D epitope of IL-3 in its native conformation. The above mentioned clones were deposited at DSMZ in Braunschweig/Germany: clone 11 (11.14.6)=DSM ACC3163; Clone 13 (13.4.4)=DSM ACC3164; Clone 44 (44.16.16)=DSM ACC3166; clone 47 (47.28.15)=DSM ACC3167.

Although it might be useful for diagnostic purposes to be able to detect IL-3 in any body fluid or also cell preparation, the present diagnostic method is especially suited and useful for the detection of IL-3 in a plasma or serum sample. With the heretofore known methods and antibodies, detection of IL-3 in plasma or serum did not lead to sufficiently meaningful results especially due to cross-reactivities of known antibodies and insufficient affinities of such antibodies with regard to the low levels of IL-3 in present blood, plasma or serum in healthy and in RA patients. Therefore, often synovial fluids were used as test sample. However, obtaining such a test sample is much more difficult and cumbersome to the patient. Use of the antibodies according to the present invention surprisingly opens up the possibility to reliably detect and draw conclusions from the presence of IL-3 in blood, plasma and serum. Thus, the present invention via its antibodies and their use in diagnosis is a big step forward to relating IL-3 presence to the severity of RA and RA incidents in patients and thus to also determine the supposition of a patient to treatment with IL-3 antibodies.

Test kits which contain antibodies according to the present invention together with other substances for conducting the diagnostic methods of this invention are also a further embodiment of the invention. For determining the presence and amount of IL-3 in body fluids of a patient, such kits can be provided for easy and effective use in laboratories of every size. Test reagents for the various applicable test formats are well known in the art. The inventive contribution to the test kits lies in the presence of antibodies according to the present invention or combinations of antibodies according to the present invention with other IL-3 specific antibodies, most preferably a combination of antibody clones 11 and 13.

As discussed above, especially WO2010/063488 is directed to use of IL-3 inhibitors for the treatment of early stage RA patients. However, also in this context it was not yet clear which kind of inhibitors and which kind of IL-3 antibodies would be especially well suited for a therapeutic application. It seems vital that antibodies used in therapy should not entail drawbacks brought on e.g. by cross-reactivity with other unrelated cytokines or severe immunological responses experienced with known antibodies.

A further subject and embodiment of the present invention therefore is the use of the novel and advantageous antibodies of the invention in a pharmaceutical composition. Such pharmaceutical compositions according to the invention are characterized by the presence of a pharmaceutically effective amount of an antibody or antibody fragment or antibody construct as described herein as an active ingredient. Usual adjuvants and/or carrier substances for pharmaceutical preparations can be included as desired and deemed appropriate.

Pharmaceutical compositions according to the present invention can be used for the treatment or for the prevention and prophylaxis of diseases or malfunctions which are associated with elevated levels or IL-3. As discussed in the introductory part of this specification, IL-3 has a significant growth stimulating and differentiating effect on various hematopoietic precursor cells and is also a growth factor for mast cells. The signal transduction caused by IL-3 has major impact on the immune system. Any disease or medical condition in which IL-3 plays a direct or indirect role in development or progression is a candidate for the treatment by administering the antibodies according to the present invention. Preferably such disease or malfunction connected with elevated levels of IL-3 is related to the immune system, mostly an autoimmune disease and especially RA or acute or chronic graft-versus-host disease and multiple sclerosis.

Further circumstances which are preferably treated by administering the pharmaceutical composition according to the invention is a use in suppressing the activity of human basophils in persons suffering from an allergic reaction and for the stratification of patients having increased IL-3 levels in serum or plasma.

To be eligible for treatment with the pharmaceutical composition of the present invention, in the respective disease or malfunction elevated levels of IL-3 as compared to healthy persons have to be present in any body fluid including synovial fluids but also blood, plasma and serum. The antibodies of the present invention which are contained in the pharmaceutical composition bind specifically to IL-3 and thereby inhibit the activity of IL-3.

Especially in view of RA it has been found that for a large group of patients elevated levels of IL-3 are correlated with the aggravation caused in the patient and the progression of the disease. IL-3 is detected mainly in active RA, whereas patients with a non-active stage of RA usually do not show elevated levels of IL-3. Thus the pharmaceutical compositions of the present invention are especially useful in treating patients with active episodes of autoimmune diseases, as RA, and for the prophylactic treatment to avoid the occurrence of active episodes of the disease.

Since available therapies are only effective in about 50% of treated patients, providing the pharmaceutical compositions according to the invention is a major step to a new and gentle treatment of auto-immune disease in patients. Based on the lack of an overt phenotype of IL-3 deficient mice (Nature. 1998; 392(6671):90-3) and no obvious side effects of mice treated with antibodies against IL-3 (Arthritis Rheum. 2009; 60(5):1352-61) IL-3 targeted treatment should exhibit less severe side effects than currently used pharmaceuticals, especially regarding to infection or neoplasia. In certain cases, it could be desirable to combine treatment with the antibodies and pharmaceutical compositions of the present invention with other medicines like methotrexate or leflunomide. An individualized treatment strategy according to IL-3 levels in plasma, serum or other body fluids, presents an advantage compared to available biologicals, since currently it is not possible to predict reliably, which patient will respond to a specific therapy (including biologicals). Further an individualized approach improves the safety of treatment by reducing the risk of side effects of an ineffective therapy and reduces the costs for treatment of RA.

Also the treatment with the antibodies of the present invention would preferentially be started as soon as elevated IL-3 levels in blood, plasma or serum are detected. Thus, early-on treatment can be applied in patients where RA activity is correlated with elevated IL-3 levels and long term joint damage can be avoided or kept to a minimum. In addition, treatment with anti-IL-3 antibodies would preferentially be started, if patients failed to a previous treatment with DMARDs or biologicals. Further it is expected that the use of the antibodies of the invention can reduce cell infiltration of synovial tissue which can be a further negative factor in the disease pathology.

An effective dose of IL-3 antibody contained in the pharmaceutical composition of the present invention can easily be determined by a physician as generally known in the art. An effective dose is an amount that alleviates the symptoms of the disease or prevents any further progress of the disease or deterioration of the condition of the patient. Progress of disease and condition of the patient can be monitored by determining the IL-3 level and other markers for inflammation or autoimmunity in body fluids, preferably blood, plasma or serum, and by determining other disease scores or using known diagnostic methods. For RA, progress of the disease and the status of the patient can be determined using e.g. the DAS28 activity score. To prevent joint damage a DAS28<=2.6 should be achieved. Effectiveness of a therapy can be measured as the percentage of patients that achieve a certain (e.g. 30%, 50% or 70%) reduction in disease activity. Any decrease of IL-3 or other markers for inflammation in body fluids is also an indication of a successful treatment. Effective doses of the pharmaceutical composition can be determined using dose-response-curves as is well-known to the skilled artisan. The amount of IL-3 present in the body fluids of a patient as determined using the diagnostic methods according to the present invention can also be a basis for determining the effective dose of antibody in the pharmaceutical composition for each patient and the severity of the disease and malfunction.

For the pharmaceutical composition according to the invention and the amount of IL-3 antibody contained therein, dosage further depends on the activity, avidity and the half-life of the antibody. For antibodies having a half-life of about one to two weeks, the dosage is preferably in ta range of 1 to 1000 mg and more preferably 10 to 100 mg per application. The pharmaceutical composition is preferably applied once a day to once a month, again depending on the half-life of the antibody.

Also with regard to a pharmaceutical composition and its use for the treatment of diseases which are correlated with increased IL-3 levels in body fluids, antibody clone 11 is an especially preferred candidate. Antibody clone 11 does not show detectable cross-reaction with GM-CSF and IL-5 and therefore does not influence the activity of these cytokines in the patient (see example 4b). Further it has been shown that clone 11 is very effective in inhibiting the IL-3 dependent growth of human TF-1 cells (see example 5a and 5b), proving an efficient inhibition of the IL-3 activity in patients by this antibody. The growth of TF-1 cells is a well known test system for IL-3 activity and the inhibition thereof. Further, the blocking of the stimulation of basophils is in-vitro evidence for an inhibition of IL-3 activity. Again, clone 11 shows excellent results in view of inhibition of IL-3 activity (see example 5c and 5d). Clone 11 also shows a very high affinity and avidity and already very small amounts of this antibody are sufficient for its inhibitory activity (example 5).

Clone 11 and other antibodies according to the invention showing the characteristics of clone 11 by specifically binding to the 20 amino terminal amino acids of IL-3, especially amino acids 8 to 18 of SEQ ID NO: 1 and most preferably to the sequence motif SWVN (SEQ ID NO: 2), are excellent inhibitors of IL-3 and therefore promising pharmaceuticals with regard to treatment of IL-3 related malfunctions and diseases.

The following examples and figures further illustrate and describe the present invention but are not intended to limit the scope thereof.

FIG. 1 shows the amino acid sequence homology of IL-3 of various species;

Figure 3:
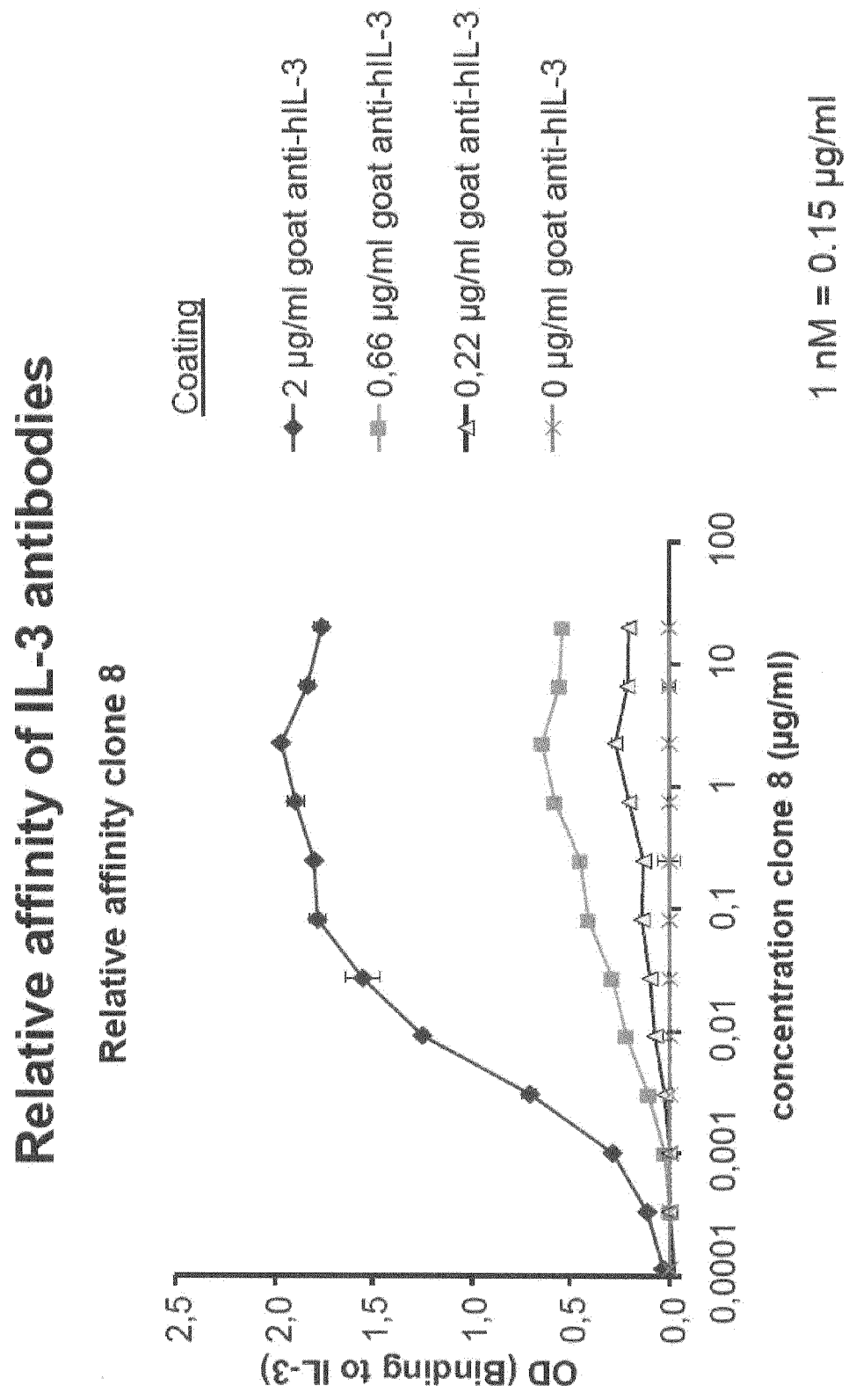
Figure 4:
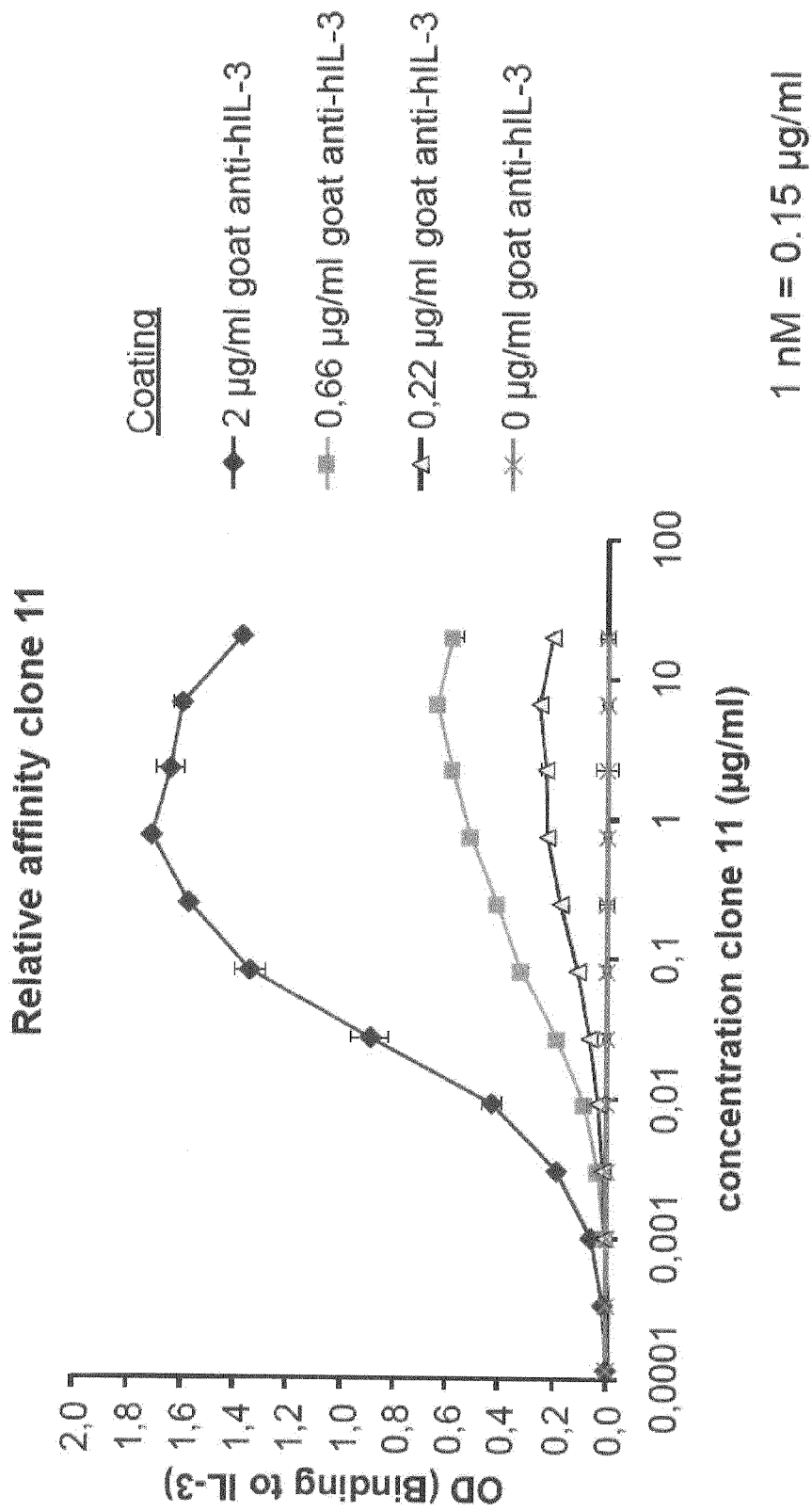

FIGS. 3 and 4 show the relative affinity of antibodies clone 8 and clone 11 for IL-3 as determined by using varying amounts of the antibodies in ELISA assays for which different amounts of IL-3 were bound via goat anti-human-IL-3 antibodies to a solid surface via increasing amounts of coated goat anti-hIL-3 antibody.

Figure 5:
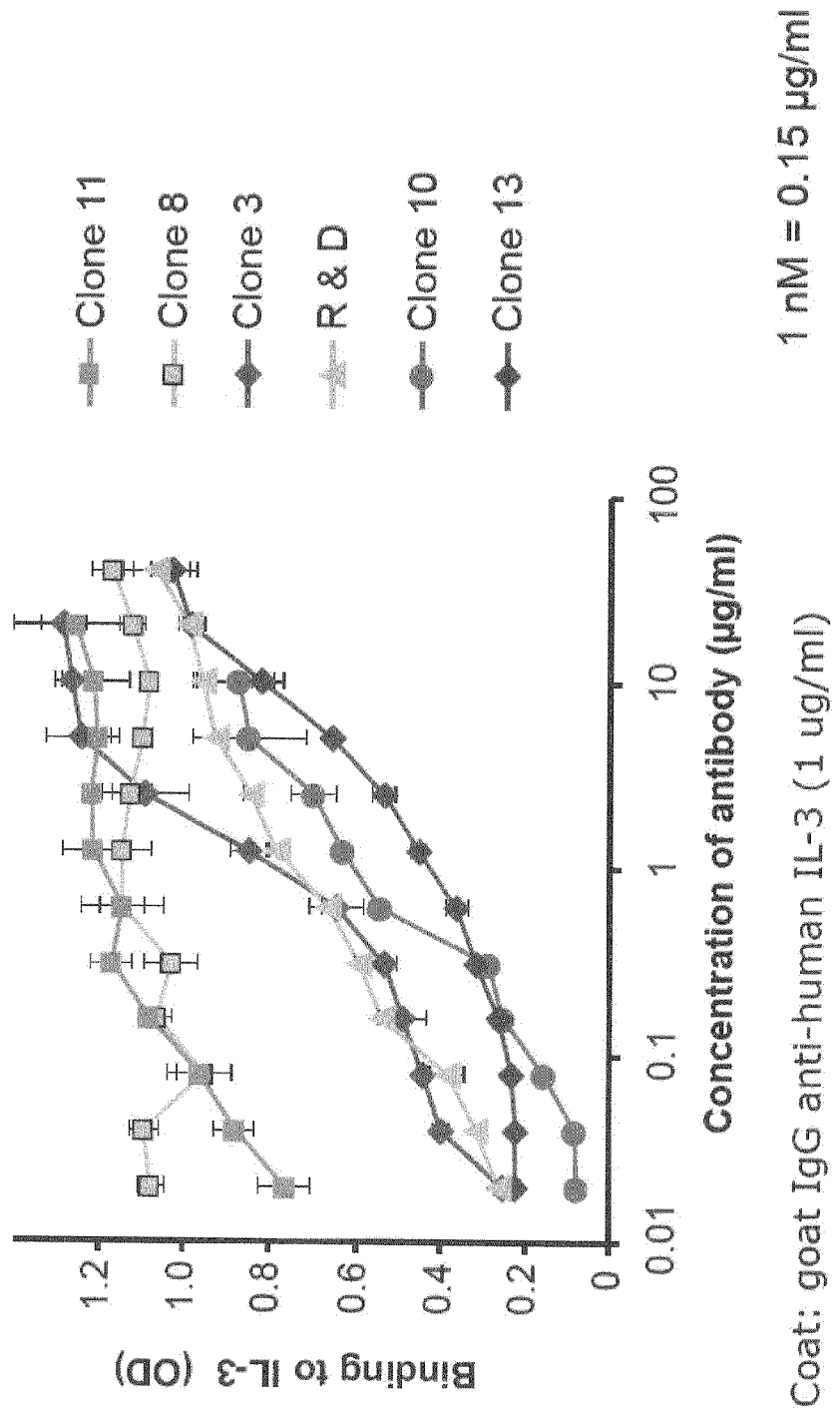

FIG. 5 shows the relative IL-3 affinity of antibodies determined using varying concentrations of antibodies at a constant amount of IL-3 which was bound to the solid phase in an ELISA assay.

Figure 6:
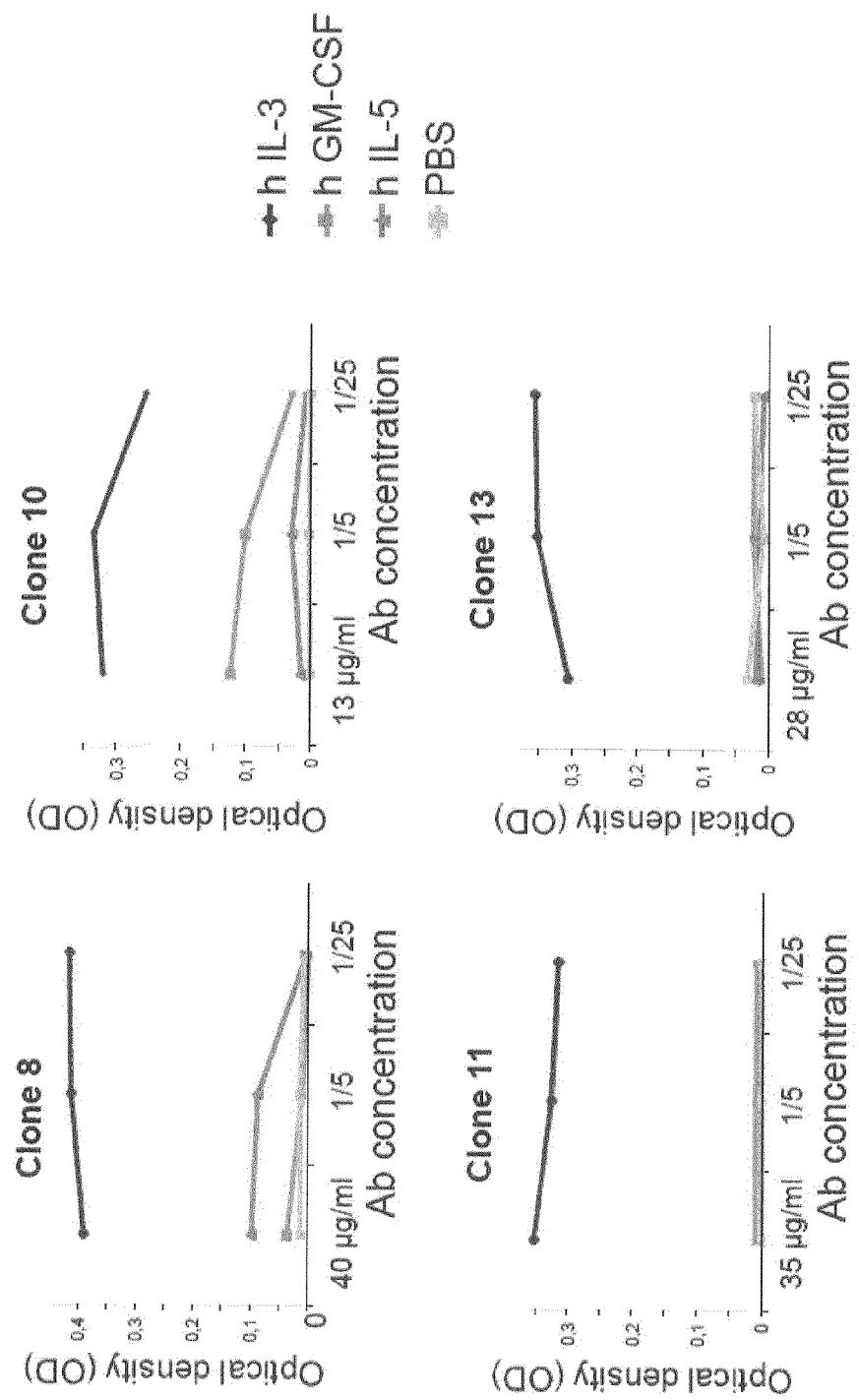

FIG. 6 shows the results of tests performed to detect a possible cross-reactivity of anti-IL-3 antibodies with other human cytokines. In the tests, binding of the antibodies to IL-3, GM-CSF and IL-5 was compared.

Figure 7:
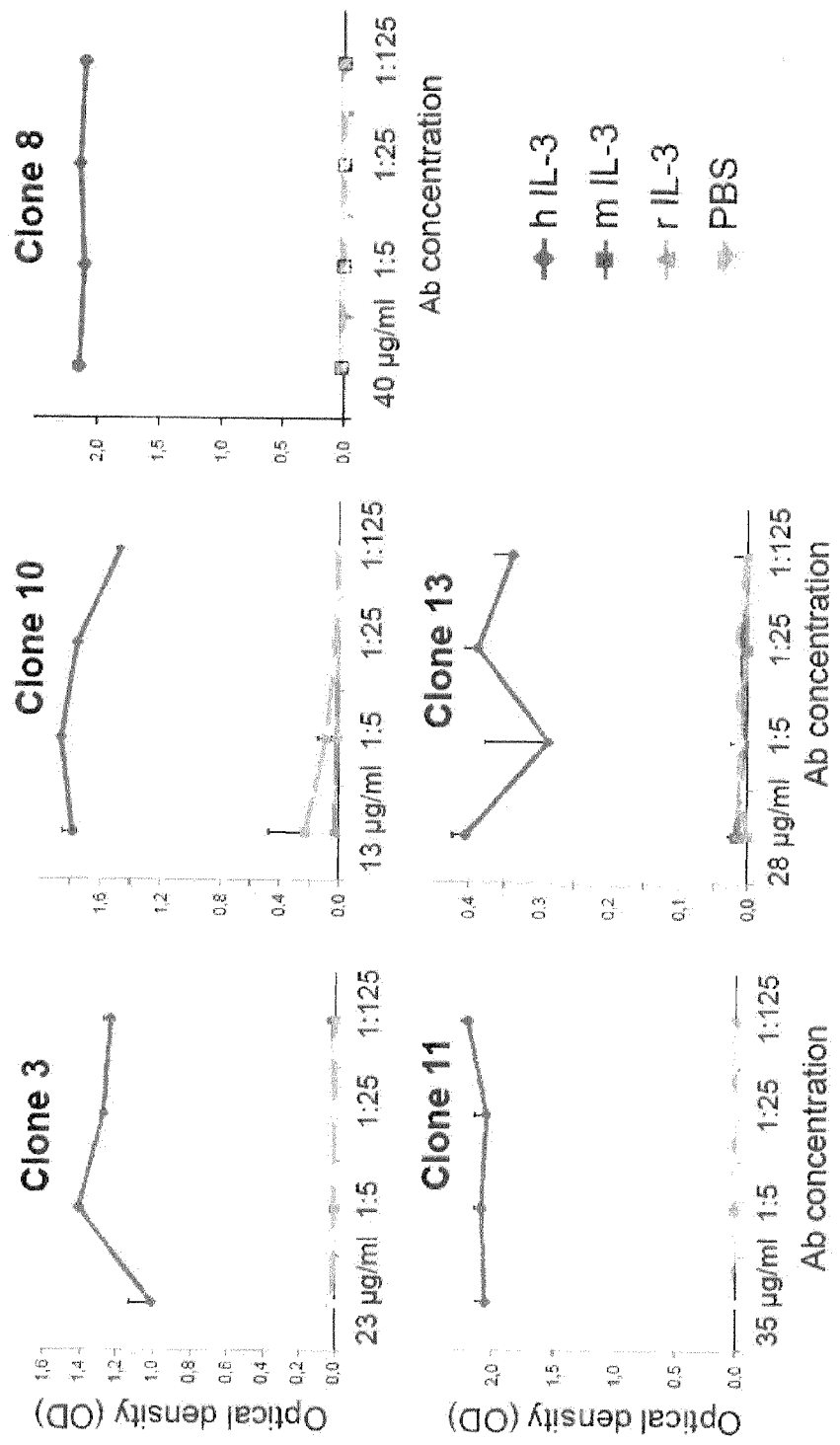
Figure 8:
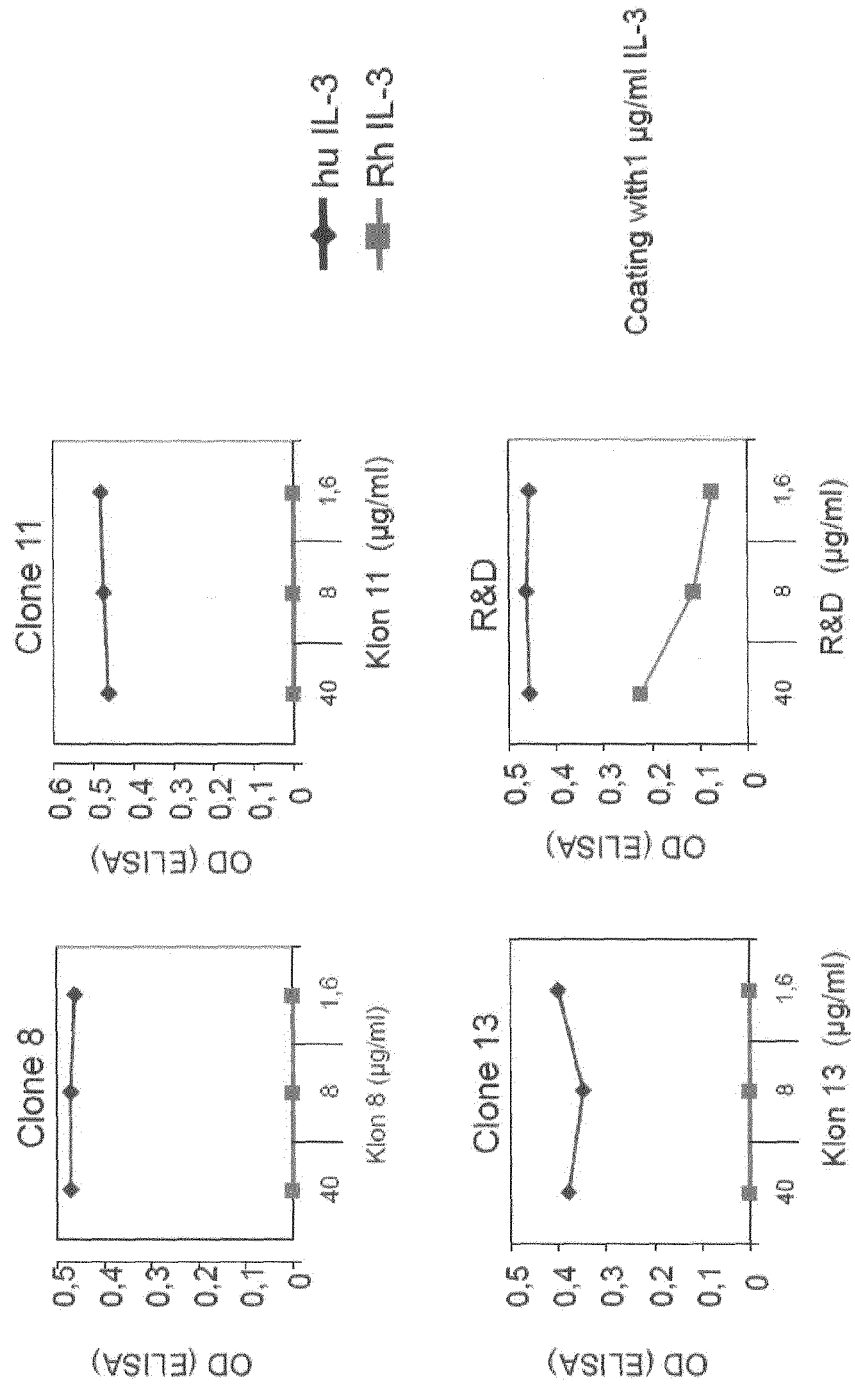

FIGS. 7 and 8 show the results of tests performed to detect possible cross-reactivity of the various anti-IL-3 antibodies with IL-3 from other species. In the test depicted in FIG. 8, also a commercially available anti-IL-3 antibody was included.

Figure 9:
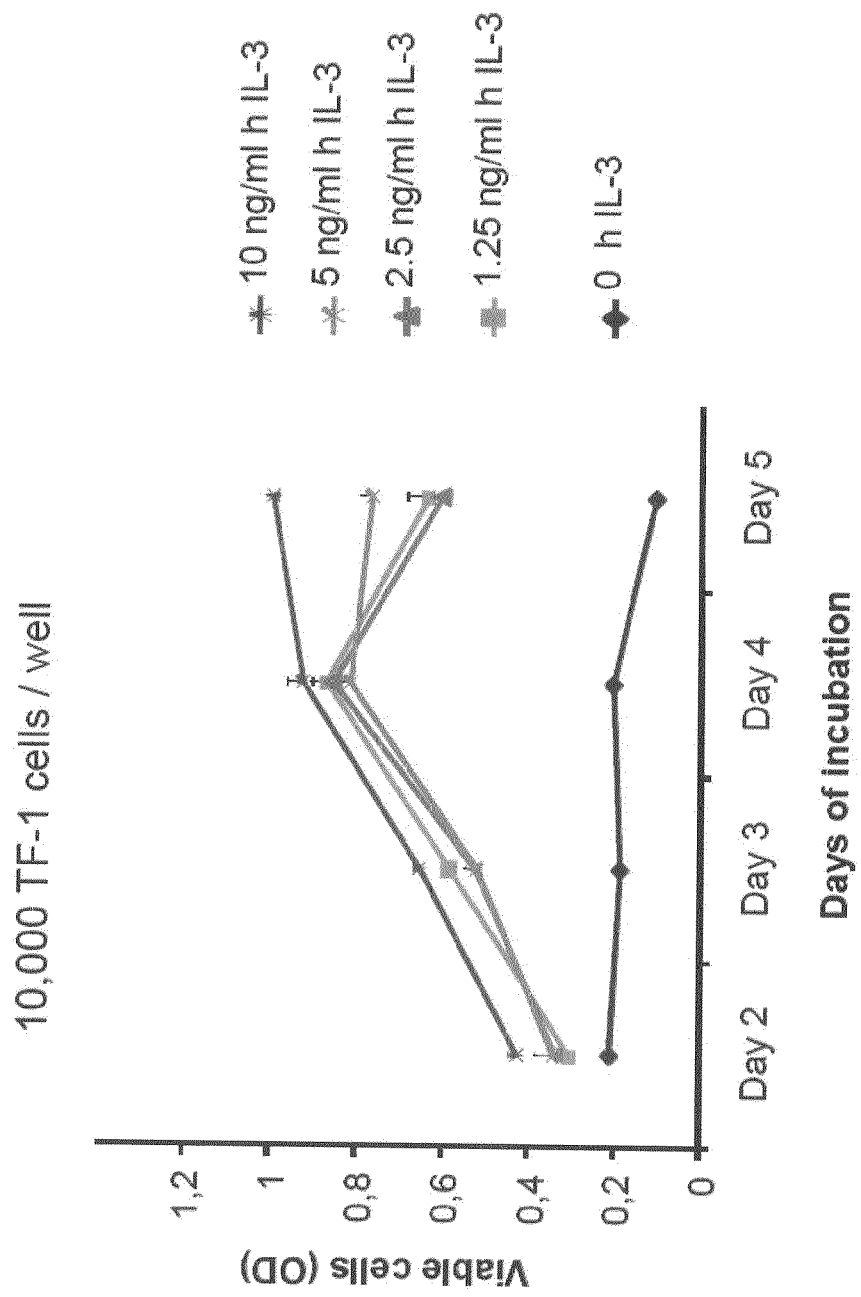
Figure 10:
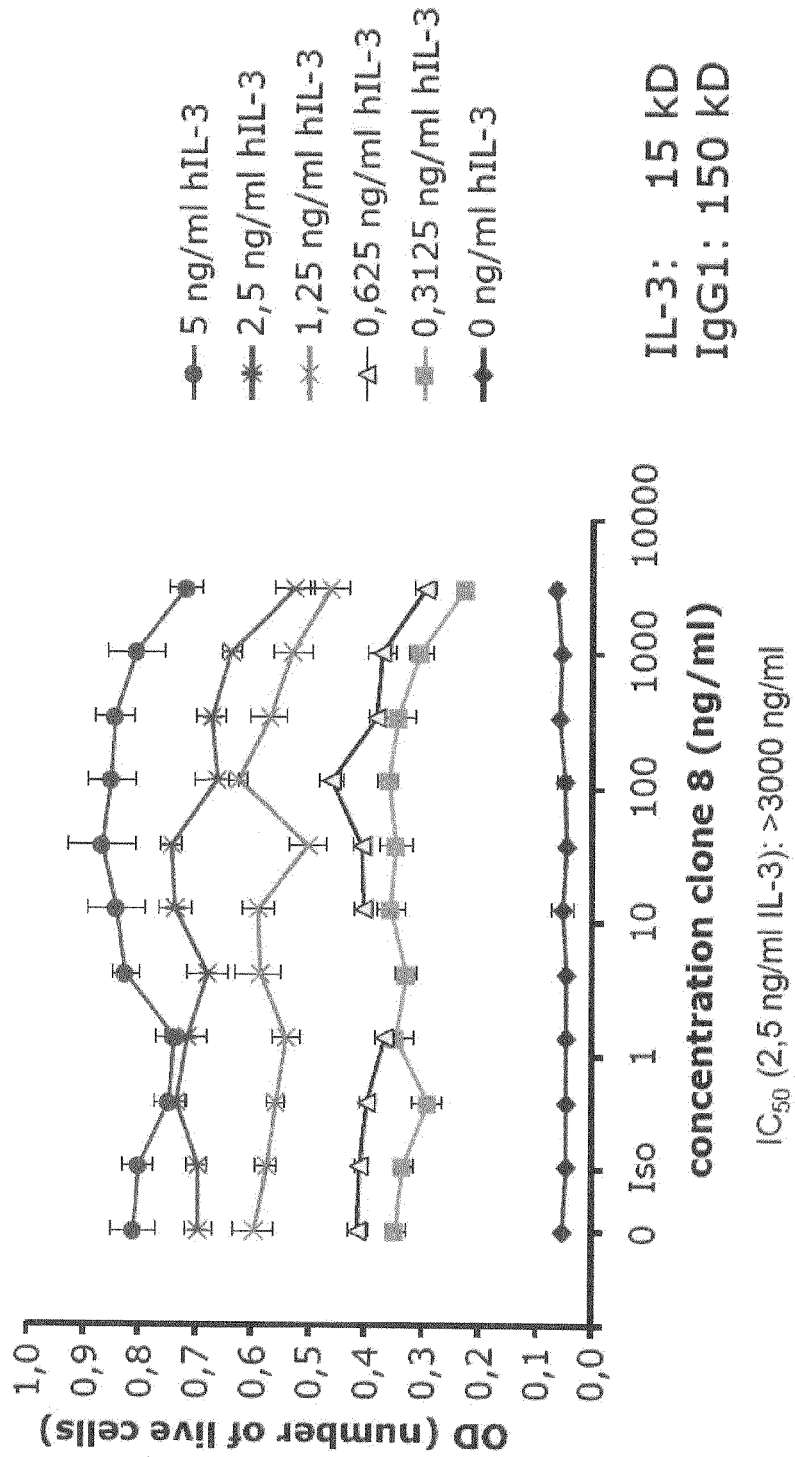
Figure 11:
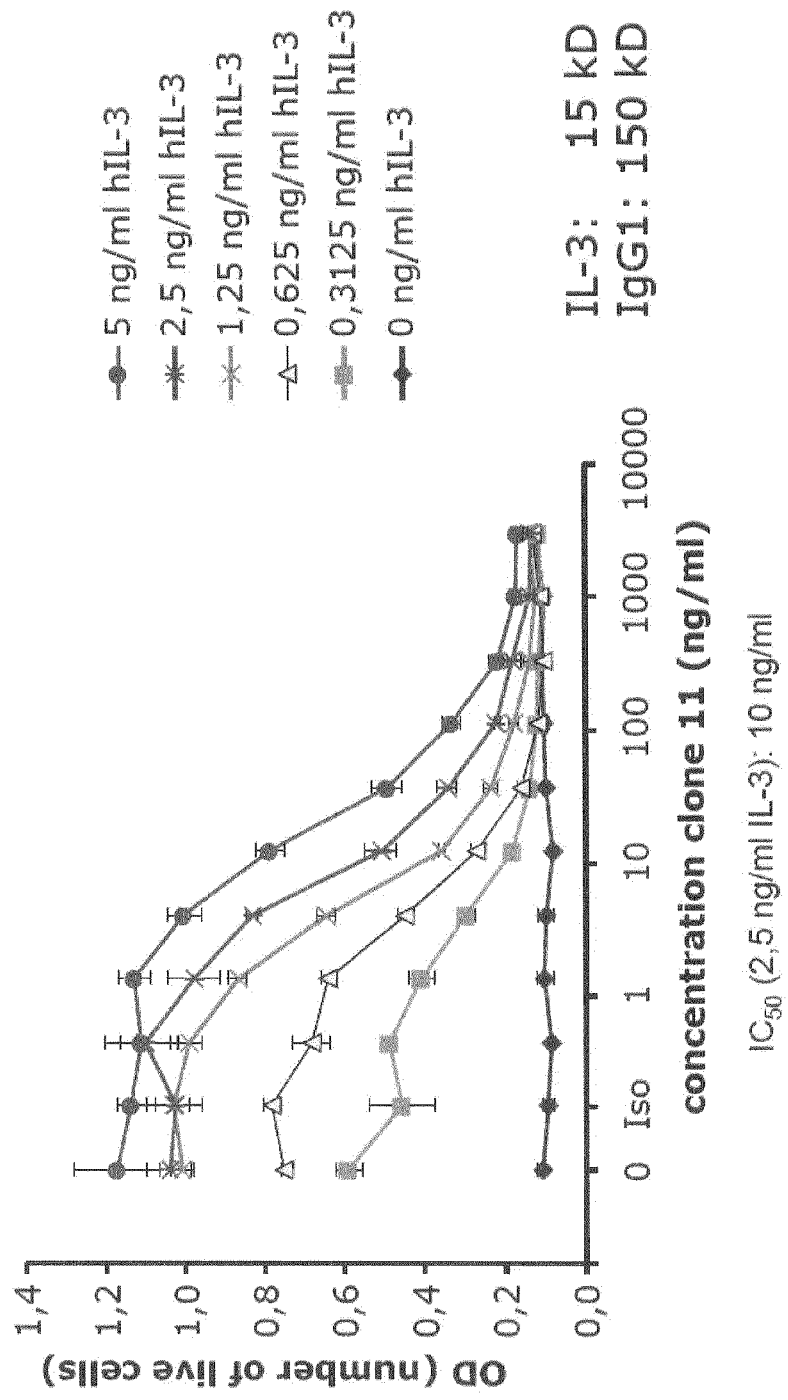
Figure 12:
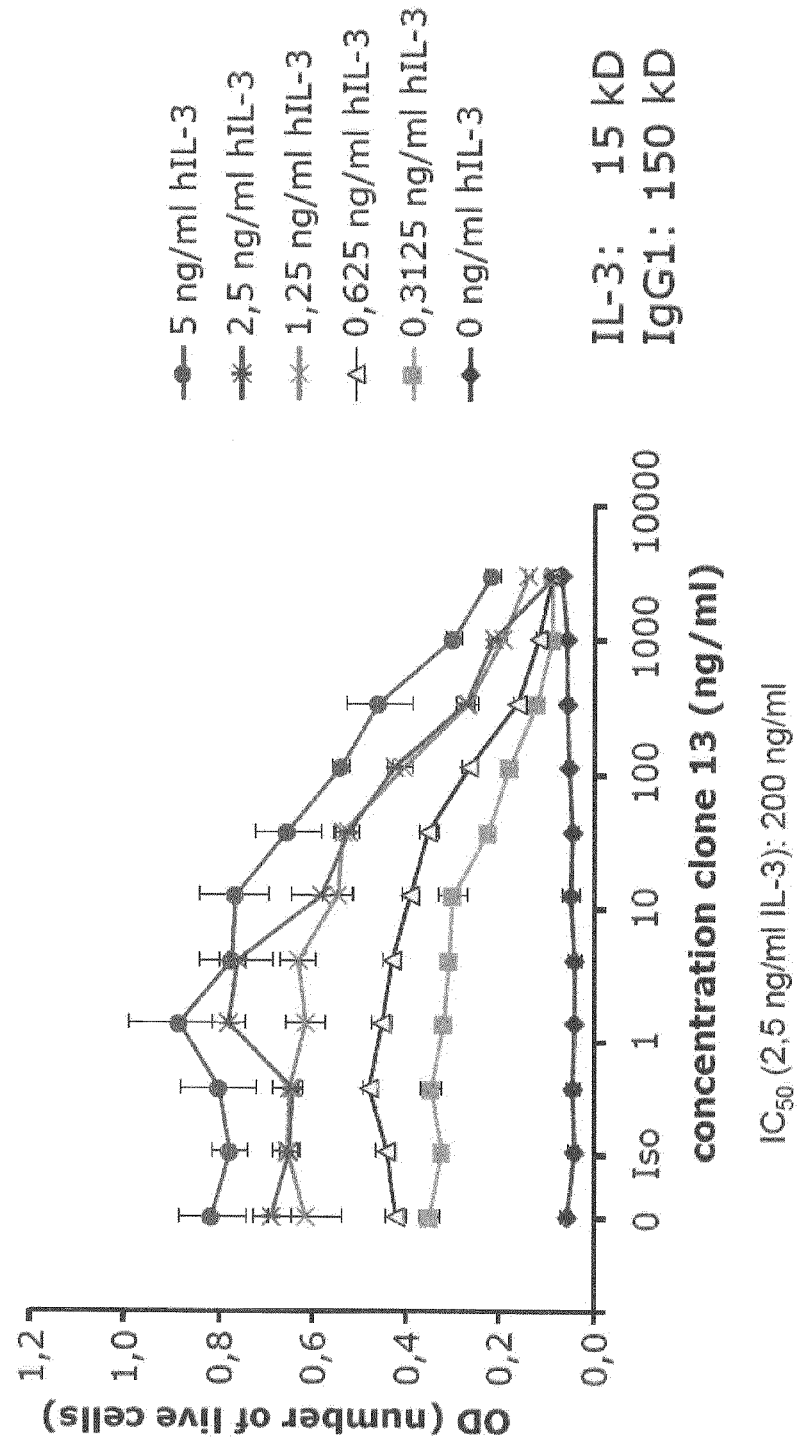
Figure 13:
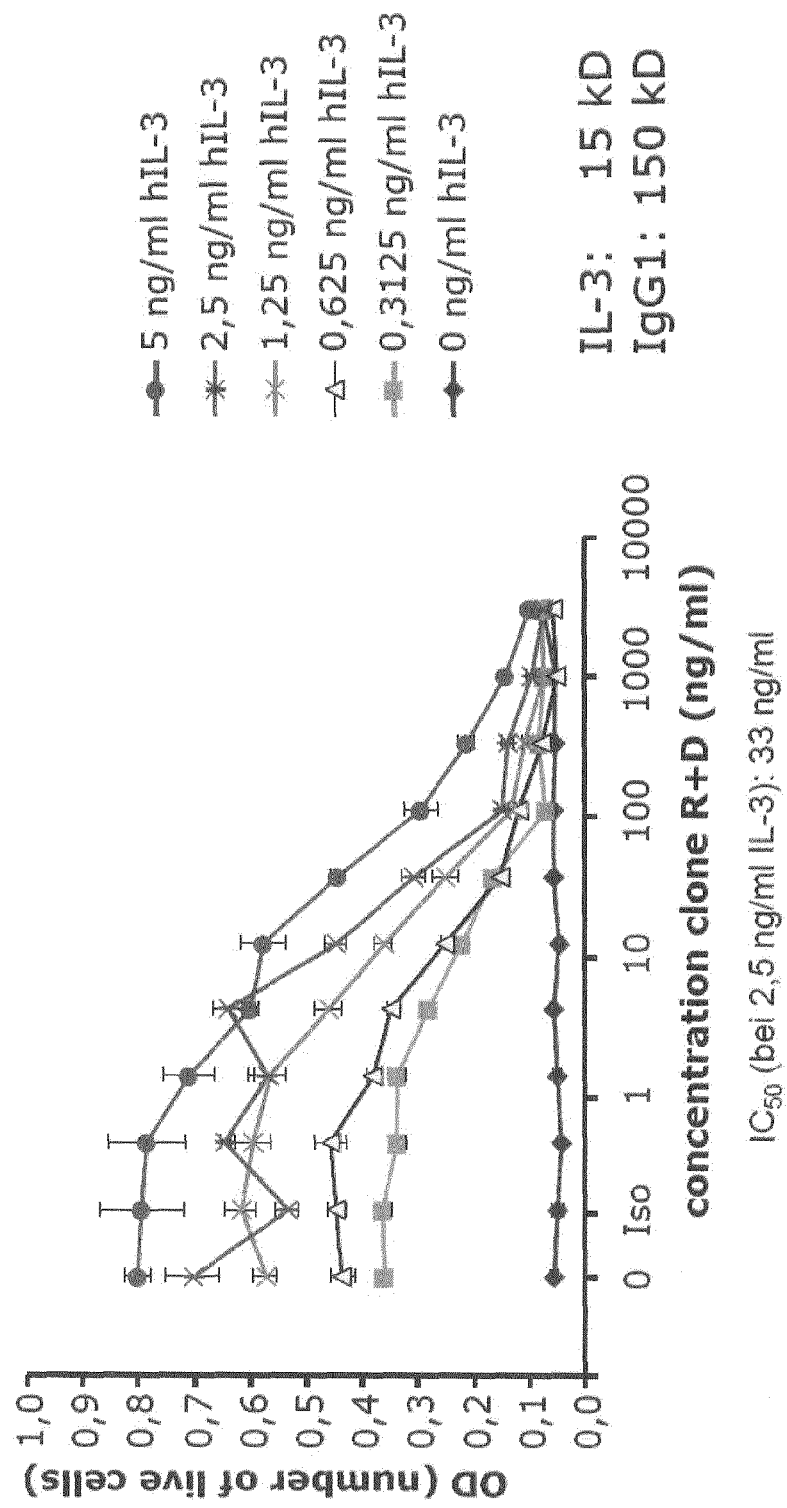

FIG. 9 shows the IL-3 dependent growth of TF1 cells wherein viable cells do not propagate in the absence of IL-3 and cell growth can be shown to be dependent on the amount of IL-3 in the growth medium.

FIGS. 10 to 13 show the ability of various monoclonal antibodies—including a commercially available anti-IL-3 antibody—to inhibit the IL-3 dependent growth of TF1 cells. For differing concentrations of hIL-3 present in the cell growth medium, the effect of the antibodies was tested showing distinct inhibition of cell growth for antibodies clone 11, clone 13 and the commercially available R&D anti-IL-3 antibody, whereas clone 8 had only a minor effect.

Figure 14:
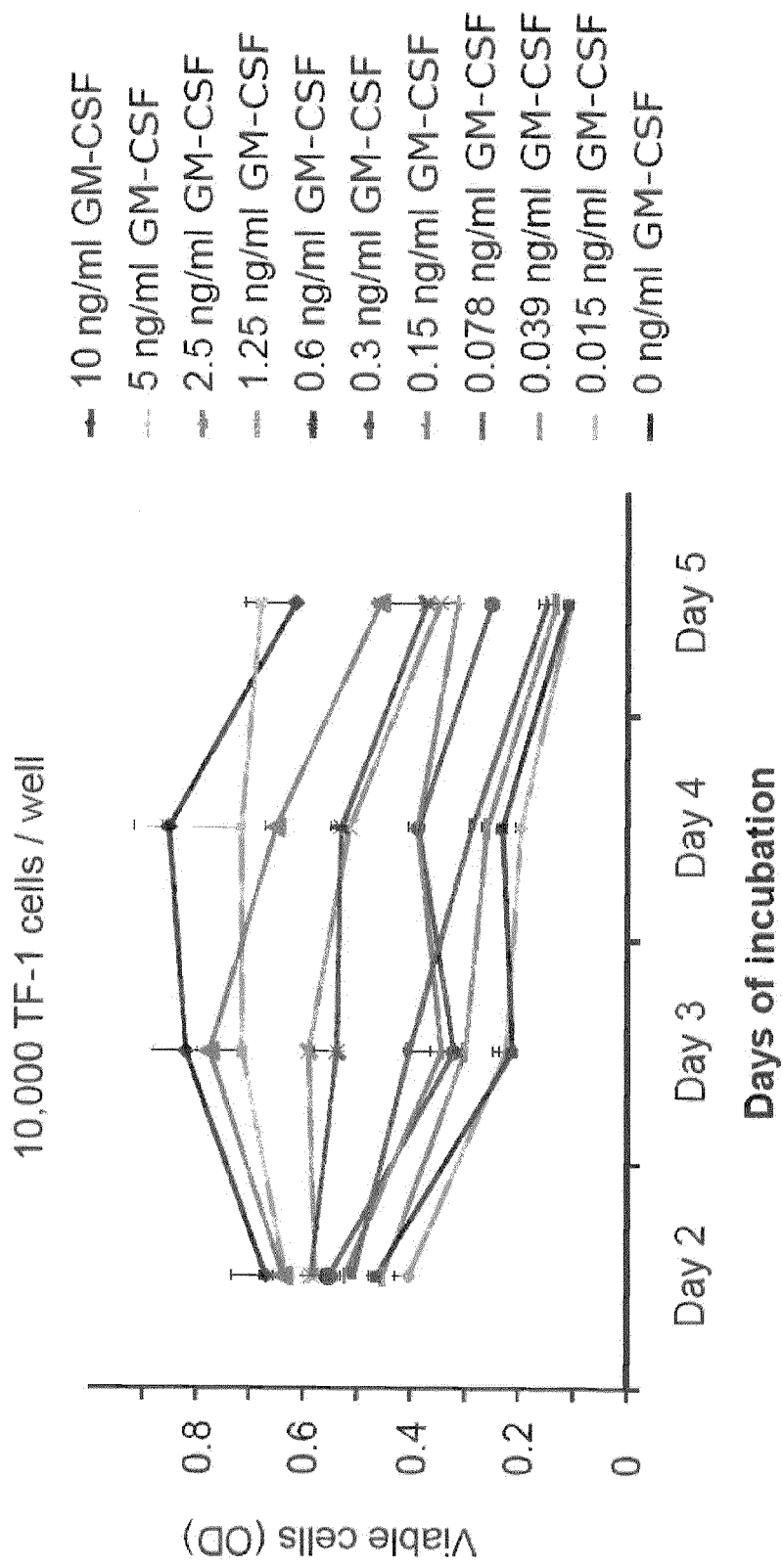

FIG. 14 shows the GM-CSF dependent growth of TF1 cells wherein viable cells do not propagate in the absence of GM-CSF and IL-3. Either one of these cytokines is necessary for growth and propagation of TF1 cells.

Figure 15:
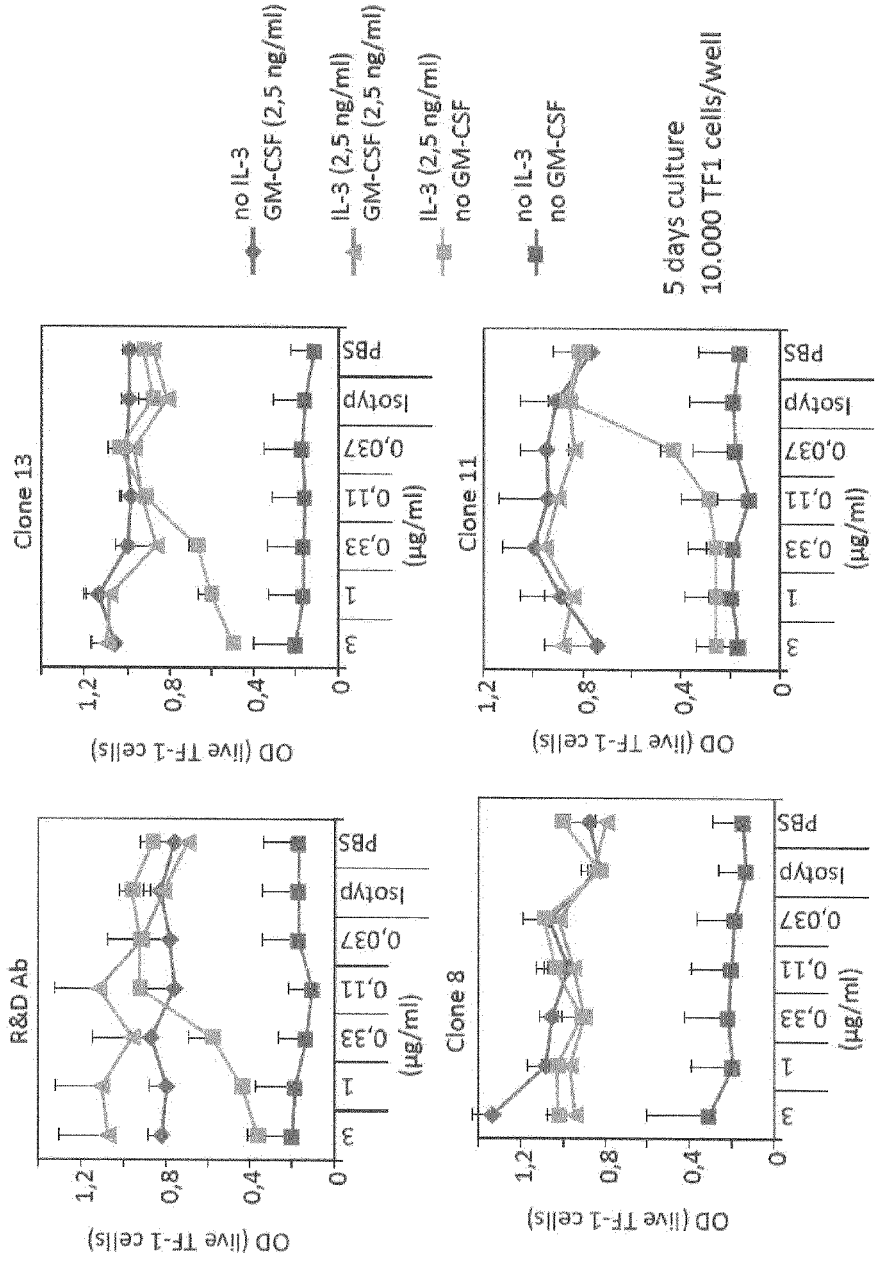

FIG. 15 shows the effect of various antibodies (clone 8, clone 11, clone 13 and R&D) and different concentrations thereof in the medium on the growth of TF1 cells in the presence of IL-3, GM-CSF or a combination thereof, or in the absence of these cytokines. None of the antibodies showed a marked inhibitory effect on the growth of TF1 cells in the presence of GM-CSF whereas, again, clone 11 and at a higher concentration also clone 13 and the R&D antibody clearly inhibited the IL-3 effect on the growth of TF1 cells.

Figure 16:
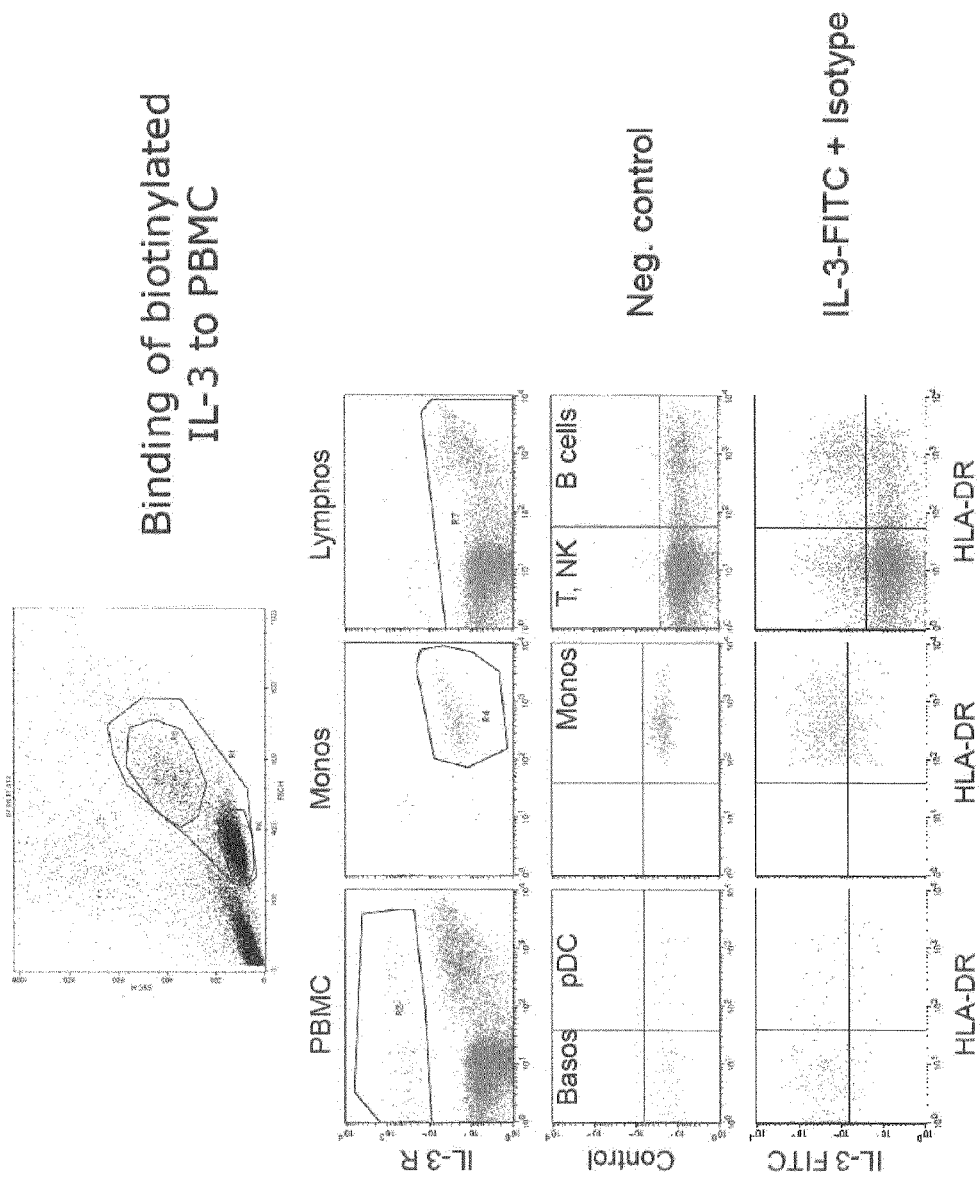

FIG. 16 shows the binding of biotinylated IL-3 to peripheral mononuclear blood cells as well as to monocytes and lymphocytes as compared to a negative control. Basophils were identified by high expression of CD123 and absence of HLA-DR. Plasmacytoid dendritic cells (pDC) were identified by high expression of CD123 and HLA-DR. Monocytes and B cells were identified by light scatter properties and expression of HLA-DR.

Figure 17:
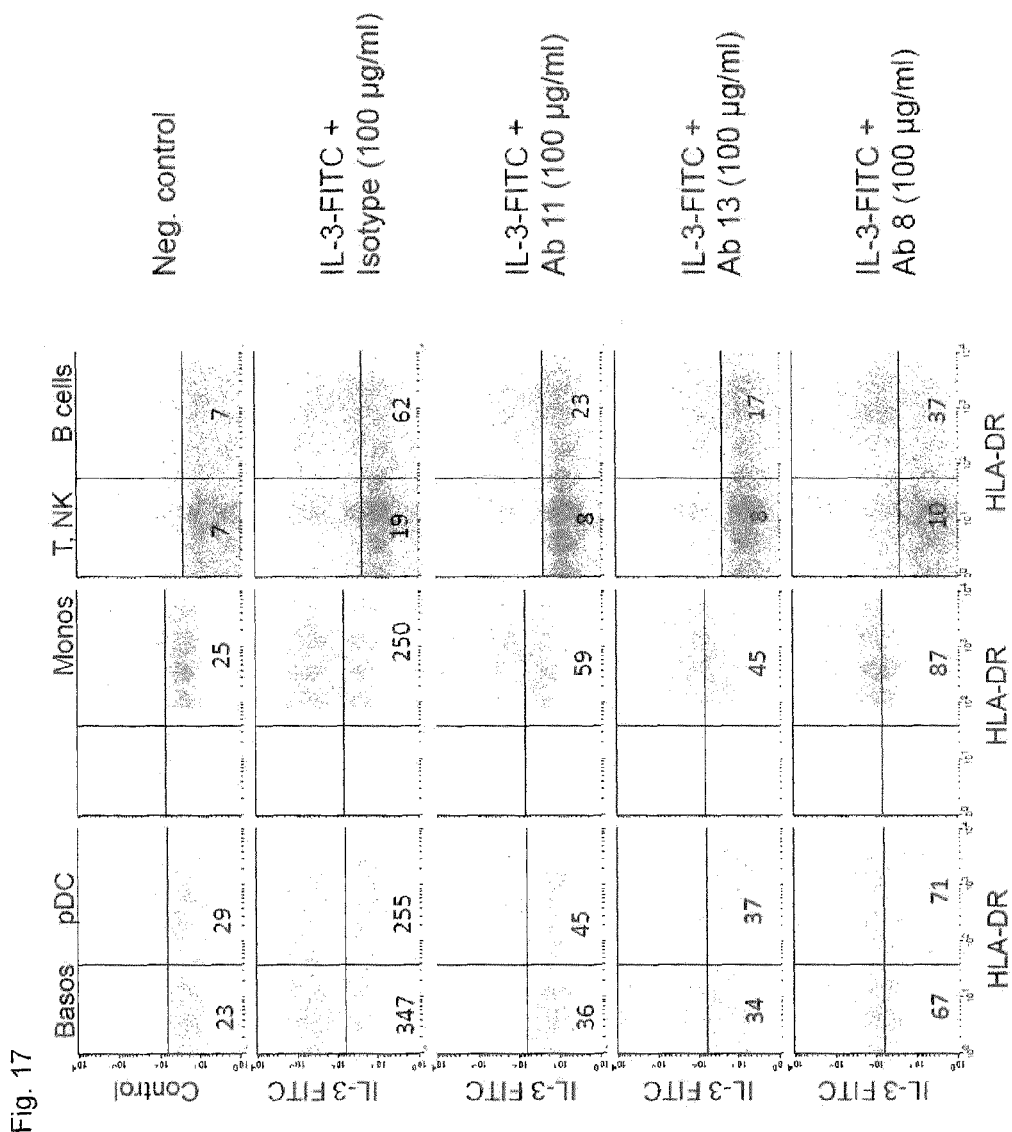
Figure 18:
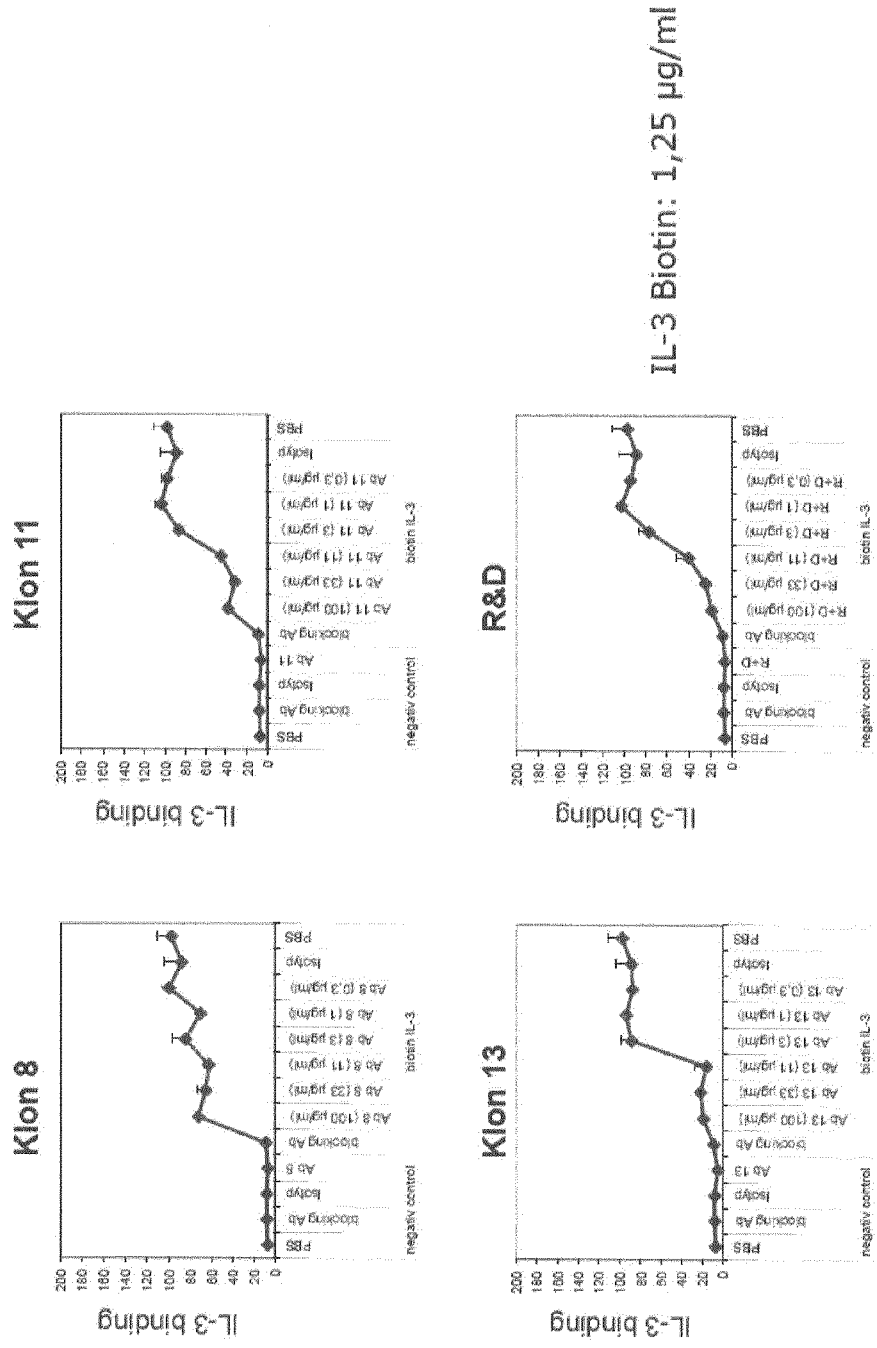
Figure 19:
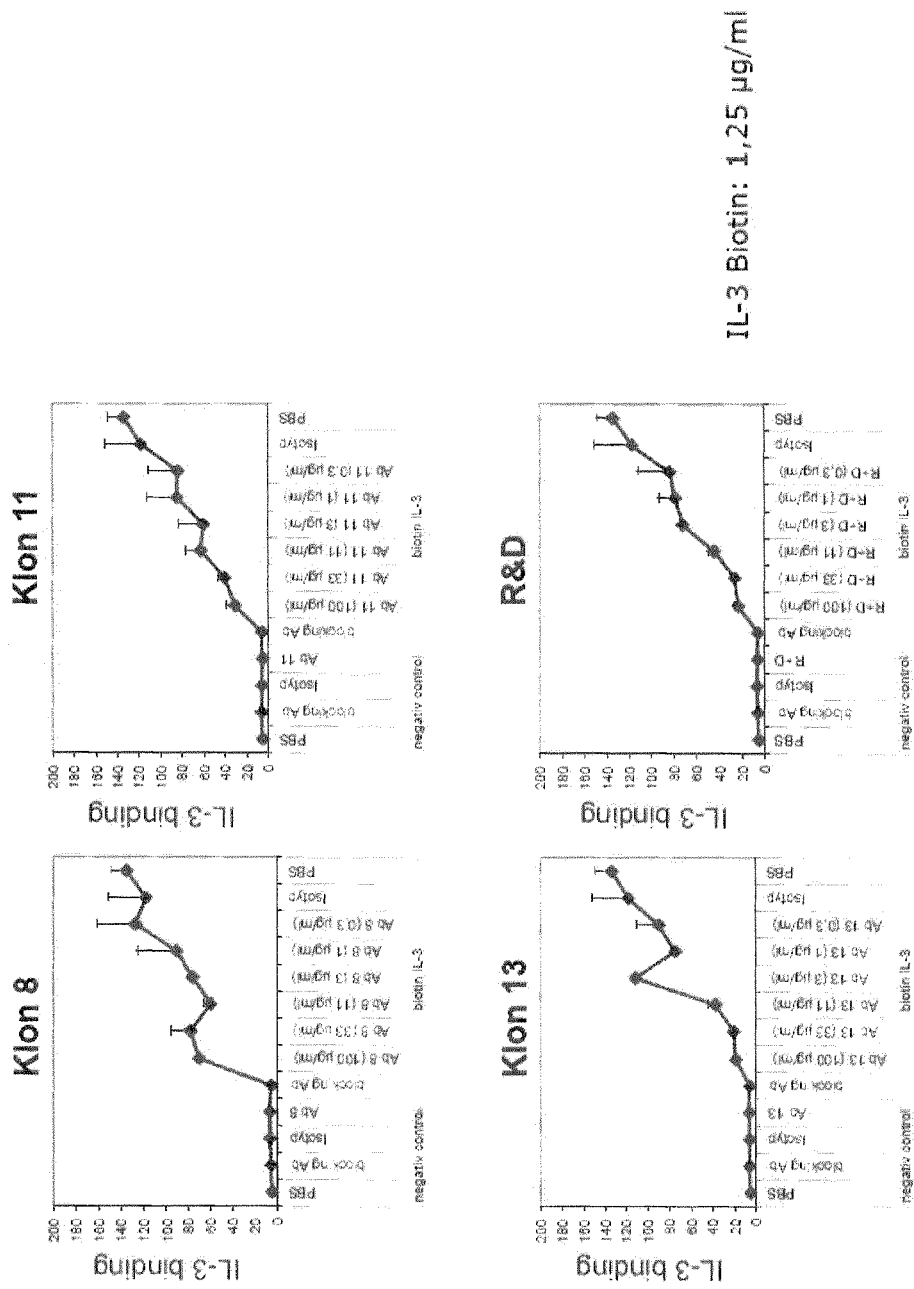
Figure 20:
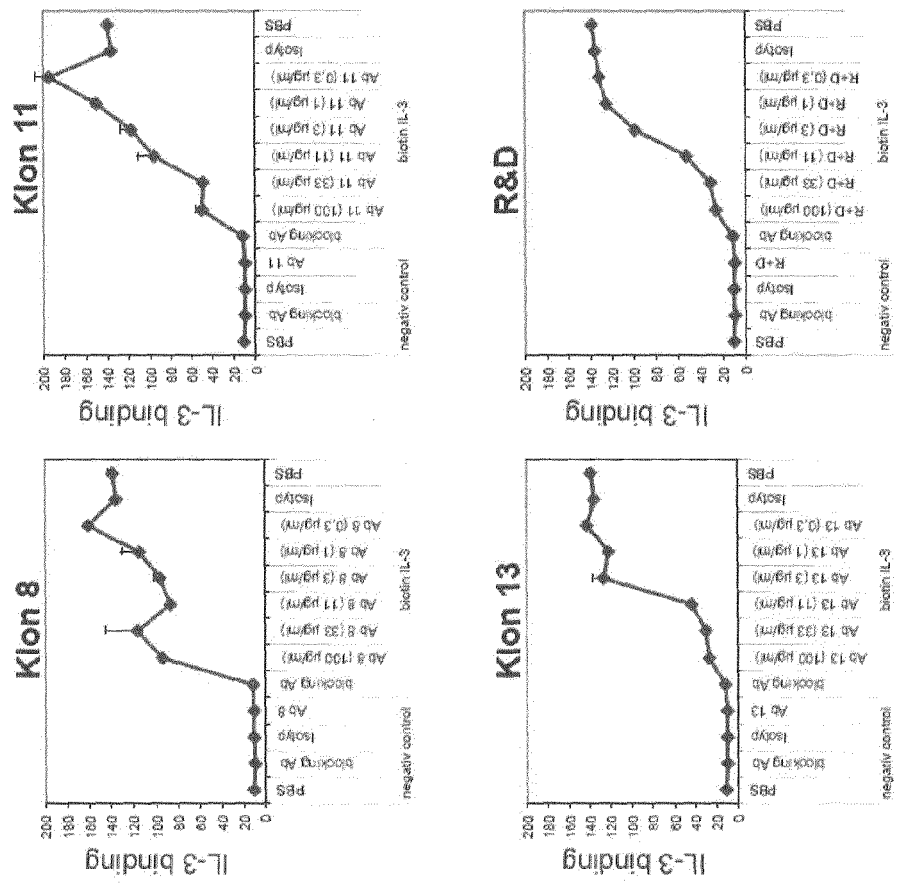

FIG. 17 shows the inhibiting effect of antibodies clone 8, clone 11, clone 13 as compared to a negative control and isotype antibody as a positive control with regard to binding of IL-3 to IL-3 receptors on Basophils, pDC, monocytes and B cells. It can be seen that clones 11 and 13 have a clear inhibitory effect on the binding of IL-3 to IL-3 receptors on these cells, whereas clone 8 had nearly no effect at all.

Figure 21:
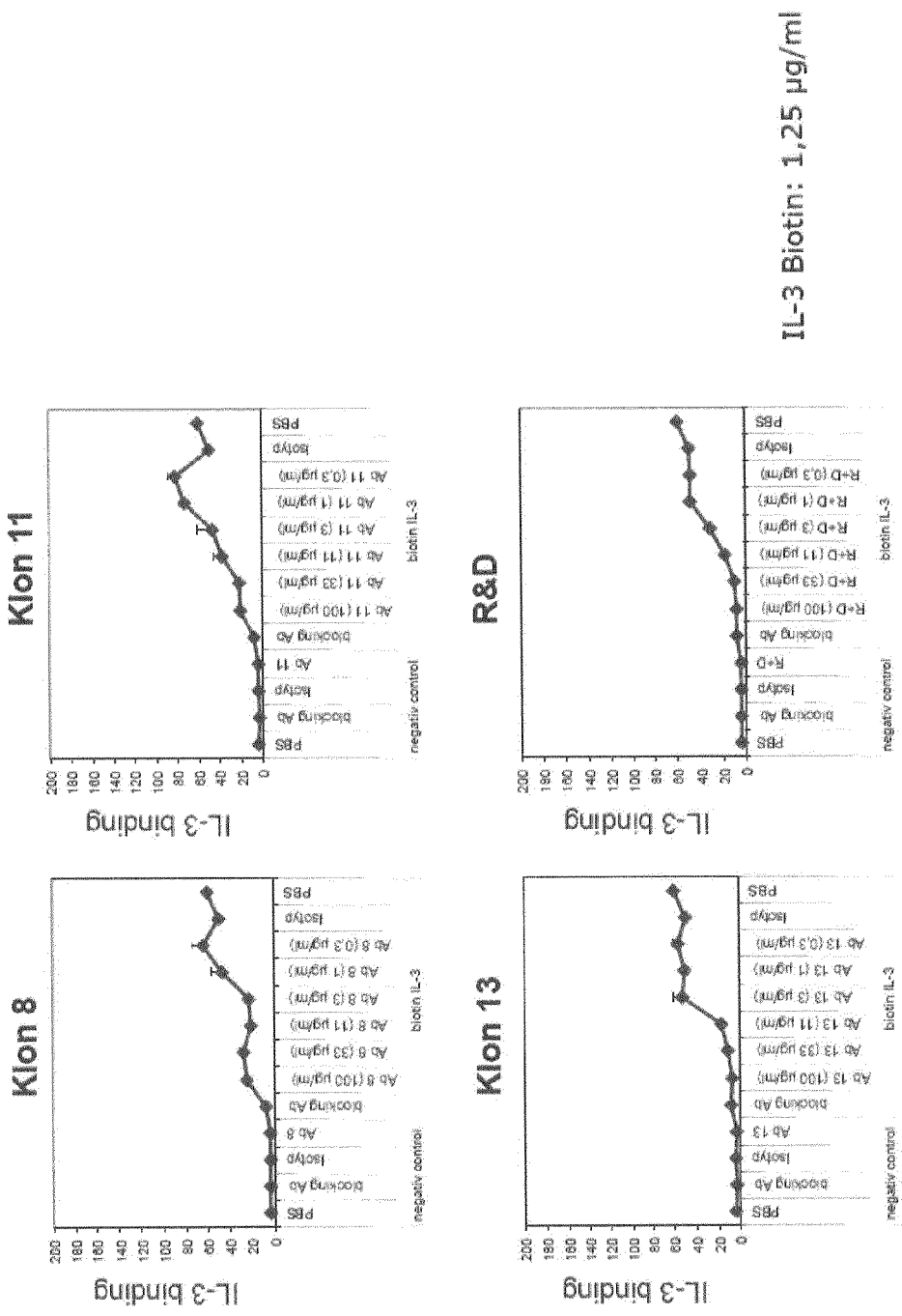

FIGS. 18 to 21 show the inhibitory effect of different amounts of antibody (clones 8, 11, 13 and the commercially available R&D anti-IL-3 antibody) on the binding of biotinylated IL-3 to basophils (FIG. 18), plasmocytoid dendritic cells pDC (FIG. 19), monocytes (FIG. 20) and B-cells (FIG. 21). Clear and strong inhibition of the binding of IL-3 to all cell types was effected by clones 11, 13 and R&D, whereas clone 8 had a much weaker effect, if any.

FIG. 22 shows the results of a FACS analysis for a detection of the stimulation marker CD203c after stimulation of basophils at different time intervals.

Figure 24:
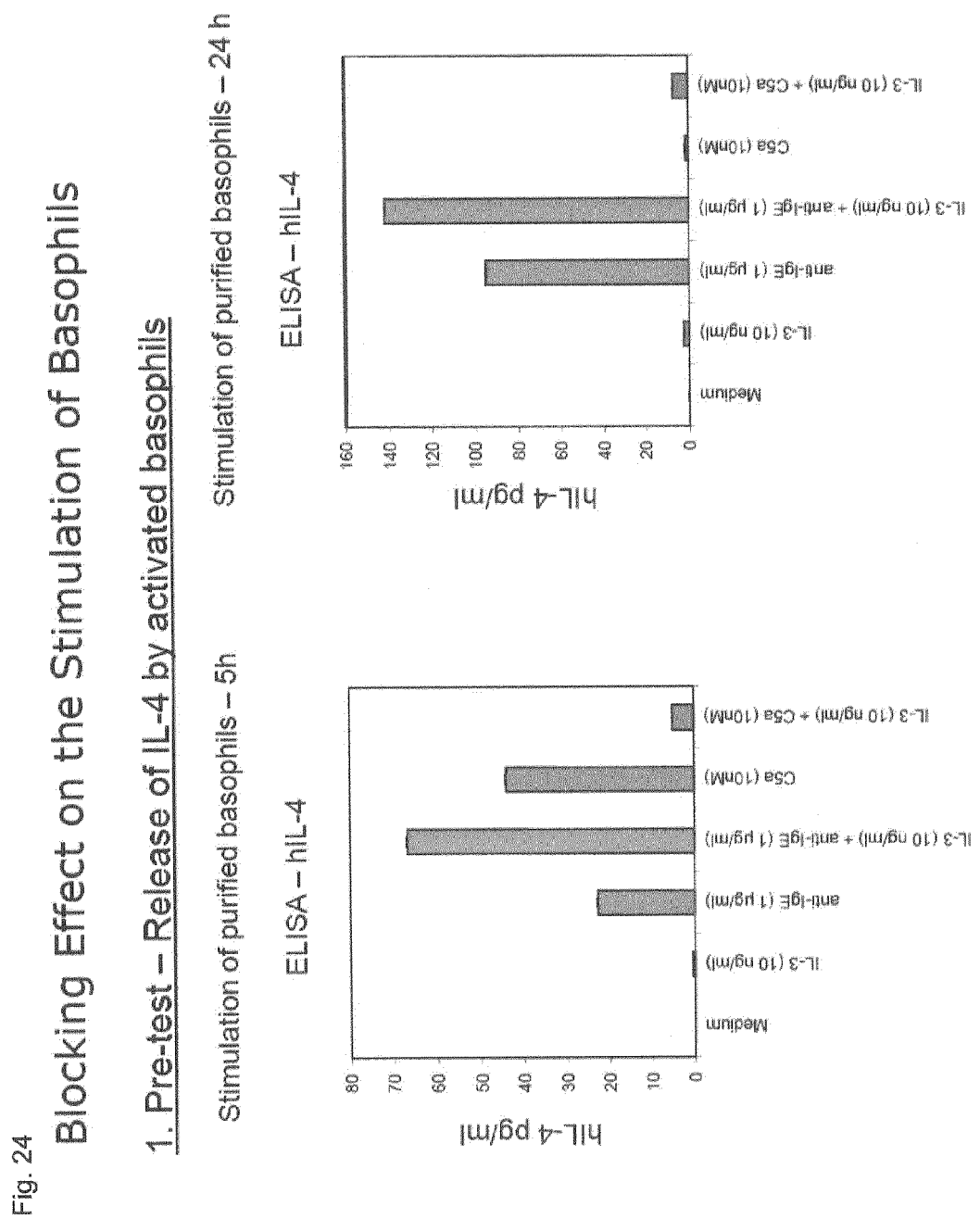

FIG. 23 shows the results of an ELISA assay for detecting IL-13, FIG. 24 shows the results of an ELISA assay for detecting hIL-4 both of which are present in response to a stimulation of basophils over different time intervals.

Figure 25:
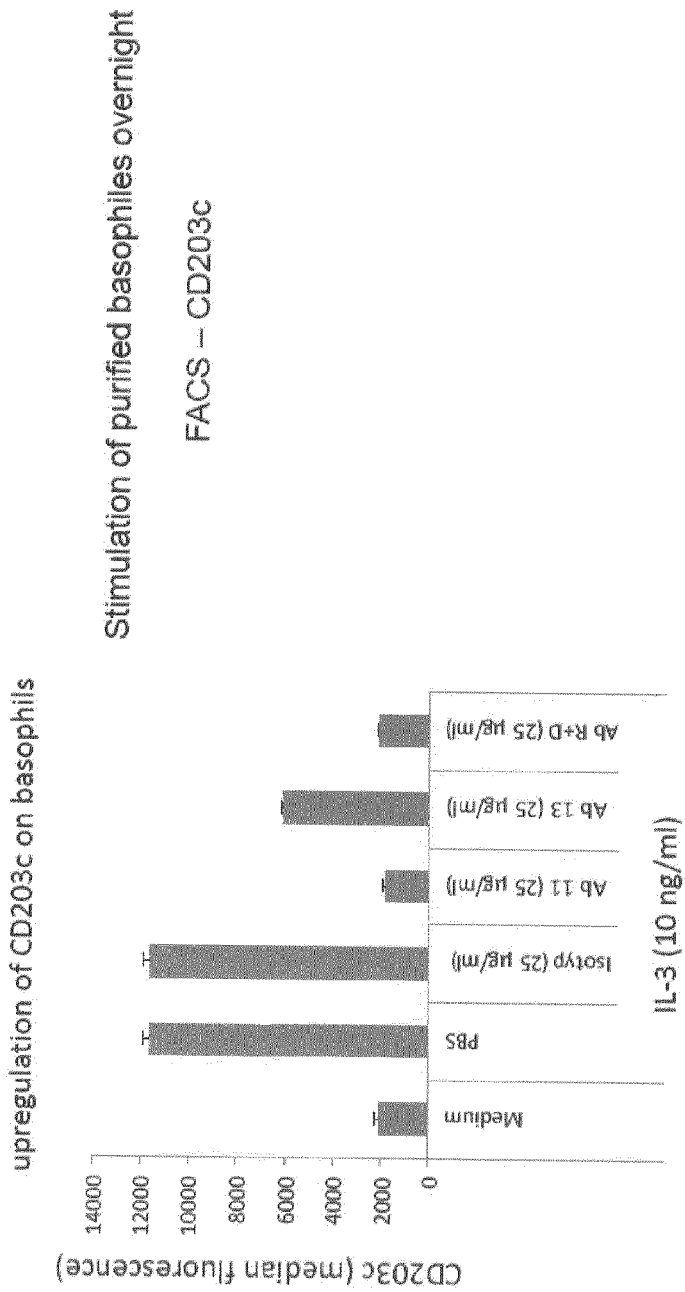

FIG. 25 shows the results of a FACS analysis for detection of the stimulation marker CD203c upon addition of IL-3 and IL-3 preincubated with antibody clones 11, 13 and the commercially available R&D anti-IL-3 antibody. The results indicate a strong inhibitory effect on the upregulation of CD203c in basophils for clones 11 and for the R&D antibody, only a much smaller inhibiting effect was observed for clone 13.

Figure 26:
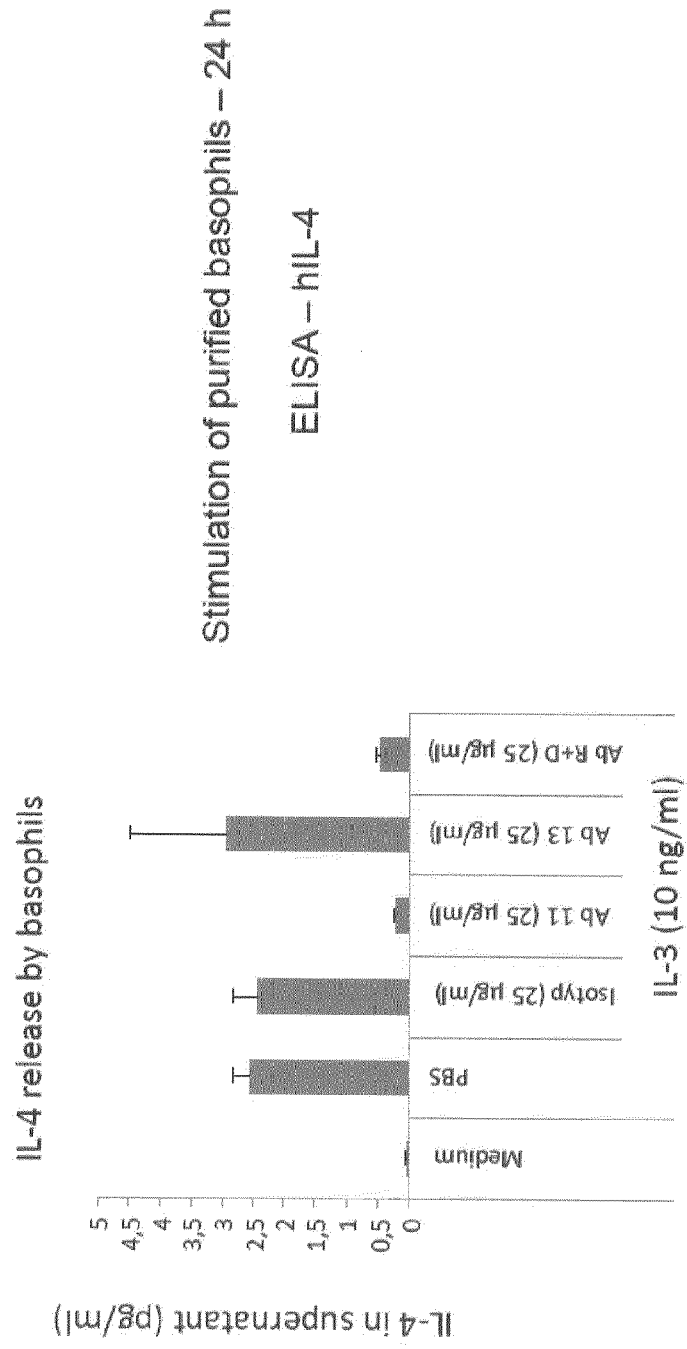

FIG. 26 shows the results of an ELISA assay for detecting hIL-4 after stimulation of basophils with IL-3 and IL-3 preincubated with antibodies. In the test, again, antibody clone 11 and the R&D antibody had a remarkable inhibitory effect on the IL-4 release in basophils, whereas clone 13 did not show any effect.

Figure 27:
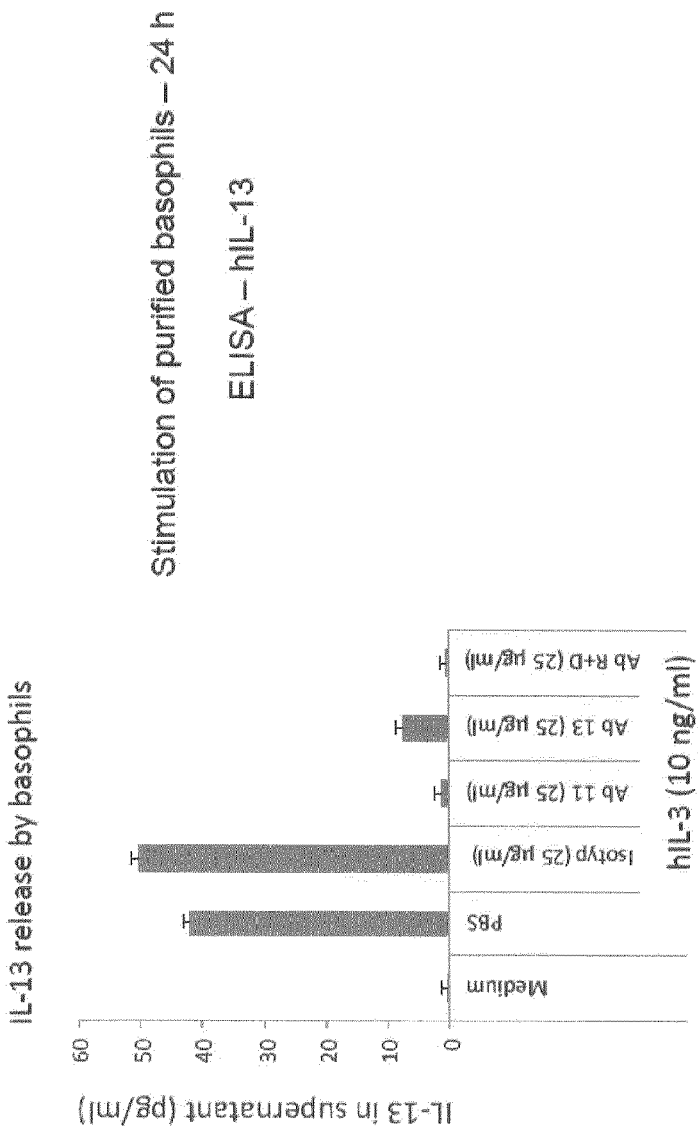

FIG. 27 shows the results of an ELISA assay for detecting hIL-13 after stimulation of basophils with IL-3 and IL-3 preincubated with antibodies. In this test, all three antibodies clone 11, clone 13 and R&D showed strong inhibition of IL-13 formation in the cells.

FIG. 28 shows six peptides (SEQ ID NOs: 3-8) which were used for an epitope mapping with regard to highly specific and affine hIL-3 antibodies. To this end, overlapping peptides were created that together cover the complete human IL-3 sequence. The peptides were coated onto solid surfaces and used in ELISA assays to detect specifically binding monoclonal antibodies.

Figure 29:
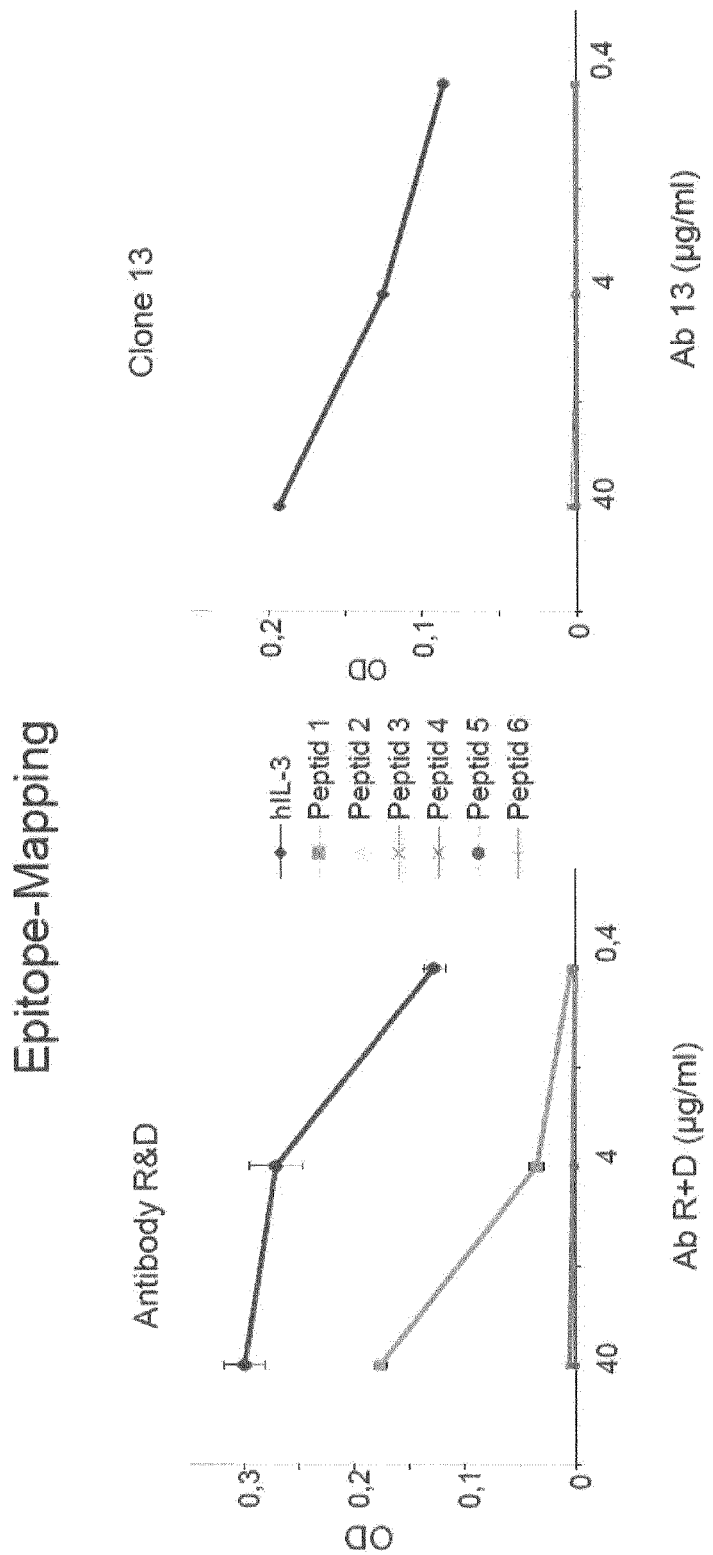
Figure 30:
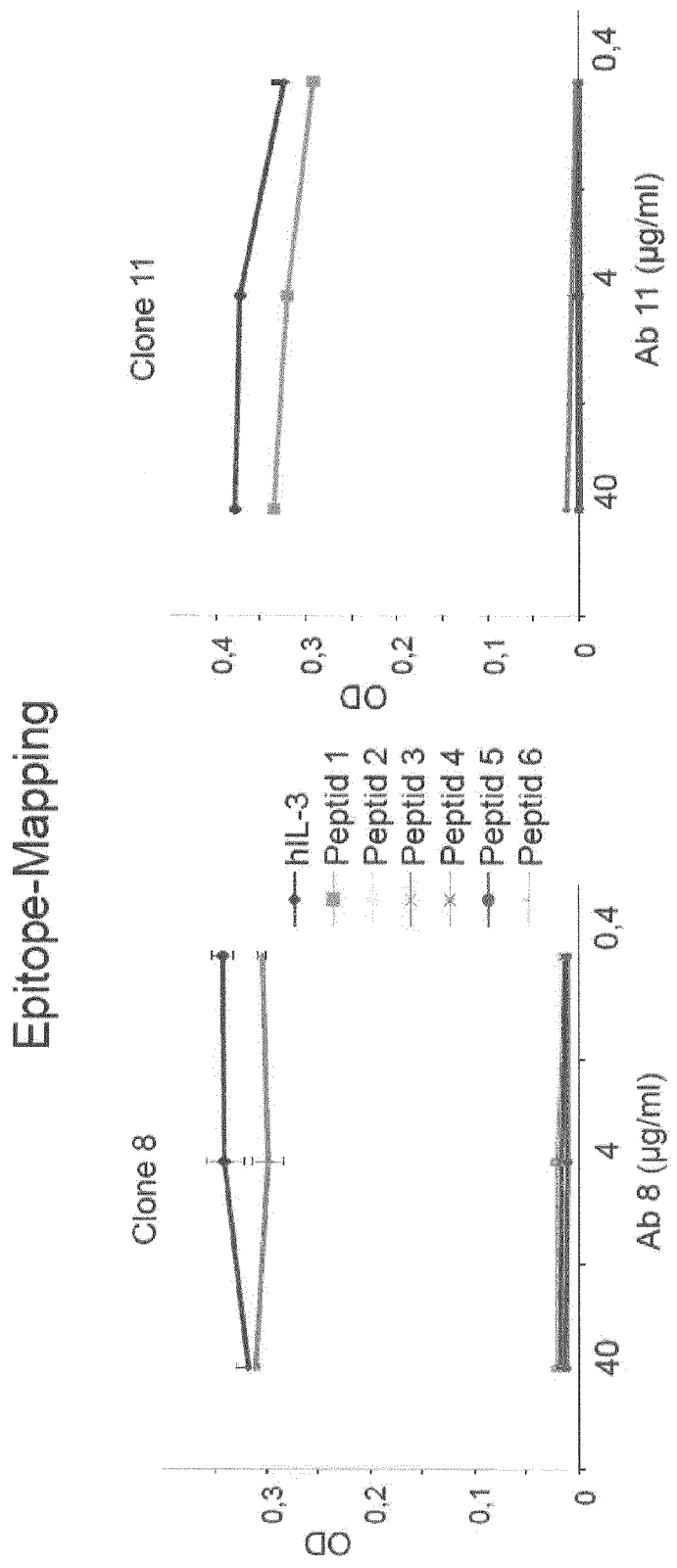

FIGS. 29 and 30 show the results of such ELISA assays indicating that while all antibodies clone 8, clone 11, clone 13 and R&D strongly bound hIL-3, clones 13 and R&D did not have a strong specificity for one of the peptides 1 to 6, whereas clone 11 and clone 8 bound specifically to peptides 1 and 6, respectively.

Figure 32:
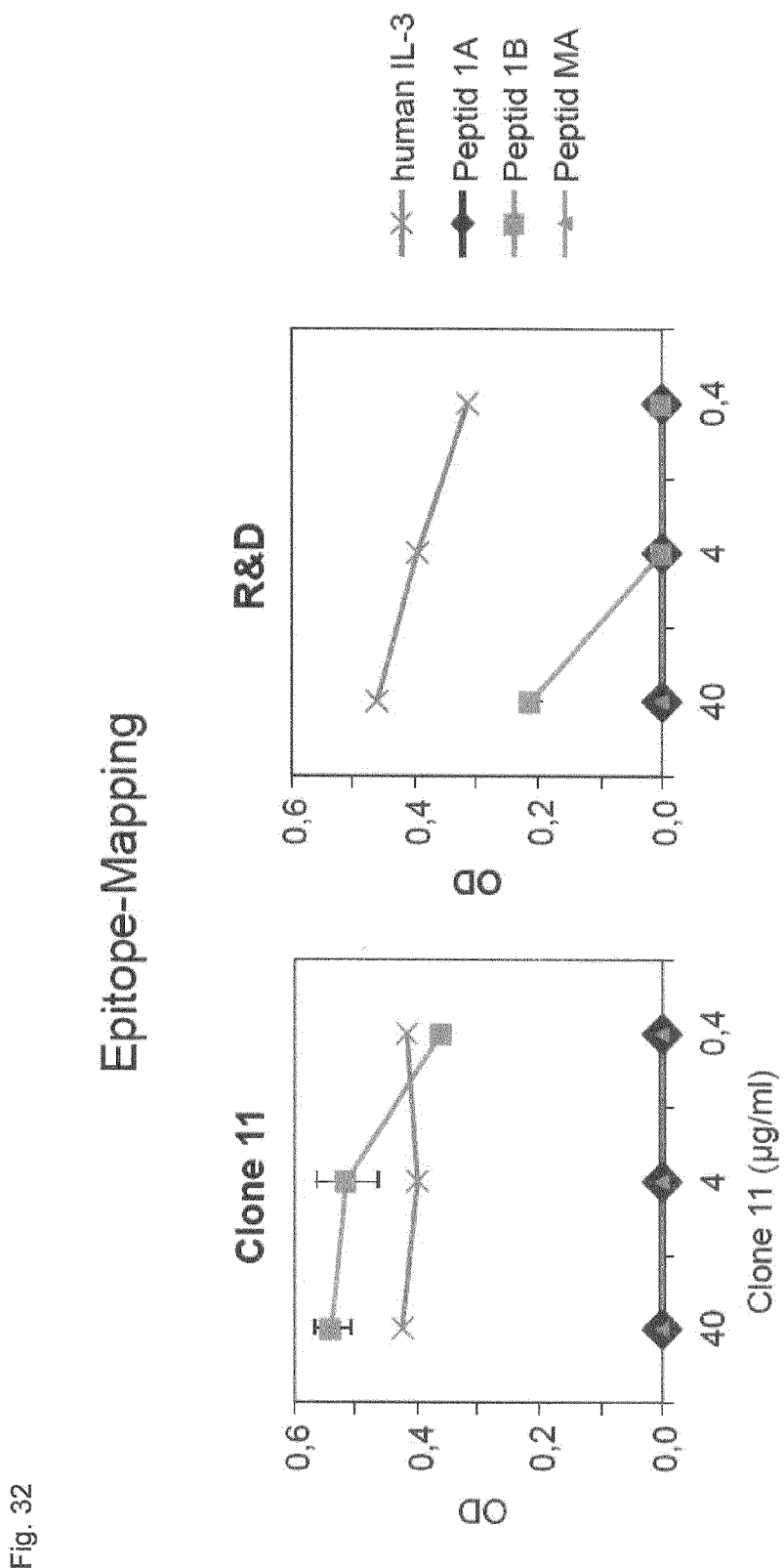

FIG. 31 shows a set of mutated forms of peptide 1 (SEQ ID NOs: 9-13) which were used for a further fine mapping of species-specific epitopes in this part of the IL-3 protein sequence. The peptides were used in ELISA assays for testing antibody clone 11 and the R&D anti-IL-3 antibody with regard to their specificity. The results of the assays are shown in FIG. 32. Among this set of peptides, the R&D antibody does not show a strong specificity for any one of them but binds strongly only to the complete IL-3. Clone 11 on the other hand, shows a strong binding to peptide 1B only, but does not bind to other peptides which are related to rhesus or marmoset IL-3 proteins.

FIGS. 33 to 36 show the results of ELISA assays which were performed using differing combinations of coating and detection antibodies selected from the antibody clones 8, 11, 13, 44 and 47 as well as using a commercially available test kit. The results indicate that best performance can be achieved by using a combination of clones 11 and 13 and that these tests work tremendously well to detect and quantitate IL-3, even when body fluids (plasma, serum) are used as test samples.

FIGS. 37 to 40 show the results of ELISA assays performed to investigate the stability of tests performed inter alia with plasma and serum and using as the coating (solid-phase bound) antibody clone 13 and as detection antibody HRP-labelled clone 11. Plasma and serum samples containing IL-3 were stored for the given periods of time at various temperatures. The test results confirmed very good stability and performance for the test formats.

Figure 41:
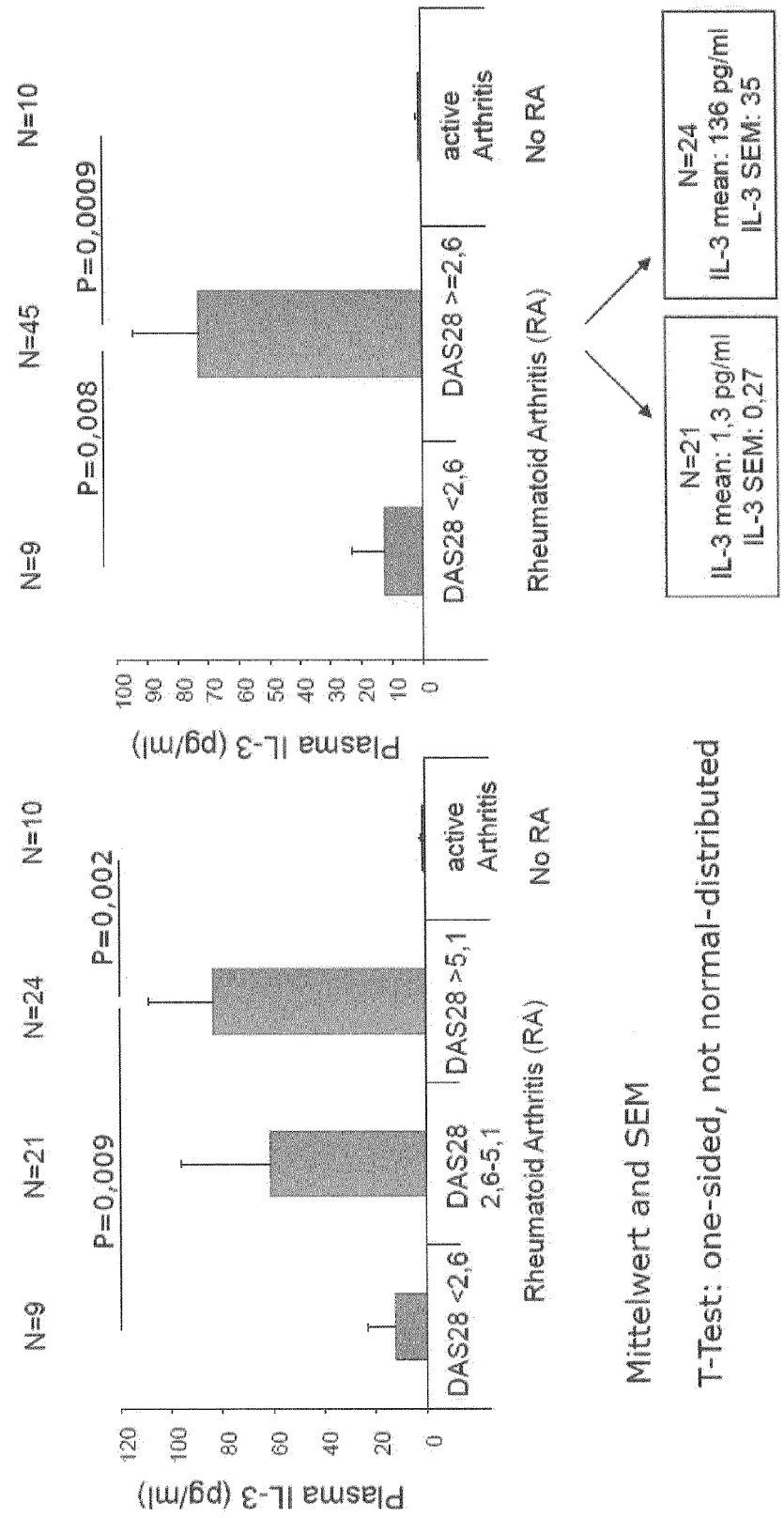
Figure 42:
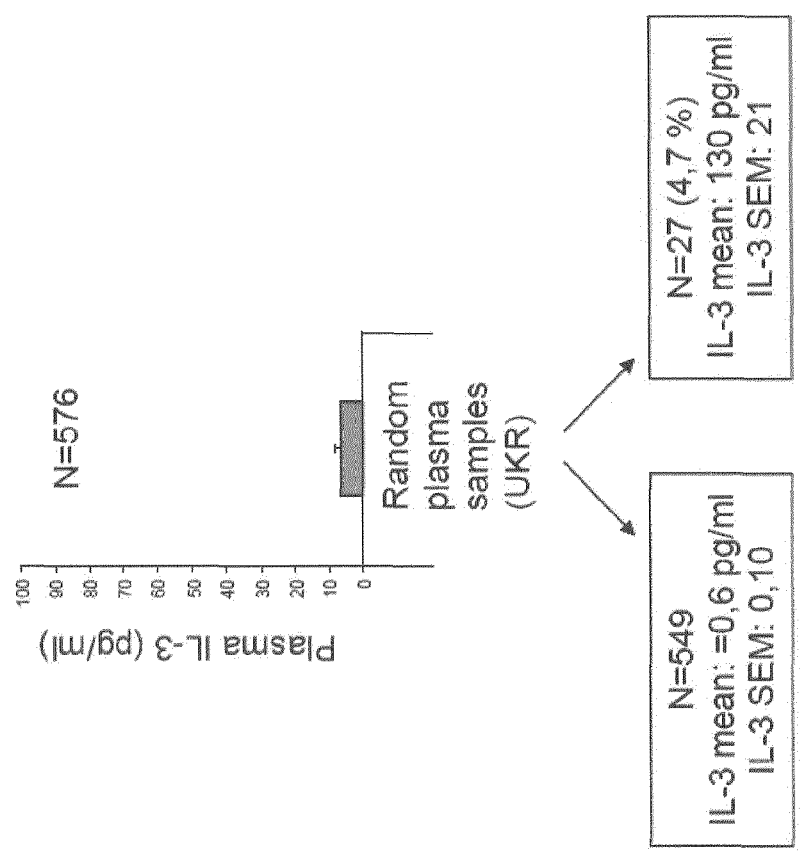

FIGS. 41 and 42 show clinical data regarding the plasma IL-3 levels of patients with or without active RA, as well as data showing an analysis of plasma IL-3 levels of randomly picked patients presenting at the University Hospital Regensburg. The results indicate that in general only a small percentage of randomly picked patients show IL-3 levels above 20 pg/ml, while more than 50% of patients with active RA have IL-3 levels above 20 pg/ml. Among confirmed active RA patients, there are two subgroups only one of which shows high plasma levels of IL-3.

Figure 43:
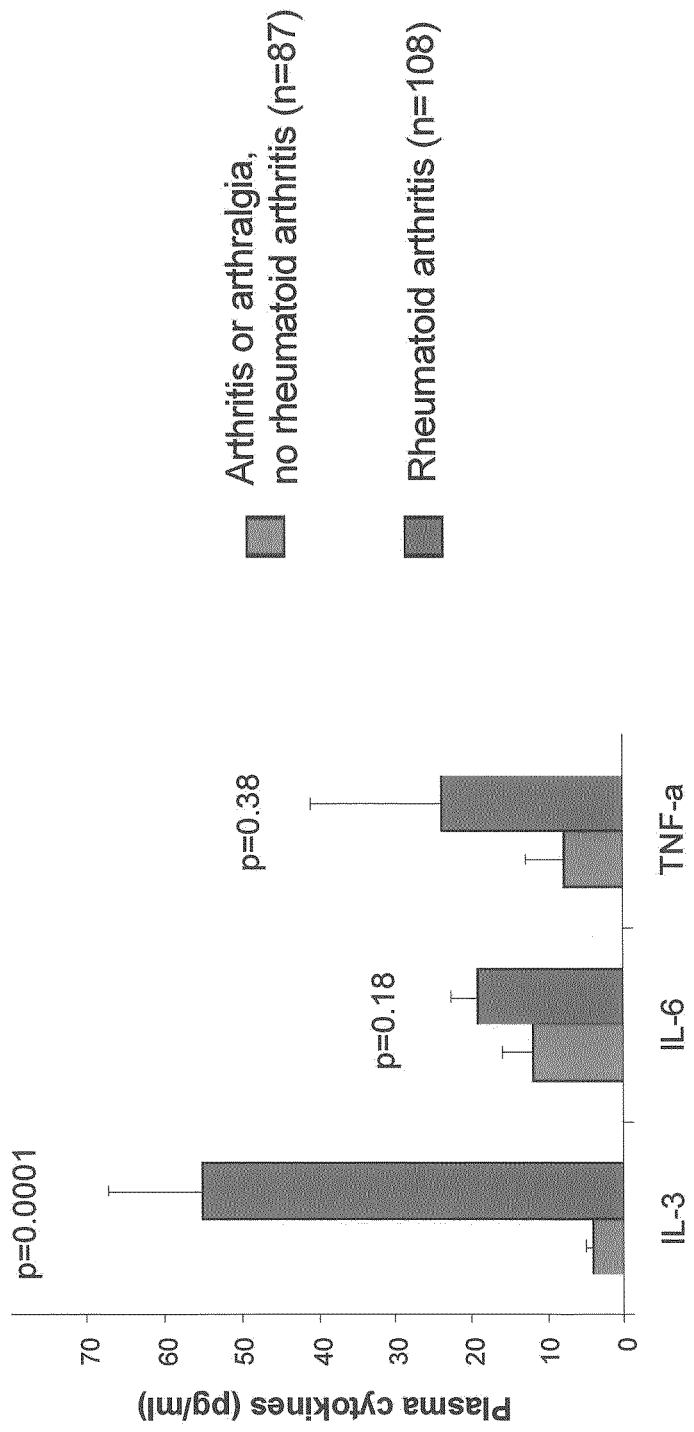
Figure 44:
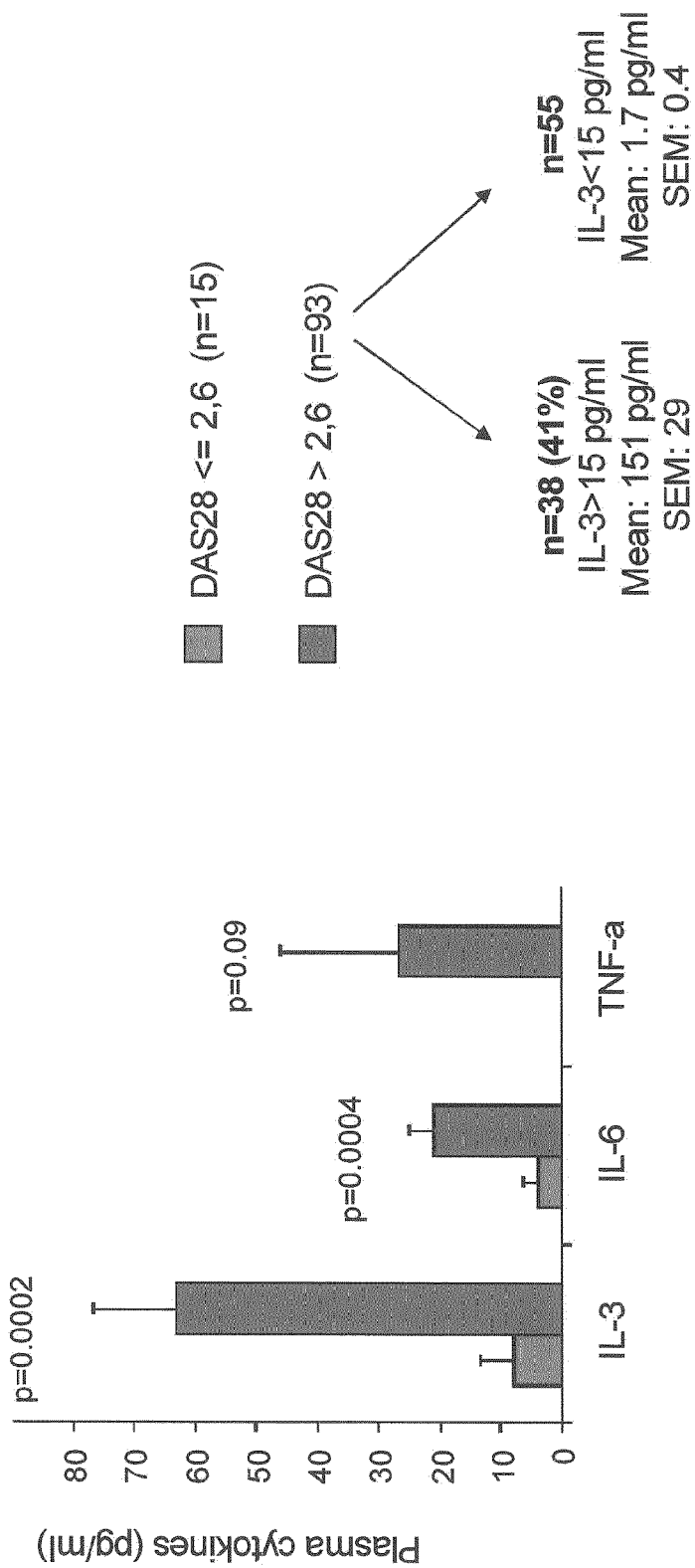

FIGS. 43 and 44 show clinical data regarding the plasma IL-3, IL-6 and TNF-α levels of patients with or without active RA (FIG. 43), as well as data showing an analysis of cytokine levels in patients with diagnosed RA (FIG. 44). The results indicate that IL-3 but not IL-6 or TNF-α can separate between RA and non-RA types of arthritis (FIG. 43). Furthermore, what can be concluded from the data presented in FIG. 43 is that IL-3 and IL-6 but not TNF-α correlate with disease activity in patients with RA.

Figure 45:
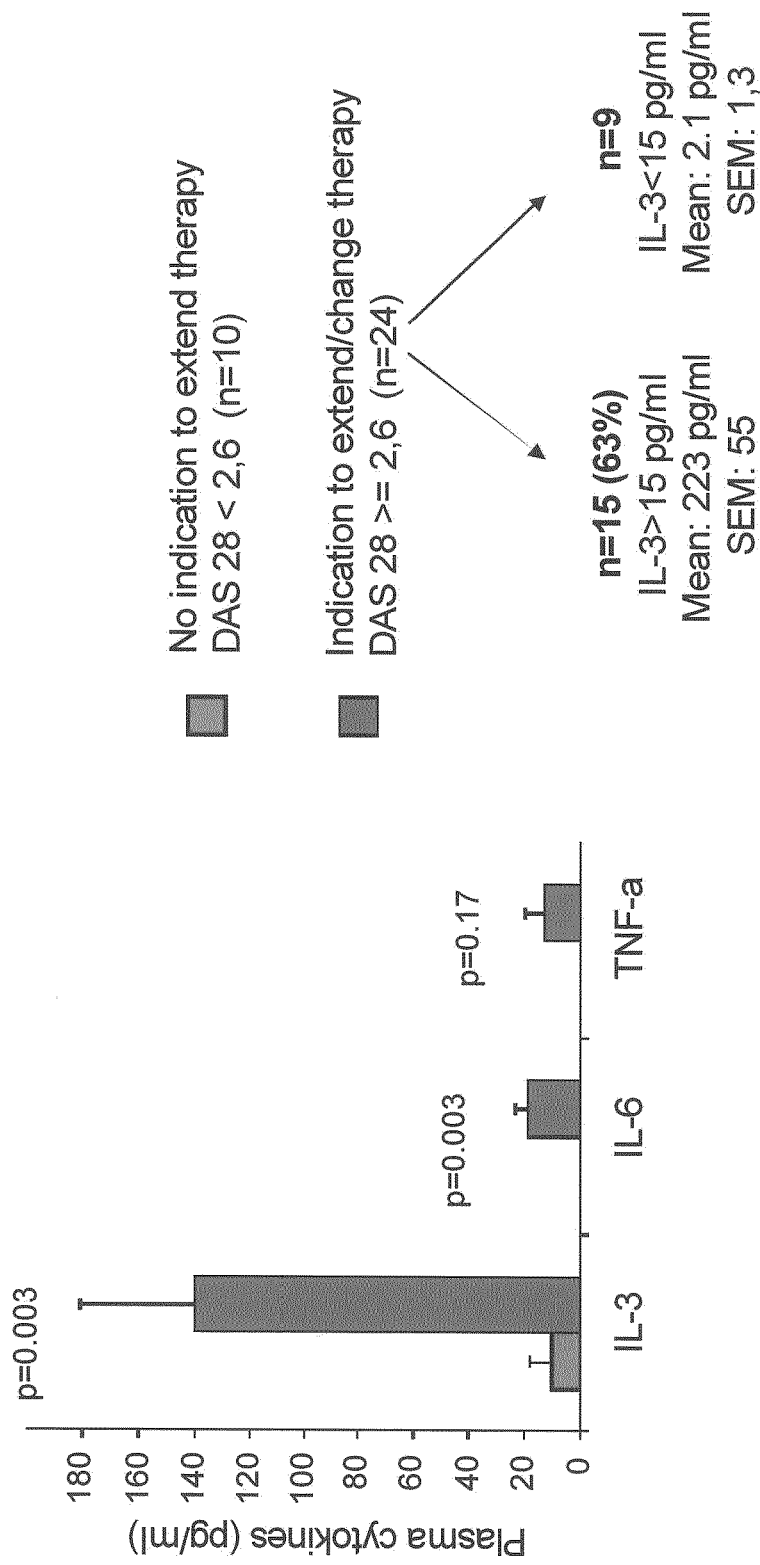

FIG. 45 shows clinical data regarding the plasma IL-3, IL-6 and TNF-α levels of RA-patients treated with DMARD and/or biologicals. The data indicate that 63% of RA patients not responding to DMARDs/biologicals express high IL-3 levels. Patients with high IL-3 levels are more frequent among those patients that did not respond to current therapies. These patients would qualify for treatment with anti-IL-3-antibodies.

EXAMPLE 1

Generation of Monoclonal Anti-IL-3 Antibodies

Anti-IL-3 antibodies were produced by immunizing Balb/c mice using at least 6 i.p. injections of human eukaryotic glycosylated IL-3 in alumn at four week intervals. Two days before cell fusion, IL-3 in PBS was injected intraperitoneally. Antibody-producing splenocytes obtained from the immunized mice (HGPRT positive, able to grow on HAT medium) were fused with the myeloma cell line X63Ag8.6.5.3 in the presence of polyethylene glycol (PEG) and a selection of hybridomas performed in an HAT-selection medium. Hybridomas were cultivated in RPMI-1640 medium supplemented by 10% FCS (neat inactivated, HA), P/S and glutamine (1:100). Obtained cells are able to grow in suspension and are splitted every three days in a ratio of 1:4.

For storage purposes hybridoma cells are transferred from a cell culture bottle into 50 ml or 15 ml cell culture flasks (BD Falcon™). After centrifugation at 1400 rpm for 5 minutes at room temperature, the supernatant is completely removed. Cells are resuspended in a freezing medium (90% FCS (HIA)+10% DMSO) and 1.5 ml aliquots are filled into vials. The cells are prefrozen in a freezing container in a freezer at −80° C. and after 1-2 days transferred to a liquid nitrogen storage tank.

Cloning and recloning of the obtained hybridoma cell lines are performed using limited dilution to provide long-term stable sources for monoclonal antibodies.

Obtained antibodies are shown in table 1.

For determining the isotypes of the antibodies, ELISA assays were performed using hIL-3 coated plates to which the antibodies were added. Bound antibodies were detected using isotype specific secondary antibodies. For further analyses, only antibodies of isotype IgG were used.

TABLE 1

Overview of mAbs against human IL-3

| Original clone | First cloning | Second cloning | Isotype |
| --- | --- | --- | --- |
| Clone 2 | 2.28 | 2.28.11 | IgM, kappa |
| Clone 3 | 3.47 | 3.47.20 | IgG1, kappa |
| Clone 5 | 5.3 | 5.3.2 | IgM, kappa |
| Clone 6 | 6.38 | 6.38.14 | IgG1, kappa |
| Clone 7 | 7.42 | 7.42.45 | IgM, kappa |
| Clone 8 | 8.36 | 8.36.38 | IgG1, kappa |
| Clone 10 | 10.12 | 10.12.4 | IgG1, kappa |
| Clone 11 | 11.14 | 11.14.6 | IgG1, kappa |
| Clone 13 | 13.47 | 13.4.4 | IgG1, kappa |
| Clone 36 | 36.26 | 36.26.10 | IgG1, kappa |
| Clone 38 | 38.18 | 38.18.5 | IgG1, lambda |
| Clone 41 | 41.28 | 41.28.4 | IgG1, kappa |
| Clone 42 | 42.47 | 42.47.36 | IgG1, kappa |
| Clone 43 | 43.14 | 43.14.28 | IgG1, kappa |
| Clone 44 | 44.16 | 44.16.16 | IgG1, kappa |
| Clone 45 | 45.14 | 45.14.27 | IgG1, kappa |
| Clone 46 | 46.21 | 46.21.1 | IgG1, kappa |
| Clone 47 | 47.28 | 47.28.15 | IgG1, kappa |

EXAMPLE 2

Determination of the Amount of IgG1 in the Hybridoma Supernatants

Several of the obtained antibodies of the type IgG1 were isolated from hybridoma clones and their concentration determined. The determination of the concentration was performed according to following method: 96-well-plates are coated overnight at room temperature with anti-mouse IgG (1:100 in PBS) in a concentration of 100 µl/well. Blocking is performed by adding 100 µl per well of 2% BSA in PBS and incubation at room temperature for two hours. After the blocking reaction, the plates are washed twice. Two samples and blanks, respectively, of supernatants of clones 3.47.20, 6.38.14, 8.36.38, 10.12.4, 11.14.6 are incubated undiluted, as well as with dilutions of 1:3, 1:9, 1:27, 1:81, 1:243, 1:729 and 1:2187 (100 µl per well, dilution in 2% BSA in PBS) at room temperature. Mouse IgG1 in a starting concentration of 1 mg/ml is used as standard, whereas a concentration of 20 ng/ml is applied in dilutions of 1:2, 1:4, 1:8, 1:16, 1:32, 1:64 and 1:128.

The plate is washed three times and then incubated with biotinylated anti-mouse IgG1 (diluted by 1:250 in 2% BSA in PBS) for one hour at room temperature with 100 µl per well. After washing the plate a further three times, streptavidin-HRP (1:1000 in 2% BSA in PBS) is added for one hour at room temperature and in the dark. The concentration of the antibodies is determined after adding ABTS and incubating for further 30 minutes and measuring the signal at 405 and 490 nanometers on a spectrophotometer. Based on this determination, a desired amount of the antibodies tested is applied for the further tests.

EXAMPLE 3

Detection of IL-3 by Monoclonal Antibodies in a Western-Blot Assay

For preparing the gel and performing the western-blot analysis, standard methods are used. A 12% PAA resolving gel is poured, overlayed with about 1-2 ml of water and polymerisation conducted for 30 to 45 min until a recognizable "line" is formed. The water is removed, a stacking gel poured onto the resolving gel and a TEFLON® comb is inserted. Polymerisation is performed for 30 min, then the comb is carefully removed.

Samples of IL-3 are prepared by mixing of recombinant human IL-3 1:1 with Laemmli buffer and heating the samples at 60° C. for 5 min. An amount of 1 µg per lane of IL-3 as well as a usual standard for determining molecule sizes is loaded onto the gel. The gel is then mounted in a SDS-PAGE gel electrophoresis apparatus which already contains a running buffer. The inserted gel is then cautiously overlayed with additional running buffer and electrophoresis performed at 20 to 25 mA with voltage adjusted to infinite for approximately 1.5 hours. When the run is completed, the gel is retrieved from the apparatus and the stacking gel is removed.

Six layers of Whatman paper that has been presoaked in transfer buffer, and a PVDF membrane are cut to fit the size of the gel. The transfer stack is adjusted in the usual way and transfer effected by semi-dry blotting for 40 min at 20-25 mA and voltage adjusted to infinite. The membrane is then incubated overnight at 4° C. on a shaking apparatus with a blocking solution (5% powdered skim milk in PBS) and the membrane washed three times for 5 min each with PBS at room temperature.

Antibody clones are incubated at a concentration of 5 µg/ml in blocking solution for 2 hours at room temperature under agitation on the shaking apparatus. After three washing steps, HRP labelled anti-mouse immunoglobulin (1:1000 in blocking solution) is added and incubation is conducted for 1 hour at room temperature while shaking. After three further washing steps, a detection solution (1:1 mixture of solutions A and B of the Westernblotting Luminal Reagent obtained from NALGENE) is added and incubated for 1 min at room temperature. Films are then adjusted on the membranes with different times of expositions and developed in the dark room.

Figure 2:
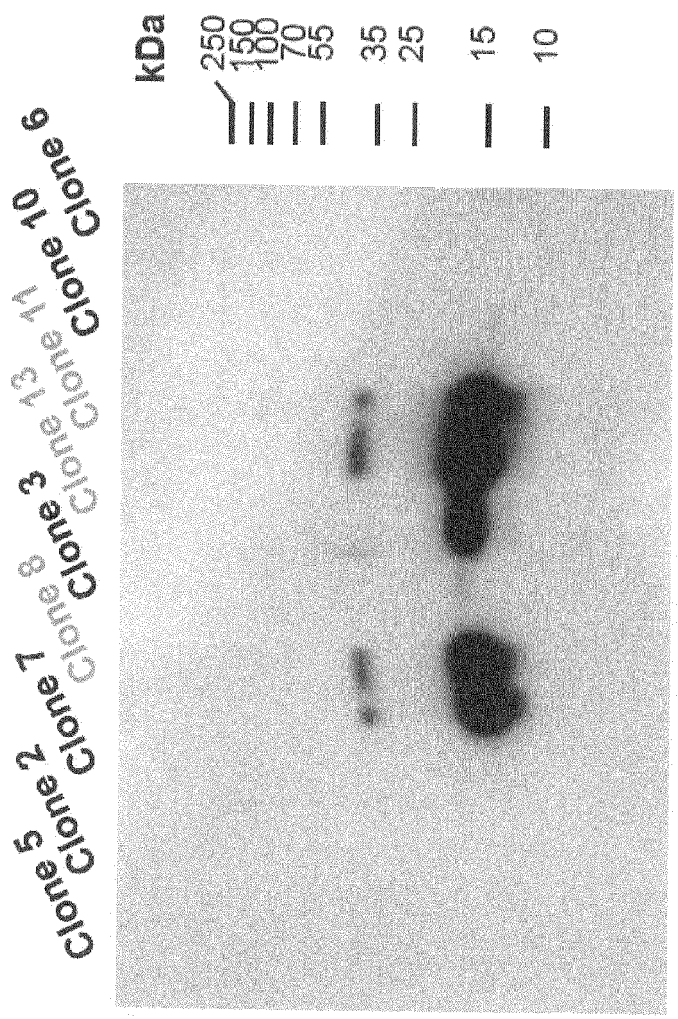
FIG. 2 shows in a Western blot the ability of monoclonal antibodies to bind to IL-3.

FIG. 2 shows the results of binding of antibody clones 2, 3, 5, 6, 7, 8, 10, 11 and 13. Binding to IL-3 at the given concentration was detected for clones 8, 11 and, to a lesser extent, for clone 13.

EXAMPLE 4

Analysis of the IL-3 Affinity and Specificity of Monoclonal Antibodies a) Affinity of the Antibodies for IL3

The affinity of the obtained antibodies for IL-3 was measured in an ELISA assay. ELISA plates were coated overnight with different concentrations (2 µg/ml, 0.66 µg/ml, 0.22 µg/ml, 0 µg/ml) of anti-human IL-3 antibody (RD, goat IgG anti-human IL-3 AF-203-NA). For each concentration, duplicates were used (2×12 wells). For this purpose, the first concentration (2 µg/ml) is diluted in PBS, further dilutions are made in PBS containing 2 µg/ml control goat IgG to keep the total concentration of IgG constant. Blocking with 2% BSA is performed for 2 hours at room temperature, followed by 5 washing steps using PBS.

The wells are then incubated with hIL-3 (0.25 µg/ml in PBS) for 2 hours at room temperature, for the control group no hIL-3 is added. After five further washing steps with PBS, the wells are incubated overnight at 4° C. with serial (1:3) dilutions of antibodies clone 8 and 11 obtained in example 1, the antibodies being used in PBS buffer containing 2% BSA and with a starting concentration of 20 µg/ml.

After five further washing steps, bound antibody is detected using goat-anti-mouse-HRP antibody (1:500 in PBS with 2% BSA) and incubation for 1 hour at room temperature. After five further washing steps, ABTS (ROCHE, 1 mg/ml) is added as substrate and the optical density measured in a spectrometer at 405 nm.

Results are shown in FIGS. 3 and 4 for antibodies clone 8 and 11, respectively. Both antibodies show a high affinity for IL-3 in the assay. FIG. 5 shows the results of further tests including other antibodies. The tests were performed in the same manner as described, however, coating of the solid phase was performed using 1 µg/ml goat IgG anti-human IL 3 (see above) and different concentrations/dilutions of antibodies as shown in the figure.

b) Cross-Reactivity with Other Cytokines

To determine the usefulness of the obtained monoclonal antibodies for diagnostic assays, it is important to be able to exclude cross-reactivities with closely related cytokines which are also present in blood, plasma, serum or other body fluids of patients. To this end, wells of ELISA plates were coated by adding 100 µl/well of human IL-3 (1 µg/ml), GM-CSF (1 µg/ml) or IL-5 (1 µg/ml) in PBS. As negative control PBS was used (100 µl/well). For each tested antibody, different dilutions were tested mandatorily on a common plate with hIL-3, hGM-CSF, hIL-5 and PBS.

The cytokine coated plates were washed three times and blocking performed for 2 hours at room temperature using 2% BSA in PBS. After three further washing steps, antibodies clone 3.47.20, 8.36.38, 10.12.4, 11.14.6, 13.4.4 and just medium (RPMI1640 containing 10% FCS) as control were added at a concentration of 40 µg/ml and 1:5 and 1:25 dilutions thereof in a volume of 100 µl/well and incubated for 1 hour at room temperature. On each plate a negative control is used.

After three washing steps, a secondary HRP-labelled rabbit anti-mouse IgG (DAKO-Cytomation P260 (1:2000 in 2% BSA in PBS, 100 µl/well) was added and the plates incubated at room temperature for 1 hour in the dark. After another three washing steps, ABTS (ROCHE, 1 mg/ml) was added and spectrometry performed at 405 and 490 nm after 30 min.

The results are shown in FIG. 6 indicating some weak cross-reactivity for clones 8 and 10, but no significant cross-reactivity for clones 11 and 13.

c) Cross-Reactivity with IL-3 from Other Species

As a further property of the monoclonal antibodies, their cross reactivity with IL-3 from other species was determined. For a respective assay, the wells of ELISA plates were coated with human, murine, rat and rhesus IL-3 (1 µg/ml) in PBS as well as with PBS as background with 100 µl/well and incubated overnight in a refrigerator. For each antibody, different dilutions were tested mandatorily on a common plate with hIL-3, murine IL-3, rat IL-3, rhesus IL-3 and PBS negative control.

The IL-3 coated plates were washed three times and blocking performed for 2 hours at room temperature with 2% BSA in PBS. After three washing steps, antibody clones 3.47.20, 8.36.38, 10.12.4, 11.14.6, 13.4.4 in certain concentrations as indicated in FIGS. 7 and 8, and 1:5, 1:25 and 1:125 dilutions thereof were added at volumes of 100 µl/well. R&D monoclonal anti-IL-3 antibody clone 4806 (R&D Systems, Inc., catalogue No. MAB203) was used (100 µl/well) in concentrations of 40 µg/ml, 20 µg/ml, 10 µg/ml, 5 µg/ml and 2.5 µg/ml and, as negative control, medium (100 µl/well) without antibody (RPMI 1640 containing 10% FCS) was used. On each plate a negative control was used.

After three washing steps, a secondary HRP-labelled rabbit anti-mouse IgG (DAKO-Cytomation P260 (1:2000 in 2% BSA in PBS, 100 µl/well) was added and the plates incubated at room temperature for 1 hour in the dark. After another three washing steps, ABTS (ROCHE, 1 mg/ml) was added and spectrometry performed at 405 and 490 nm after 30 min.

Results are shown in FIGS. 7 and 8, as mentioned above, indicating that albeit a faint cross reactivity of clone 10, none of the antibodies of example 1 showed detectable cross-reactivity. The R&D antibody on the other hand, showed some cross-reaction with rhesus IL-3.

EXAMPLE 5

Analysis of the Blocking Properties of Monoclonal Antibodies

To analyse the ability of antibodies obtained according to example 1 to block IL-3 activity, several different experiments were performed.

a) Analysis of the Ability of Antibodies to Block IL-3 Based on the IL-3 Dependent Growth of TF1 Cells:

TF1 cells are human erythroblasts and the cell line has been established by T. Kitamura in 1987 from bone marrow of a 35 year old male Japanese suffering from severe pancytopenia. Growth of TF1 cells is completely dependent on the presence of IL-3 or GM-CSF. Thus, a test based on the cell proliferation of TF1 cells can be used to determine blocking of the IL-3 activity which in turn leads to a decrease or even a complete inhibition of the growth of TF1 cells. For such a test, a MTT-cell-proliferation assay is performed to determine the viability of cells based on the activity of the mitochondrial dehydrogenase. The dehydrogenase's substrate MTT (3-(4,5-dimethylthiazol-2-yl)-2,5-diphenyl tetrazolium bromide) which shows a yellow color in solution, is cleaved at the tetrazolium ring by the enzymatic activity leading to formation of purple MTT formazane crystals. Such crystals can be dissolved in isopropanol, the purple solution measured in a spectrometer and the results correlated to the amount of viable TF1 cells.

Cultivation of TF1 Cells:

TF1 cells were grown in suspension in a culture medium (RPMI-1640 containing 10% FCS (HIA), P/S and Glutamin (1:100) and supplemented with either 5 ng/ml of IL-3 or 5 ng/ml of GM-CSF) and splitted 1:4 every third day. For storage, cells were transferred from a cell culture bottle to 50 ml or 15 ml cell culture flasks (BD Falcon™). After centrifugation at 1400 rpm for 5 minutes at room temperature, the supernatant is completely removed. Cells are resuspended in culture medium (RPMI-1640 containing 10% FCS (HIA)+P/S+Glutamin+5 ng/ml IL-3) and 5% DMSO and 1.5 ml aliquots are filled into vials. The cells are prefrozen in a freezing container in a freezer at −80° C. and after 1-2 days transferred to a liquid nitrogen storage tank.

Blocking Experiment:

TF-1 cells that had been splitted every third day according to the protocol described above are splitted 1:2 in culture medium containing 5 ng/ml human IL-3 on the day before the experiment is performed.

For the experiment, cells are centrifuged for 5 minutes at 1600 rpm at room temperature. The culture medium is removed and the cells washed twice in RPMI medium before cells are resuspended in 1 ml RPMI-1 640+10% FCS (HIA)+P/S+Glutamin (1:100), counted and supplemented with buffer to a final concentration of $1\times10^5$ cells/ml.

In a 96-well-plate, 10,000 cells in 100 µl medium (RPMI+10% FCS+P/S+Glutamin) are provided to each well. 100 µl of IL-3 which has been preincubated with monoclonal antibody of example 1 for 60 min at 37° C. For the preincubation different final concentrations of antibody and IL-3 are used. To obtain such final concentrations, the concentration of the antibody and IL-3 solutions needs to be twice the amount of the end concentration. After 5 days of incubation at 37° C. and addition of 5% $CO_2$, 100 µl of medium are removed from each well and 10 µl MTT solution (LCG Standard-ATCC) are added to each well and the plates incubated for another 4 hours in an incubator at 37° C. and 5% $CO_2$. After this further incubation, 100 µl MTT solvent are added and the contents of the wells mixed carefully. After an overnight incubation, optical density is determined at 570 and 690 nm and the number of viable cells calculated therefrom.

Experiments were performed for antibody clones 8.36.38 (clone 8), 11.14.6 (clone 11) 13.4.4 (clone 13), a commercially available anti-hIL-3 antibody clone 4806 (RD catalogue No. MAB203) and a mouse IgG1 kappa MOPC 21 antibody (without azide) as isotype control (Sigma-Aldrich).

The general influence of IL-3 on the growth of TF1 cells is shown in FIG. 9. Results for different amounts of IL-3 with and without different concentrations of mAbs are shown in FIGS. 10 to 13.

b) Analysis of a Possible Influence of Anti-IL-3 Antibodies on the GM-CSF Dependent Growth of TF1 Cells As mentioned above, growth of TF1 cells is dependent on the presence of IL-3 or GM-CSF. As shown in example 5a), anti-IL-3 antibodies have a negative effect on the growth of TF1 cells. IL-3 binds to the IL-3 receptor which is comprised of an alpha chain of 70 kDa and a beta chain of about 130 kDa. The same beta chain is also present on receptors for IL-5 and GM-CSF. Therefore, in another experiment it was tested whether anti-IL-3 antibodies also influence the growth of TF1 cells in the presence of GM-CSF. For this purpose, the experiment described above was repeated adding GM-CSF, IL-3 and mixtures thereof preincubated with the anti-IL-3 antibodies to the culture medium of TF1 cells. A control without GM-CSF and IL-3 was included.

The general influence of GM-CSF on the growth of TF1 cells is shown in FIG. 14. The results of the tests in view of the blocking of this influence and amounts of GM-CSF and antibodies, respectively, used in this example are shown in FIG. 15 indicating that none of the tested antibodies had a blocking effect on GM-CSF and its growth induction toward TF1 cells.

c) Analysis of the Ability of Anti-IL-3 Antibodies to Inhibit Binding of IL-3 to Human PBMC Binding of IL-3 to human peripheral blood mononuclear cells (PBMC) was analysed using commerically available biotinylated IL-3. For the assay, biotinylated IL-3 was incubated with PBMC and binding detected via Avidin-Fluorescein (biotinylated hIL-3 and other reagents obtained from R&D Systems, Inc., Cat. No. NF300).

For this purpose, human PBMC cells were isolated from human blood using the Ficoll-gradient centrifugation method. Cells were resuspended at a concentration of 10 Mio. cells/ml (in PBS) and 10 µl aliquots incubated with purified polyclonal mouse IgG (SIGMA-Aldrich) for 15 min at room temperature, to block Fc mediated interactions.

In separate reactions, biotinylated hIL-3 was preincubated with dilutions of antibodies. For this purpose, 10 µl of biotinylated hIL-3 (1.25 µg/ml) were preincubated with 10 µl of anti-IL-3 antibody at 100 µg/ml or dilutions thereof at 1/3, 1/9, 1/27, 1/81 and 1/243, or with 10 µl PBS, 10 µl isotype antibody (50 µg/ml) or 20 µl blocking Ab (R&D Systems Cat No NF300) and incubated for 30 min at room temperature.

For the negative control, 10 µl of a negative control reagent (R&D Systems Cat. No. NF300) were preincubated with 15 µl of anti-IL-3 antibody (50 µg/ml), 10 µl PBS, 10 µl isotype antibody (50 µg/ml) or 20 µl blocking AB (R&D Systems Cat. No. NF300).

10 µl of the isolated and incubated PBMC cell preparation (10 Mio. cells/ml) were added to each of the preincubated IL-3/antibody or negative control samples and further incubated for 1 hour at 4° C. For the detection of IL-3 bound to PBMC, 10 µl avidin-FITC reagent together with anti-human CD123 PE-Cy5 (1:10) and anti-HLA-DR II APC (1:50) were added and the samples incubated for a further 30 min at 4° C. Cells were washed twice with 2 ml 1×RDF1 buffer and resuspended in 200 µl of this buffer per sample and FACS analysis performed. Basophils were identified by high expression of CD123 and absence of HLA-DR. Plasmacytoid dendritic cells (pDC) were identified by high expression of CD123 and HLA-DR. Monocytes and B cells were identified by light scatter properties and expression of HLA-DR.

This analysis was performed for the anti-IL-3 antibodies clone 11, 13, 8 (all described in example 1) and the R&D anti-IL-3 antibody (R&D Systems, Inc., cat No. NF 300). Results are shown in FIGS. 16 to 21, indicating binding of IL-3 to the strongly CD123 positive basophilic granulocytes and plasmozytoid dendritic cells and to a lesser extent to the weakly CD123 positive monocytes and B-cells. Antibody clones 11 and 13 and the R&D antibody show a strong inhibition of the binding of IL-3 to the cells, whereas antibody clone 8 showed only weak inhibition.

d) Analysis of the Ability of Anti-IL-3 Antibodies to Inhibit the IL-3 Induced Upregulation of CD203c and Release of IL-4 and IL-13

Human basophilic granulocytes show an IL-3 induced upregulation of CD203c and concurrent release of IL-4 and IL-13. In this example, it was determined whether anti-IL-3 antibodies are also able to inhibit the effect of IL-3 in this regard. For this purpose, PBMC were obtained as described in Example 5c) and basophils purified therefrom using magnetic beads (Basophil Isolation Kit II, Miltenyi Biotech).

Stimulation of basophils was effected by adding hIL-3, anti-IgE (1 ug/ml clone G7-26 BD-Pharmingen) and C5a and combinations thereof to 200,000 basophil cells per well in a total of 220 µl culture medium (RPMI+10% FCS+P/S+Glutamin). The samples were incubated for 5 h or overnight (if not otherwise indicated). The supernatant was recovered and analyzed for presence of IL-13 and IL-4 by ELISA using a commercially available kit from R&D Systems. The basophils were analyzed by flowcytometry for upregulation of CD203c by simultaneous staining with anti-human CD123 PE-Cy5 (1:10), anti-HLA-DR II APC (1:50) and anti-human CD 203c PE (1:10) antibodies (all BD Bioscience). Basophils were identified by high expression of CD123 and absence of HLA-DR. Results are shown in FIGS. 22 to 24.

To determine the inhibiting effect of anti-IL-3 antibodies, tests were performed using human IL-3 in the assay regime as described above but wherein the IL-3 was preincubated with 25 µg/ml of antibody clones 11 and 13, as well as R&D anti-IL-3 antibody clone 4806 (R&D Systems, Inc., catalogue No. MAB203) and isotype antibody (as described in example 1). Results are shown in FIGS. 25 to 27 indicating a strong inhibiting effect of antibodies clone 11 and R&D with regard to upregulation of CD203c and release of hIL-4 and hIL-13, whereas antibody clone 13 showed a strong inhibiting effect on the hIL-13 release only.

EXAMPLE 6

Determination of the Epitope Specificity of the Anti-IL-3 Antibodies

For an epitope mapping, 6 peptides (SEQ ID NOs: 3-8) collectively representing the complete h-IL3 sequence were synthesized with an overlap of 6 amino acids on each side of the peptides (FIG. 28 ELISA plates were coated with human IL-3 (1 µg/ml) and peptides 1 to 6 (1 µg/ml) in PBS, respectively, and as a negative control PBS was used. Each well contained a 100 µl sample and the plates were kept overnight in the refrigerator.

For each of the antibodies and the dilutions thereof, a common ELISA plate was used to test binding to IL3 as well as the peptides 1 to 6. The prepared plates were washed three times and a blocking performed for 2 hours at room temperature with 2% BSA in PBS. After a further three washing steps, antibody clones 8.36.38, 11.14.6, 13.4.4, R&D anti-IL-3 antibody clone 4806 (R&D Systems, Inc., catalogue No. MAB203) and the negative control were added to the wells at 100 µl/well and incubated for 1 hour at room temperature. For the antibodies, dilutions were used containing 40 µg/ml, 4 µg/ml and 0.4 µg/ml.

The plates were washed three times and a secondary HRP labeled rabbit anti-mouse IgG antibody (DAKO-Cytomation, P260) added (1:2000 in 2% BSA in PBS, 100 µl/well) and incubated for 1 hour at room temperature and in the dark. After further three washing steps, ABTS reagent was added and the plates incubated for 30 minutes whereupon spectrometry was performed at 405 and 490 nm. Results are shown in FIGS. 29 and 30 indicating that clone 13 only binds to the complete IL-3 protein, the R&D antibody binds to IL-3 and weakly to peptide 1, whereas clone 11 shows strong binding to IL-3 and peptide 1 and clone 8 shows strong binding to IL-3 and peptide 6. Thus, clone 11 shows very specific and strong binding to an epitope within peptide 1.

For a further determination of possible cross-reactivity of clone 11 with IL-3 from other species and especially the very homologuous proteins from rhesus or marmoset, point mutations were introduced into the sequence of peptide 1. The mutated sequences (SEQ ID NOs: 9-13) used for this assay are shown in FIG. 31.

The same experiment as described above was carried out using these mutated peptides (FIG. 32). The test results indicated a strong binding of antibody clone 11 to peptides IL3-1 and IL3-1B, whereas no binding occurred to IL3-Rhesus, IL3-1A and IL3-MA, indicating a high species specificity of clone 11 for the human protein and highly affine binding of clone 11 to the epitope SWVN.

EXAMPLE 7

Development of a Highly Sensitive and Specific ELISA Assay

Anti-IL-3 antibody clones 8, 11, 13 and further antibody clones 44 (44.16.16, DSM ACC3166) and 47 (47.28.15, DSM ACC3167) were analysed for their use in the development of a highly sensitive and specific ELISA assay for the determination of IL-3, especially for diagnostic purposes in blood, plasma or serum, as well as other body fluids.

To this end, ELISA plates were incubated with 5 µg/ml of anti-IL-3 antibody overnight at room temperature to coat the plates. After three washing steps, blocking is performed using 1% BSA in PBS at 100 µl/well for 1 hour at room temperature. After further three washing steps, samples are incubated with 60 µl/well of IL-3 in various concentrations in PBS, plasma and serum. After another three washing steps, detection of solid-phase bound IL-3 is performed by adding 60 µl/well of a different and HRP labelled anti-IL-3 antibody at a concentration of 400 ng/ml and incubation for 2 hours at room temperature, followed by three washing steps and addition of TMB buffer (10 ml TMB buffer, 1 tablet of TMB, 3 µl $H_2O_2$) (0.1 mg/ml, SIGMA-ALDRICH). The reaction is stopped by adding 100 µl/well of $H_2SO_4$ (12.5% in $H_2O$). The results are obtained by spectrometry at 450 nm and shown in FIGS. 33 to 36.

Labelling of the anti-IL3 antibody clones was performed using the LIGHTNING LINK® HRP Conjugation Kit (Innova Biosciences) using the following protocol: For each of the purified antibody clones 8, 11, 13, 44 and 47 100 µl solutions with a concentration of 1 µg/µl (in PBS) were produced. To each antibody solution, 10 µl of LL-modifying reagent were added and the obtained solution mixed carefully. For each antibody solution a LIGHTNING LINK® mix bottle (100 µg reagent) was opened and the antibody solution including the LL-modifying agent added directly onto the reagent powder. Mixing was performed very cautiously by up- and down-pipetting of the solution. The lid was readjusted on the bottle of the LIGHTNING LINK® mix and the bottles incubated for 3 hours at room temperature whereupon 10 µl LL-quencher reagent were added and incubated for a further 30 min at room temperature. After this treatment the antibodies were stored at −20° C. for further use.

As a comparative assay, analogue tests were performed using the QUANTIKINE® Human IL-3 ELISA test kit provided by R&D Systems, Inc., Catalogue No. Dy 203.

Figure 33:
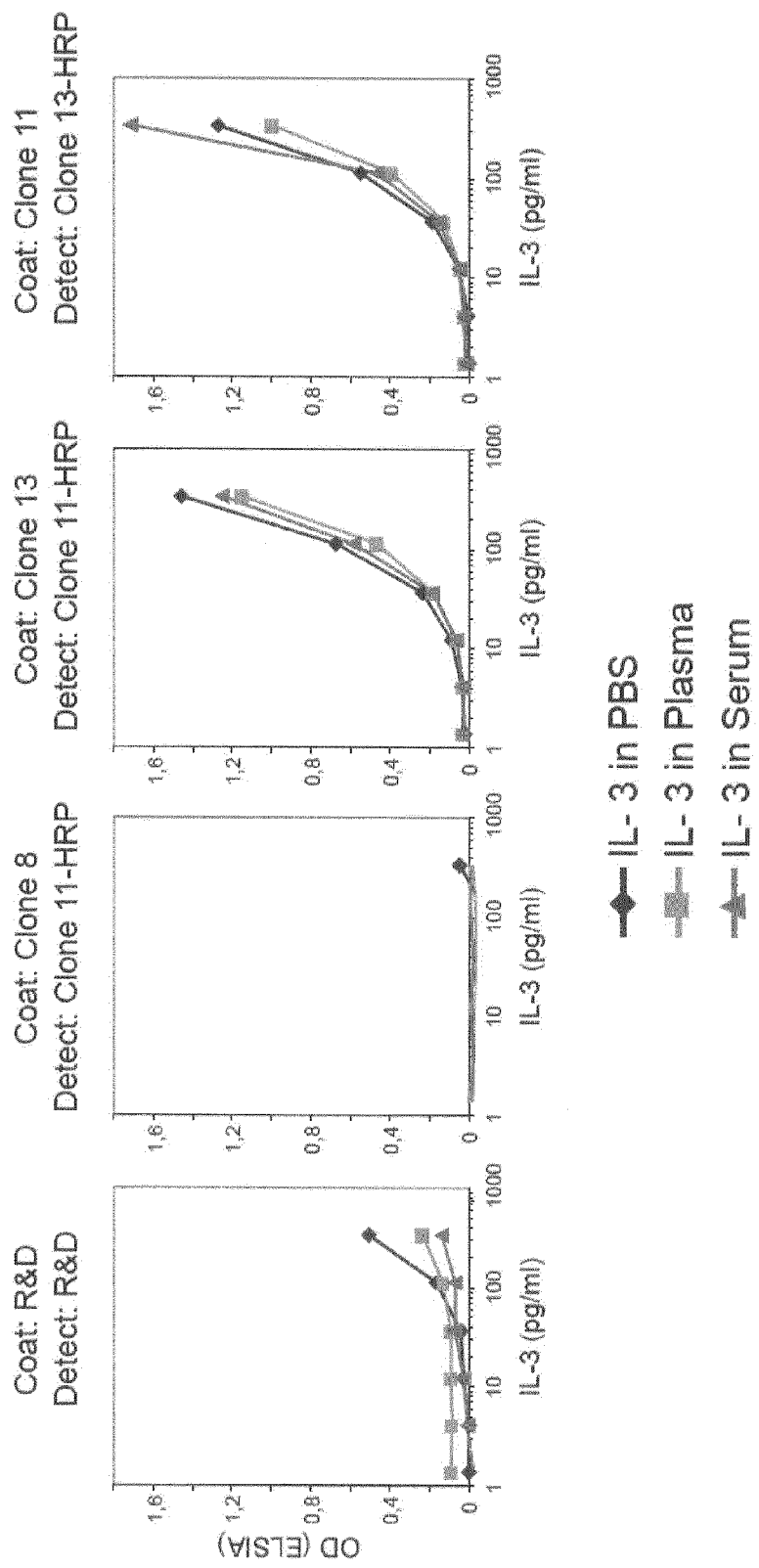
Figure 34:
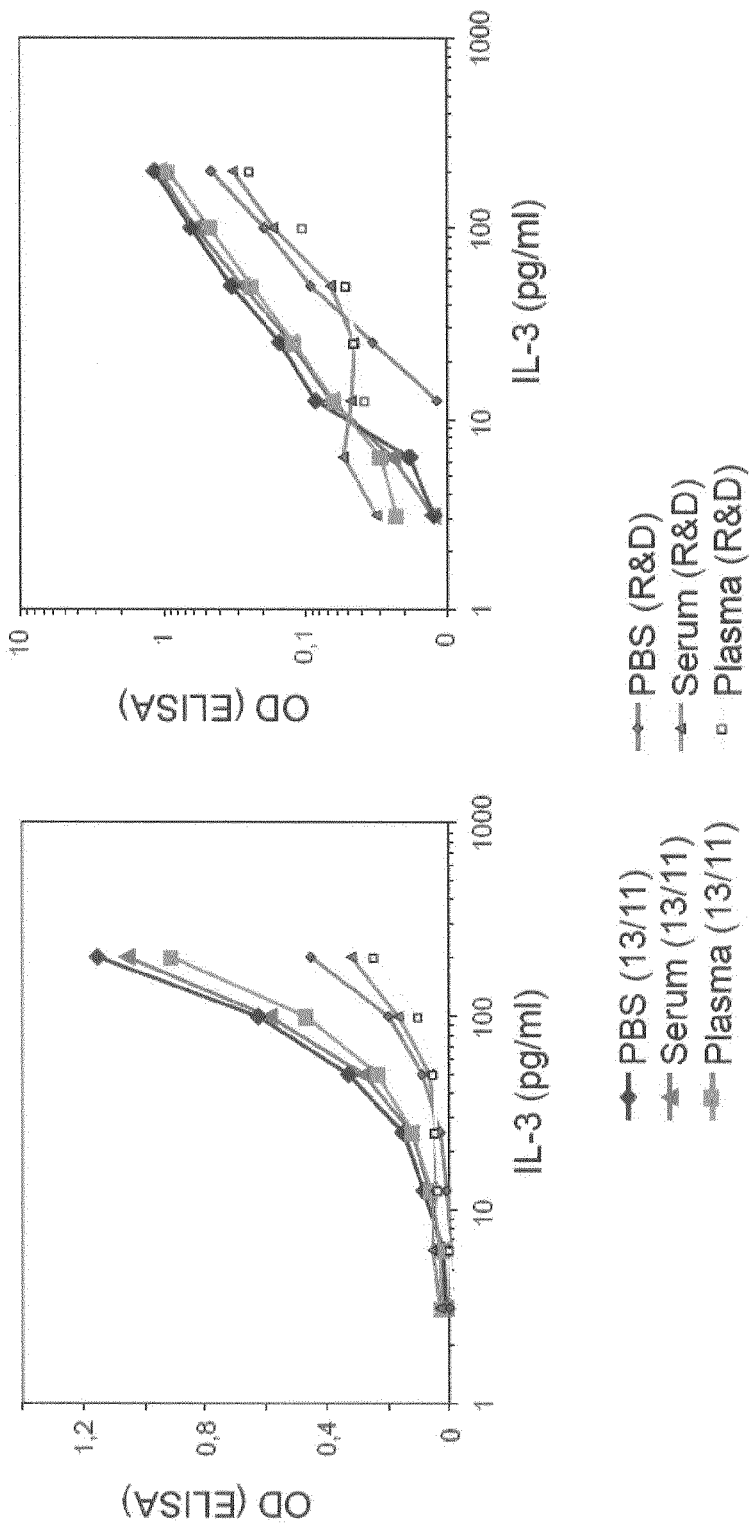
Figure 35:
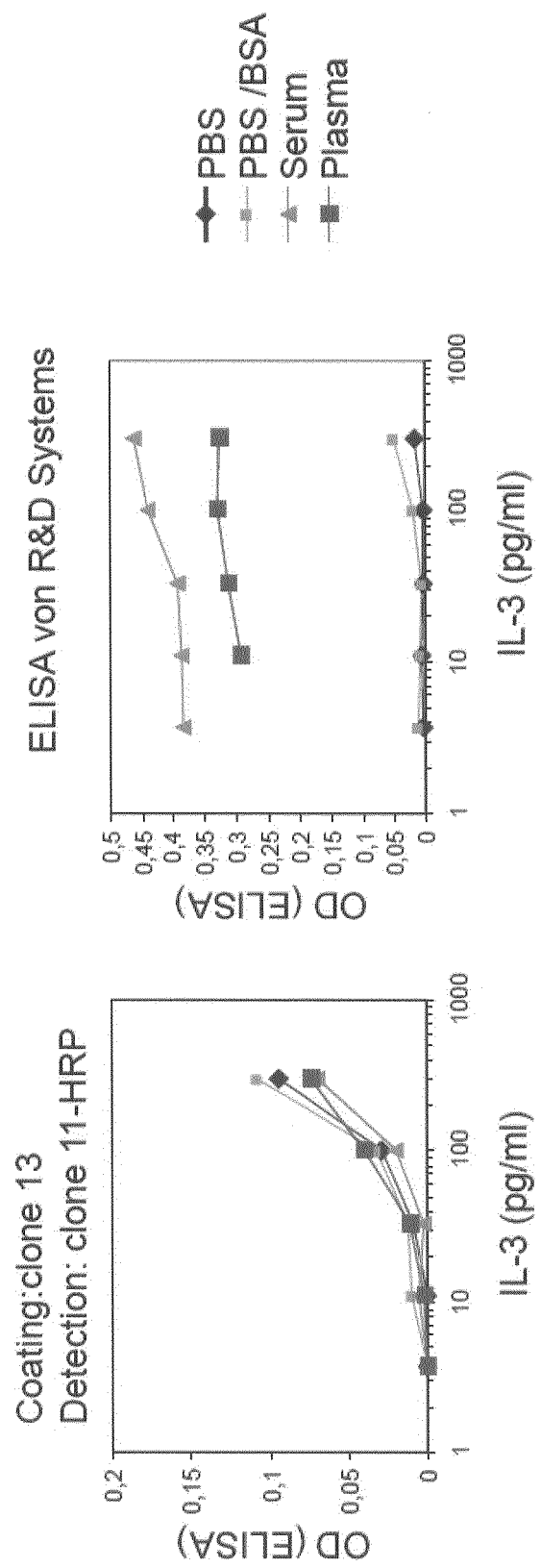
Figure 36:
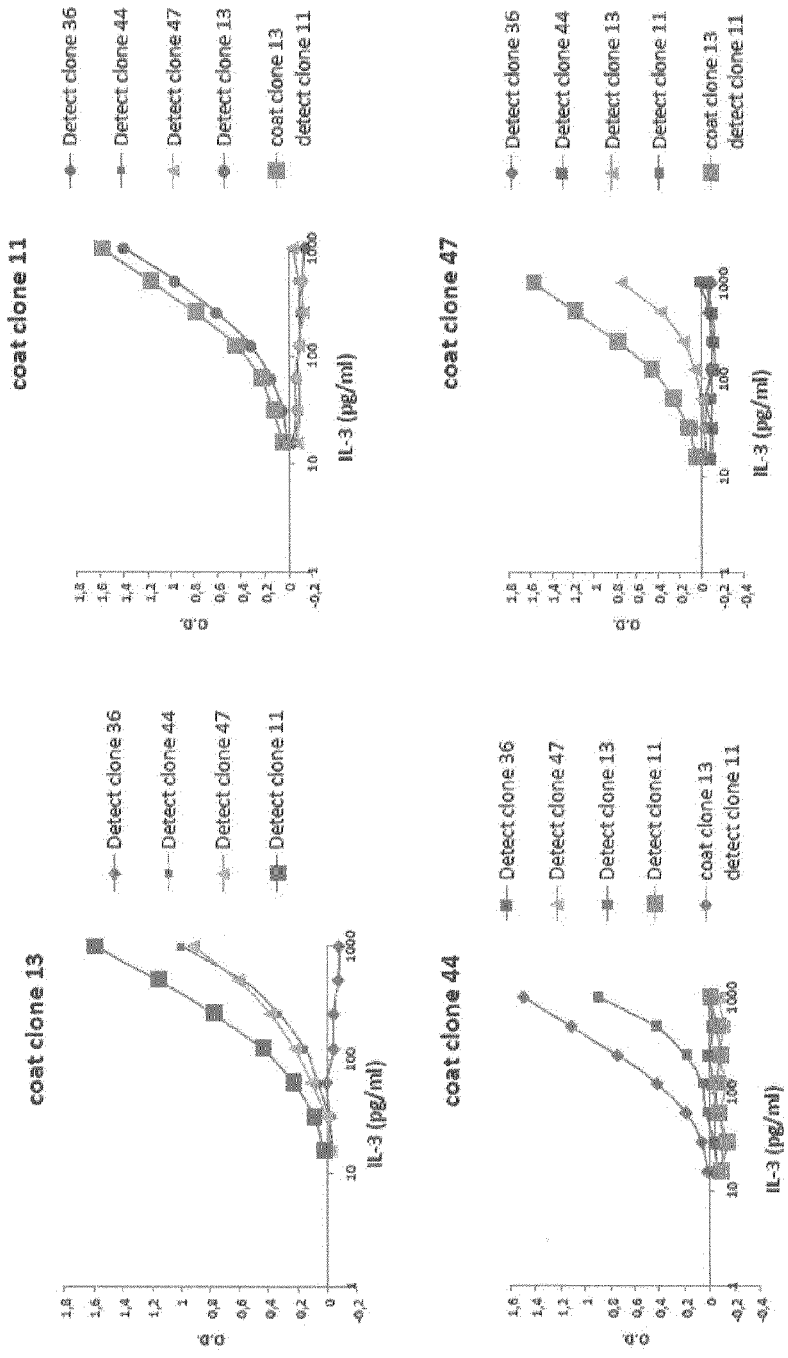
Figure 37:
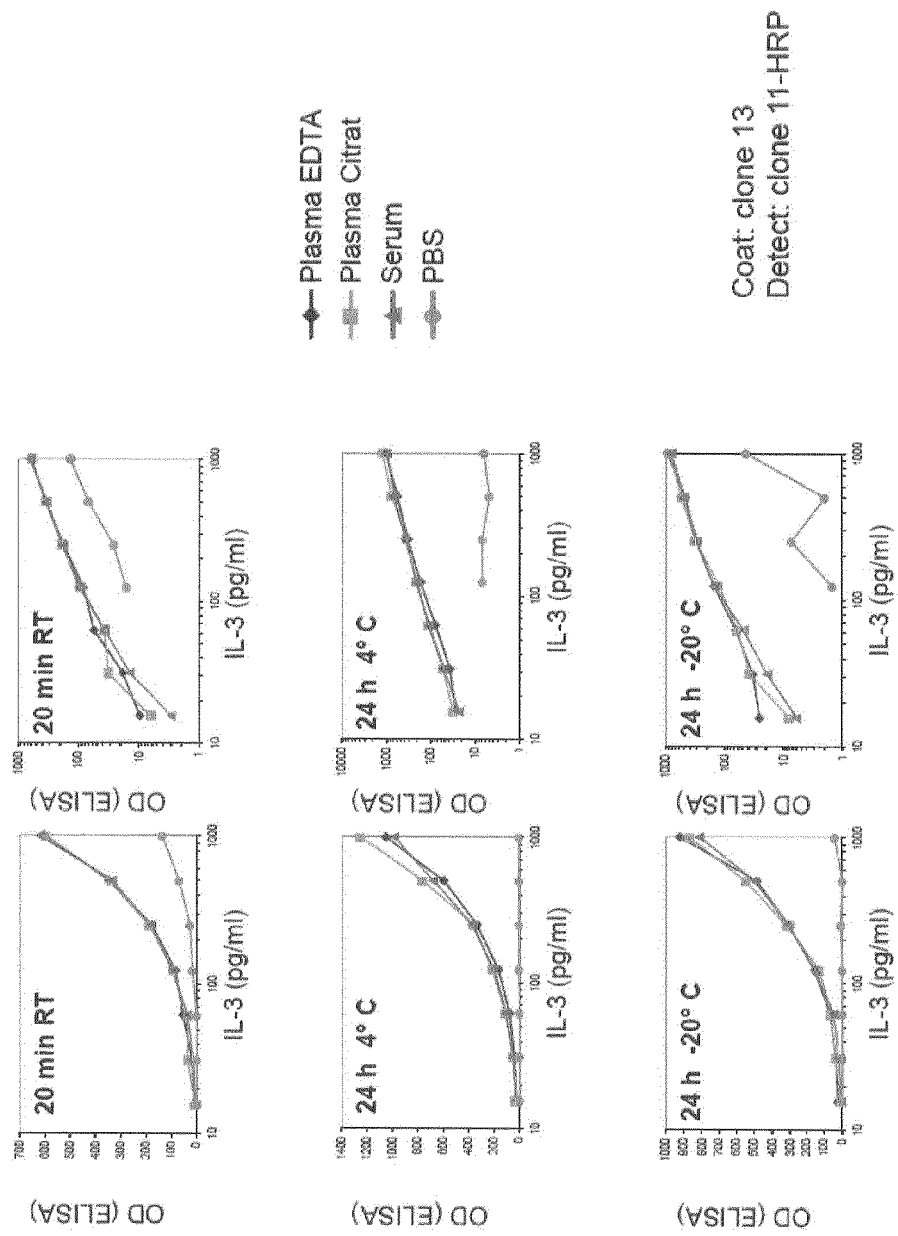
Figure 38:
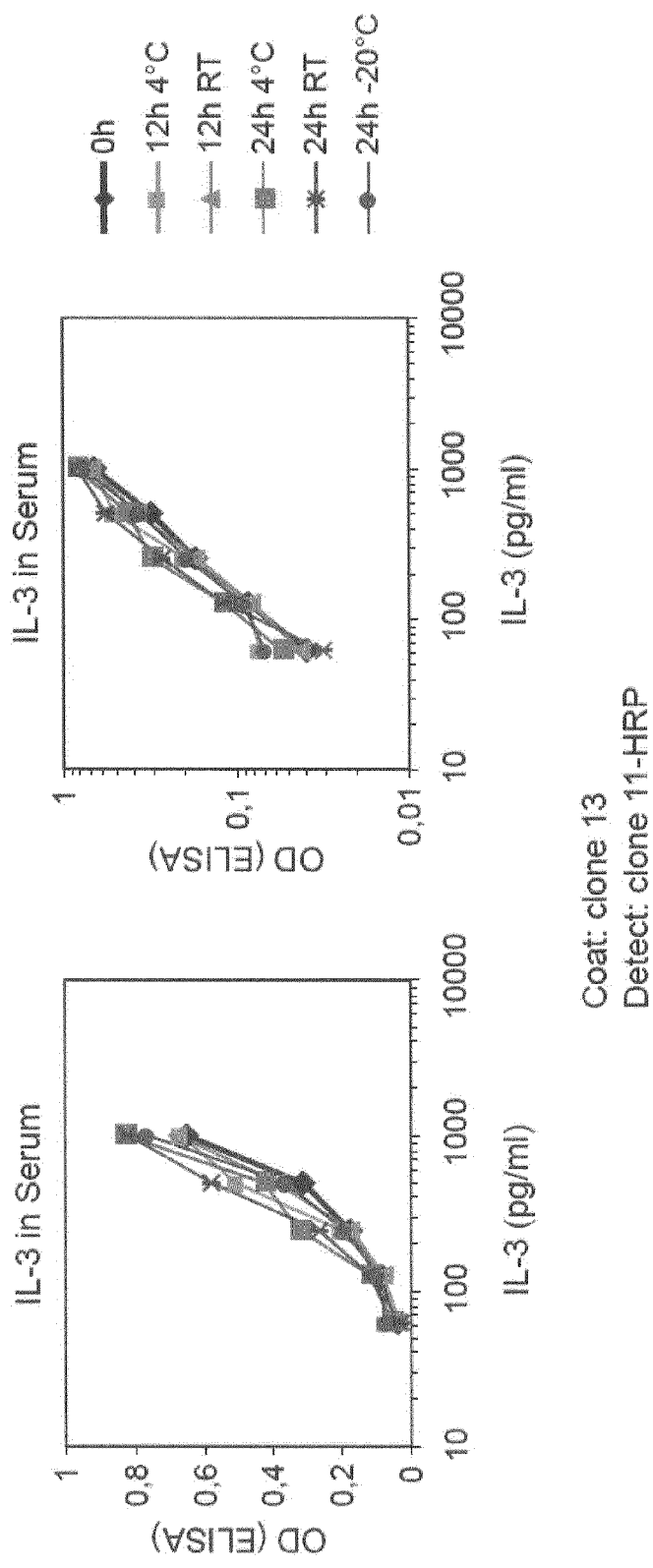
Figure 39:
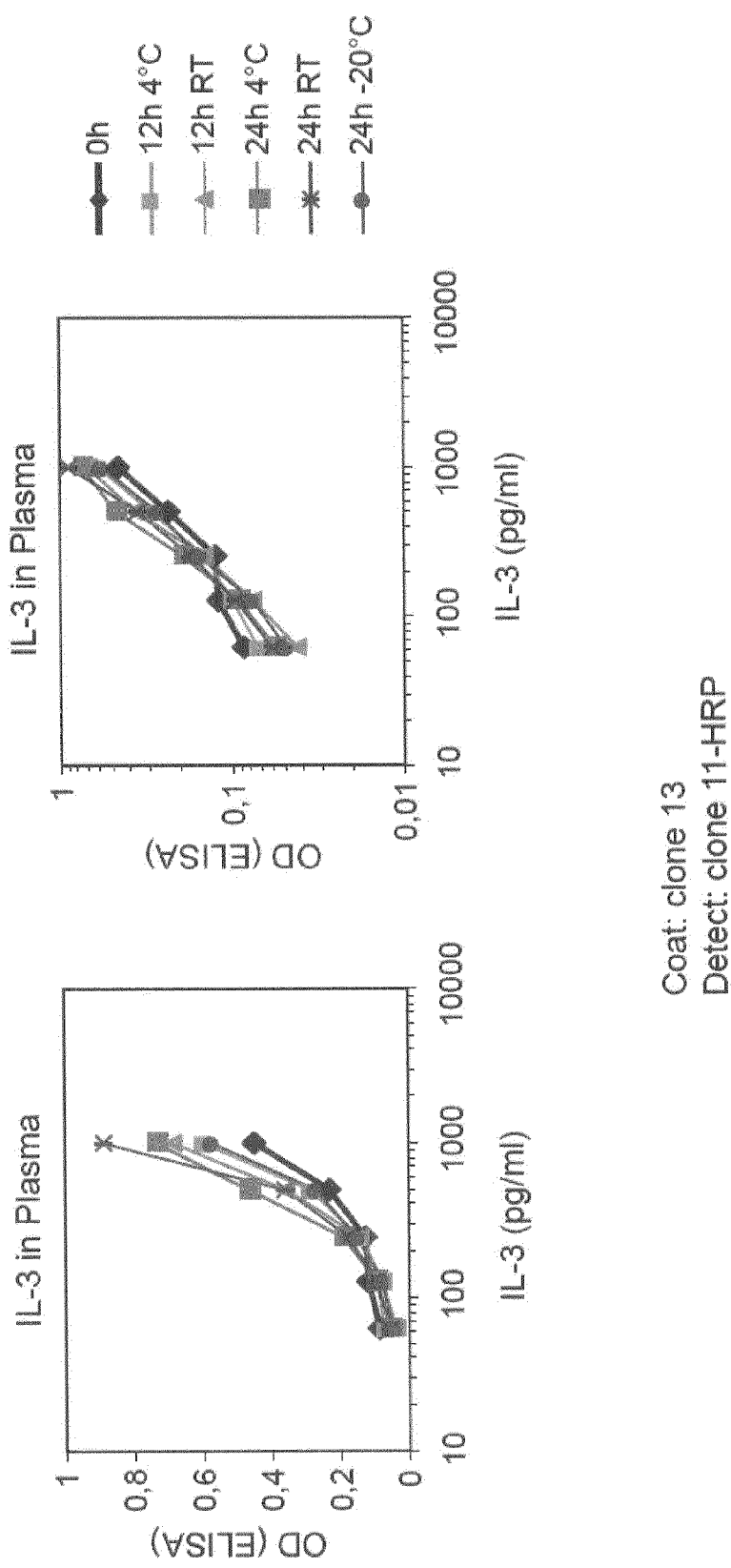
Figure 40:
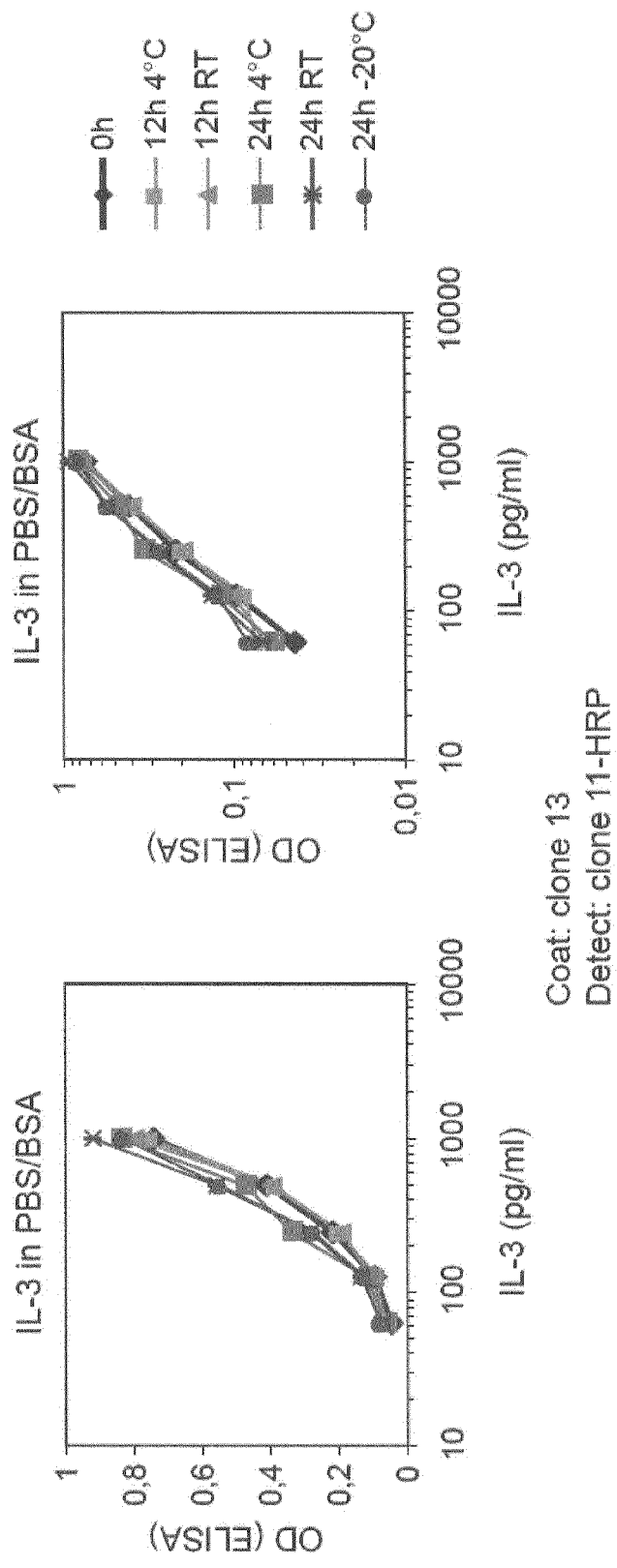

The results of this experiment are shown in FIGS. 33 to 36 and indicate that antibody clone 8 is not suitable as either coating or detection antibody, whereas antibody clones 11 and 13 are both suitable as coating and detection antibodies and the best results are achieved using clone 13 as coating and clone 11-HRP as detection antibody. It is furthermore observed that the commercially available IL-3 ELISA test kit obtainable from R&D Systems shows a remarkably lower sensitivity as an ELISA test kit according to the present invention with antibody clones 13 and 11 (FIG. 33). It was also observed that the IL-3 ELISA test kit of R&D Systems showed high background signals and therefore was not sufficiently reliable and sensitive when plasma or serum samples are used. An inventive test kit with clones 13/11, on the other hand, retained the same sensitivity as when using PBS or PBS/BSA samples also for plasma and serum (comparison shown in FIG. 36). Tests performed with different plasma samples (Plasma EDTA, Plasma Citrat) and serum could also be shown to be stable for at least 24 hours at room temperature (FIG. 37) and there was also no detectable signal loss after freezing and thawing of the samples (FIGS. 38 to 40).

EXAMPLE 8

Analysis of IL-3 Level in Plasma of Patients

An ELISA assay with clone 13 as coating and clone 11-HRP as detection antibody was performed for patients with inflammatory joint diseases. Test conditions and reagents were as described in Example 7. The results are shown in FIG. 41.

It was observed that in patients with non-active RA (DAS28<2.6, N=9) the mean plasma level of IL-3 was significantly lower (12 pg/ml) than for patients with active RA (DAS28≥2.6, N=45; IL-3=73 pg/ml). For patients suffering from a different form of arthritis (non-rheumatoid arthritis, n=10), also significantly lower mean IL-3 plasma levels (IL-3=1 pg/ml) were observed than for patients with active RA.

Remarkably, there were two groups of patients with active RA (DAS≥2.6). About half of the patients (N=21) showed very low IL-3 plasma levels (mean value IL-3=1.3 pg/ml, SEM (standard error of the mean)=0.27 pg/ml), whereas the second group (N=24) showed very high IL-3 levels (mean value IL-3=136 pg/ml, SEM=35 pg/ml). The ability to perform the test according to the present invention and to gain reliable and specific information about the IL-3 levels in the patients allows for a stratification of active-RA patients for a therapeutic IL-3 blocking treatment into subgroups with high and with low IL-3 levels. Patients with high IL-3 levels can be considered as a target group that will greatly benefit from such treatment.

For a further experiment, random plasma samples from patients treated at the University Hospital Regensburg were analyzed. The diagnosis of these patients was not known as the samples were analyzed in an anonymous way. The data obtained are shown in FIG. 42 and indicate that only a very low percentage of patients (4.7%) treated at the University Hospital express high levels of IL-3 while most of the patients express no IL-3 or very low levels thereof.

In further experiments plasma IL-3, IL-6 and TNF-α levels have been analysed in patients suffering from arthritis/arthralgia (no rheumatoid arthritis; n=87) or from rheumatoid arthritis (n=108) (FIG. 43). The obtained data clearly demonstrate that IL-3 but not IL-6 or TNF-α can separate between RA and non-RA types of arthritis.

Within the group of RA patients it was found that IL-3 and IL-6 but not TNF-α levels were strongly increased in patients with active RA (DAS28>2.6; n=93) compared to patients with non-active RA (DAS28≤2.6; n=15). Still, the IL-6 levels were clearly decreased in comparison to the IL-3 levels (FIG. 44).

As shown in FIG. 45>60% of the patients not responding to DMARDs/biologicals express high IL-3 levels. Among those patients that did not respond to current therapies patients with high IL-3 levels were more frequent. These patients would qualify for treatment with anti-IL-3 antibodies since the data indicate that patients with high IL-3 levels obviously do not respond to other kinds of therapies like, e.g., DMARDs or biologicals.

PCT

| 0-1 | Form PCT/RO/134 (SAFE) Indications Relating to Deposited Microorganism(s) or Other Biological Material (PCT Rule 13bis) | |
|---|---|---|
| 0-1-1 | Prepared Using | PCT Online Filing Version 3.5.000.235 MT/FOP 20020701/0.20.5.20 |
| 0-2 | International Application No. | PCT/EP 2013/061121 |
| 0-3 | Applicant's or agent's file reference | 52958PWO |

| 1 | The indications made below relate to the deposited microorganism(s) or other biological material referred to in the description on: | |
|---|---|---|
| 1-1 | page | 13 |
| 1-2 | line | 14-15 |
| 1-3 | Identification of deposit | |
| 1-3-1 | Name of depositary institution | DSMZ DSMZ-Deutsche Sammlung von Mikroorganismen und Zellkulturen GmbH |
| 1-3-2 | Address of depositary institution | Inhoffenstr. 7B, D-38124 Braunschweig, Germany |
| 1-3-3 | Date of deposit | 23 March 2012 (23.03.2012) |
| 1-3-4 | Accession Number | DSMZ DSM ACC3163 |
| 1-5 | Designated States for Which Indications are Made | All designations |
| 2 | The indications made below relate to the deposited microorganism(s) or other biological material referred to in the description on: | |
| 2-1 | page | 14 |
| 2-2 | line | 5-6 |
| 2-3 | Identification of deposit | |
| 2-3-1 | Name of depositary institution | DSMZ DSMZ-Deutsche Sammlung von Mikroorganismen und Zellkulturen GmbH |
| 2-3-2 | Address of depositary institution | Inhoffenstr. 7B, D-38124 Braunschweig, Germany |
| 2-3-3 | Date of deposit | 23 March 2012 (23.03.2012) |
| 2-3-4 | Accession Number | DSMZ DSM ACC3166 |
| 2-5 | Designated States for Which Indications are Made | All designations |

PCT

| 3 | The indications made below relate to the deposited microorganism(s) or other biological material referred to in the description on: | |
|---|---|---|
| 3-1 | page | 19 |
| 3-2 | line | 13 |
| 3-3 | Identification of deposit | |
| 3-3-1 | Name of depositary institution | DSMZ DSMZ-Deutsche Sammlung von Mikroorganismen und Zellkulturen GmbH |
| 3-3-2 | Address of depositary institution | Inhoffenstr. 7B, D-38124 Braunschweig, Germany |
| 3-3-3 | Date of deposit | 23 March 2012 (23.03.2012) |
| 3-3-4 | Accession Number | DSMZ DSM ACC3164 |
| 3-5 | Designated States for Which Indications are Made | All designations |
| 4 | The indications made below relate to the deposited microorganism(s) or other biological material referred to in the description on: | |
| 4-1 | page | 19 |
| 4-2 | line | 14 |
| 4-3 | Identification of deposit | |
| 4-3-1 | Name of depositary institution | DSMZ DSMZ-Deutsche Sammlung von Mikroorganismen und Zellkulturen GmbH |
| 4-3-2 | Address of depositary institution | Inhoffenstr. 7B, D-38124 Braunschweig, Germany |
| 4-3-3 | Date of deposit | 23 March 2012 (23.03.2012) |
| 4-3-4 | Accession Number | DSMZ DSM ACC3167 |
| 4-5 | Designated States for Which Indications are Made | All designations |
| 5 | The indications made below relate to the deposited microorganism(s) or other biological material referred to in the description on: | |
| 5-1 | page | 31 table 1 |
| 5-2 | line | Clone 36 36.26.10 |
| 5-3 | Identification of deposit | |
| 5-3-1 | Name of depositary institution | DSMZ DSMZ-Deutsche Sammlung von Mikroorganismen und Zellkulturen GmbH |
| 5-3-2 | Address of depositary institution | Inhoffenstr. 7B, D-38124 Braunschweig, Germany |
| 5-3-3 | Date of deposit | 23 March 2012 (23.03.2012) |
| 5-3-4 | Accession Number | DSMZ DSM ACC3165 |
| 5-5 | Designated States for Which Indications are Made | All designations |

FOR RECEIVING OFFICE USE ONLY

| 0-4 | This form was received with the international application: (yes or no) | Yes |
|---|---|---|
| 0-4-1 | Authorized officer | Gatinet, Bruno |

PCT

FOR INTERNATIONAL BUREAU USE ONLY

| 0-5 | This form was received by the international Bureau on: | 03 June 2013 (03.06.2013) |
|---|---|---|
| 0-5-1 | Authorized officer | Nathalie WAGNER |

The invention claimed is:

1. An anti-interleukin-3 (IL-3) antibody or fragment thereof which specifically binds to an epitope contained within the N-terminal 20 amino acids of the amino acid sequence of human IL-3 according to SEQ ID NO: 1.

2. The anti-IL3 antibody or fragment thereof according to claim 1, which specifically binds to an epitope comprising the sequence motif SWVN, SEQ ID NO: 2.

3. The anti-IL3 or fragment thereof according to claim 1, wherein the antibody is a polyclonal, monoclonal, chimeric, human or humanized antibody.

4. A pharmaceutical composition which contains a pharmaceutically effective amount of an anti-IL-3 antibody or fragment thereof according to claim 1 and optionally pharmaceutically acceptable adjuvants, excipients and/or carriers.

5. The pharmaceutical composition of claim 4, wherein the composition comprises a pharmaceutically acceptable adjuvant, excipient and/or carrier.

6. Anti-IL-3 antibody clone 11 (DSM ACC3163) deposited at DSMZ.

7. A nucleic acid, that encodes an anti-IL-3 antibody or fragment thereof according to claim 1.

8. A hybridoma cell line that produces an antibody according to claim 1.

9. A method for determining the IL-3 level in a body fluid, of a patient, wherein the method comprises:
   a) adding an anti-IL-3 antibody or fragment thereof according to claim 1 to a sample comprising said body fluid, under conditions which allow for binding of said antibody or fragment thereof to IL-3;
   b) and detecting the amount of antibody-bound IL-3 in said sample.

10. The method of claim 9, wherein the body fluid is blood, plasma or serum.

11. A method according to claim 9, wherein the method is performed as an enzyme-linked immunosorbent assay (ELISA) using two anti-IL-3 antibodies, wherein one of the antibodies is fixed to a solid phase, wherein the other antibody carries a detectable label, and wherein one of the antibodies is an anti-IL-3 antibody or fragment according to claim 1.

12. A method according to claim 11, wherein the antibody carrying a detectable label is the antibody clone 11 or an antigen-binding fragment thereof.

\* \* \* \* \*

SEQUENCE LISTING

<160> NUMBER OF SEQ ID NOS: 13

<210> SEQ ID NO 1
<211> LENGTH: 133
<212> TYPE: PRT
<213> ORGANISM: Homo sapiens
<220> FEATURE:
<221> NAME/KEY: Human IL-3 (without signal peptide)
<222> LOCATION: (1)..(133)

<400> SEQUENCE: 1

Ala Pro Met Thr Gln Thr Thr Pro Leu Lys Thr Ser Trp Val Asn Cys
1               5                   10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
    50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
    130

<210> SEQ ID NO 2
<211> LENGTH: 4
<212> TYPE: PRT
<213> ORGANISM: Homo sapiens
<220> FEATURE:
<221> NAME/KEY: Human IL-3 epitope
<222> LOCATION: (1)..(4)

<400> SEQUENCE: 2

Ser Trp Val Asn
1

<210> SEQ ID NO 3
<211> LENGTH: 27
<212> TYPE: PRT
<213> ORGANISM: Homo sapiens

<400> SEQUENCE: 3

Ala Pro Met Thr Gln Thr Thr Pro Leu Lys Thr Ser Trp Val Asn Cys
1               5                   10                  15

Ser Asn Met Ile Asp Glu Ile Ile Thr His Leu
            20                  25

<210> SEQ ID NO 4
<211> LENGTH: 27
<212> TYPE: PRT
<213> ORGANISM: Homo sapiens

<400> SEQUENCE: 4

Glu Ile Ile Thr His Leu Lys Gln Pro Pro Leu Pro Leu Leu Asp Phe
1               5                   10                  15

Asn Asn Leu Asn Gly Glu Asp Gln Asp Ile Leu
            20                  25

<210> SEQ ID NO 5
<211> LENGTH: 27
<212> TYPE: PRT
<213> ORGANISM: Homo sapiens

<400> SEQUENCE: 5

Glu Asp Gln Asp Ile Leu Met Glu Asn Asn Leu Arg Arg Pro Asn Leu
1               5                   10                  15

Glu Ala Phe Asn Arg Ala Val Lys Ser Leu Gln
            20                  25

<210> SEQ ID NO 6
<211> LENGTH: 27
<212> TYPE: PRT
<213> ORGANISM: Homo sapiens

<400> SEQUENCE: 6

Ala Val Lys Ser Leu Gln Asn Ala Ser Ala Ile Glu Ser Ile Leu Lys
1               5                   10                  15

Asn Leu Leu Pro Cys Leu Pro Leu Ala Thr Ala
            20                  25

<210> SEQ ID NO 7
<211> LENGTH: 27
<212> TYPE: PRT
<213> ORGANISM: Homo sapiens

<400> SEQUENCE: 7

Leu Pro Leu Ala Thr Ala Ala Pro Thr Arg His Pro Ile His Ile Lys
1               5                   10                  15

Asp Gly Asp Trp Asn Glu Phe Arg Arg Lys Leu
            20                  25

<210> SEQ ID NO 8
<211> LENGTH: 28
<212> TYPE: PRT
<213> ORGANISM: Homo sapiens

<400> SEQUENCE: 8

Glu Phe Arg Arg Lys Leu Thr Phe Tyr Leu Lys Thr Leu Glu Asn Ala
1               5                   10                  15

Gln Ala Gln Gln Thr Thr Leu Ser Leu Ala Ile Phe
            20                  25

<210> SEQ ID NO 9
<211> LENGTH: 24
<212> TYPE: PRT
<213> ORGANISM: Homo sapiens

<400> SEQUENCE: 9

Ala Pro Met Thr Gln Thr Thr Pro Leu Lys Thr Ser Trp Val Asn Cys
1               5                   10                  15

Ser Asn Met Ile Asp Glu Ile Ile
            20

<210> SEQ ID NO 10
<211> LENGTH: 24
<212> TYPE: PRT
<213> ORGANISM: Macaca mulatta

```
<400> SEQUENCE: 10

Ala Pro Met Thr Gln Thr Thr Ser Leu Lys Thr Ser Trp Ala Lys Cys
1               5                   10                  15

Ser Asn Met Ile Asp Glu Ile Ile
            20

<210> SEQ ID NO 11
<211> LENGTH: 24
<212> TYPE: PRT
<213> ORGANISM: artificial sequence
<220> FEATURE:
<223> OTHER INFORMATION: mutated human sequence

<400> SEQUENCE: 11

Ala Pro Met Thr Gln Thr Thr Pro Leu Lys Thr Ser Trp Ala Lys Cys
1               5                   10                  15

Ser Asn Met Ile Asp Glu Ile Ile
            20

<210> SEQ ID NO 12
<211> LENGTH: 24
<212> TYPE: PRT
<213> ORGANISM: Artificial sequence
<220> FEATURE:
<223> OTHER INFORMATION: mutated human sequence

<400> SEQUENCE: 12

Ala Pro Met Thr Gln Thr Thr Ser Leu Lys Thr Ser Trp Val Asn Cys
1               5                   10                  15

Ser Asn Met Ile Asp Glu Ile Ile
            20

<210> SEQ ID NO 13
<211> LENGTH: 26
<212> TYPE: PRT
<213> ORGANISM: Callithrix jacchus

<400> SEQUENCE: 13

Ala Ala Pro Thr Gln Thr Met Pro Leu Lys Thr Gln Val Asn Cys
1               5                   10                  15

Ser Asn Leu Arg Glu Glu Ile Val Thr Leu
            20                  25
```